(12) United States Patent
Xu et al.

(10) Patent No.: US 7,008,772 B1
(45) Date of Patent: Mar. 7, 2006

(54) COMPOUNDS FOR IMMUNODIAGNOSIS OF PROSTATE CANCER AND METHODS FOR THEIR USE

(75) Inventors: Jiangchun Xu, Bellevue, WA (US); Davin C. Dillon, Redmond, WA (US)

(73) Assignee: Corixa Corporation, Seattle, WA (US)

( * ) Notice: Subject to any disclaimer, the term of this patent is extended or adjusted under 35 U.S.C. 154(b) by 0 days.

(21) Appl. No.: 09/116,134

(22) Filed: Jul. 14, 1998

Related U.S. Application Data

(63) Continuation-in-part of application No. 09/030,606, filed on Feb. 25, 1998, now Pat. No. 6,887,660, which is a continuation-in-part of application No. 09/020,747, filed on Feb. 9, 1998, now abandoned, which is a continuation-in-part of application No. 08/904,809, filed on Aug. 1, 1997, now abandoned, which is a continuation-in-part of application No. 08/806,596, filed on Feb. 25, 1997, now abandoned.

(51) Int. Cl.
*G01N 33/53* (2006.01)

(52) U.S. Cl. .................. 435/7.1; 435/7.23; 530/387.1; 530/388.1; 530/387.7; 530/389.1; 424/184.4; 424/185.1

(58) Field of Classification Search ............... 435/7.23, 435/7.1; 530/387.1, 350, 387.7, 388.1, 389.1; 536/23.1; 424/184.1, 185.1
See application file for complete search history.

(56) References Cited

U.S. PATENT DOCUMENTS

| | | | |
|---|---|---|---|
| 5,786,148 A | | 7/1998 | Bandman et al. ............... 435/6 |
| 6,130,043 A | * | 10/2000 | Billing-Medel et al. ........ 435/6 |
| 6,252,047 B1 | * | 6/2001 | Billing-Medel et al. .... 530/350 |
| 2002/0086301 A1 | | 7/2002 | Billing-Medel et al. ........ 435/6 |

FOREIGN PATENT DOCUMENTS

| | | |
|---|---|---|
| EP | 652 014 A1 | 5/1995 |
| WO | WO 93/14755 | 8/1993 |
| WO | WO 93/25224 | 12/1993 |
| WO | WO 94/09820 | 5/1994 |
| WO | WO 95/04548 | 2/1995 |
| WO | WO 95/30758 | 11/1995 |
| WO | WO 96/21671 | 7/1996 |

OTHER PUBLICATIONS

Alberts, et al Mol. Biol. Cell, 3$^{rd}$ Ed, p. 465, 1994.*
Shantz, et al. Int. J. Biochem & Cell Biol. 31 : 107-122, 1999.*
Mc Clean et al. Eur. J. Cancer, 29(A) : 2243-2248, 1993.*
Fu et al. Eurbio J. 15 : 4392-4401, 1996.*
Corey et al. Clin. Chemistry 43(3) : 443-452, 1997.*
Burgers et al. J. Cell Biol. 11 : 2129-2138, 1990.*
Lazar et al Mol. Cell Biol. 8 : 1247-1252, 1988.*
Tao et al. J. Immunol. 143(8) : 2595-2601, 1989.*
Gillies et al. Human Antibodies & Hydridonias 1(1) : 47-54, 1990.*
MPSRCH search report, 2002, us-09-116-134-113.rai, pp. 2-3.*
Gelmini S et al, 2001, Clin Chem Lab Med, 39(5): 385-91.*
Schmid S et al, 2001, J comparative Neurology, 430(2): 160-71.*
Conner et al, 1996, Mol Brain Res, 42: 1-17.*
Alexeyev et al., "Improved antibiotic-resistance gene cassettes and omega elements for *Escherichia coli* vector construction and in vitro deletion/insertion mutagenesis," *Gene* 160: 63-67, 1995.
Blok et al., "Isolation of cDNAs That Are Differentially Expressed Between Androgen-Dependent and Androgen-Independent Prostate Carcinoma Cells Using Differential Display PCR," *The Prostate* 26: 213-214, 1995.
Database EMBL Accession No. AA453562, Jun. 11, 1997, Hillier et al., "Homo sapiens cDNA Clone 788180."
El-Shirbiny, Prostatic Specific Antigen, *Advances In Clinical Chemistry* 31: 99-133, 1994.
Robson et al., "Indentification of prostatic androgen regulated genes using the differential display technique," *Proceedings Of The American Association For Cancer Research Meeting 86*, 36: p. 266, Abstract No. 1589, 1995.
Short et al., "λ ZAP: a bacteriophage λ expression vector with in vivo excision properties," *Nucleic Acids Research* 16(15): 7583-7600, 1988.

* cited by examiner

*Primary Examiner*—Susan Ungar
*Assistant Examiner*—Minh-Tam Davis
(74) *Attorney, Agent, or Firm*—Seed IP Law Group PLLC

(57) ABSTRACT

Compounds and methods for diagnosing prostate cancer are provided. The inventive compounds include polypeptides containing at least a portion of a prostate tumor protein. The inventive polypeptides may be used to generate antibodies useful for the diagnosis and monitoring of prostate cancer. Nucleic acid sequences for preparing probes, primers, and polypeptides are also provided.

3 Claims, No Drawings

SEQUENCE LISTING

<160> NUMBER OF SEQ ID NOS: 228

<210> SEQ ID NO 1
<211> LENGTH: 814
<212> TYPE: DNA
<213> ORGANISM: Homo sapien
<220> FEATURE:
<221> NAME/KEY: misc_feature
<222> LOCATION: (1)...(814)
<223> OTHER INFORMATION: n = A,T,C or G

<400> SEQUENCE: 1

```
ttttttttttt tttttcacag tataacagct ctttatttct gtgagttcta ctaggaaatc      60
atcaaatctg agggttgtct ggaggacttc aatacacctc cccccatagt gaatcagctt     120 ccaggggggtc cagtccctct ccttacttca tccccatccc atgccaaagg aagaccctcc    180
ctccttggct cacagccttc tctaggcttc ccagtgcctc caggacagag tgggttatgt     240
tttcagctcc atccttgctg tgagtgtctg gtgcgttgtg cctccagctt ctgctcagtg     300
cttcatggac agtgtccagc acatgtcact ctccactctc tcagtgtgga tccactagtt     360
ctagagcggc cgccaccgcg gtggagctcc agcttttgtt ccctttagtg agggttaatt     420
gcgcgcttgg cgtaatcatg gtcataactg tttcctgtgt gaaattgtta tccgctcaca    480
attccacaca acatacgagc cggaagcata agtgtaaag cctggggtgc ctaatgagtg     540
anctaactca cattaattgc gttgcgctca ctgnccgctt tccagtcngg aaaactgtcg    600
tgccagctgc attaatgaat cggccaacgc ncggggaaaa gcggtttgcg ttttgggggc    660
tcttccgctt ctcgctcact nantcctgcg ctcggtcntt cggctgcggg gaacggtatc    720
actcctcaaa ggnggtatta cggttatccn naaatcnggg gatacccngg aaaaaanttt    780
aacaaaaggg cancaaaggg cngaaacgta aaaa                                   814
```

<210> SEQ ID NO 2
<211> LENGTH: 816
<212> TYPE: DNA
<213> ORGANISM: Homo sapien
<220> FEATURE:
<221> NAME/KEY: misc_feature
<222> LOCATION: (1)...(816)
<223> OTHER INFORMATION: n = A,T,C or G

<400> SEQUENCE: 2

```
acagaaatgt tggatggtgg agcacctttc tatacgactt acaggacagc agatggggaa      60
ttcatggctg ttggagcaat agaacccag ttctacgagc tgctgatcaa aggacttgga      120
ctaaagtctg atgaacttcc caatcagatg agcatggatg attggccaga aatgaagaag     180
aagtttgcag atgtatttgc aaagaagacg aaggcagagt ggtgtcaaat ctttgacggc    240
acagatgcct gtgtgactcc ggttctgact tttgaggagg ttgttcatca tgatcacaac     300
```

| | |
|---|---|
| aaggaacggg gctcgtttat caccagtgag gagcaggacg tgagccccg cctgcacct | 360 |
| ctgctgttaa acaccccagc catcccttct ttcaaaaggg atccactagt tctagaagcg | 420 |
| gccgccaccg cggtggagct ccagcttttg ttccctttag tgagggttaa ttgcgcgctt | 480 |
| ggcgtaatca tggtcatagc tgtttcctgt gtgaaattgt tatccgctca caattccccc | 540 |
| aacatacgag ccggaacata agtgttaag cctggggtgc ctaatgantg agctaactcn | 600 |
| cattaattgc gttgcgctca ctgcccgctt tccagtcggg aaaactgtcg tgccactgcn | 660 |
| ttantgaatc ngccaccccc cgggaaaagg cggttgcntt ttgggcctct tccgctttcc | 720 |
| tcgctcattg atcctngcnc ccggtcttcg gctgcggna acggttcact cctcaaaggc | 780 |
| ggtntnccgg ttatccccaa acnggggata cccnga | 816 |

<210> SEQ ID NO 3
<211> LENGTH: 773
<212> TYPE: DNA
<213> ORGANISM: Homo sapien
<220> FEATURE:
<221> NAME/KEY: misc_feature
<222> LOCATION: (1)...(773)
<223> OTHER INFORMATION: n = A,T,C or G

<400> SEQUENCE: 3

| | |
|---|---|
| cttttgaaag aagggatggc tgggtgtttt aacagcagag gtgcagggcg ggggctcacg | 60 |
| tcctgctcct cactggtgat aaacgagccc cgttccttgt tgtgatcatg atgaacaacc | 120 |
| tcctcaaaag tcagaaccgg agtcacacag gcatctgtgc cgtcaaagat ttgacaccac | 180 |
| tctgccttcg tcttctttgc aaatacatct gcaaacttct tcttcatttc tggccaatca | 240 |
| tccatgctca tctgattggg aagttcatca gactttagtc canntccttt gatcagcagc | 300 |
| tcgtagaact ggggttctat tgctccaaca gccatgaatt cccatctgc tgtcctgtaa | 360 |
| gtcgtataga aaggtgctcc accatccaac atgttctgtc ctcgaggggg ggcccggtac | 420 |
| ccaattcgcc ctatantgag tcgtattacg cgcgctcact ggccgtcgtt ttacaacgtc | 480 |
| gtgactggga aaaccctggg cgttaccaac ttaatcgcct tgcagcacat ccccctttcg | 540 |
| ccagctgggc gtaatancga aaggcccgc accgatcgcc cttccaacag ttgcgcacct | 600 |
| gaatgggnaa atgggacccc cctgttaccg cgcattnaac ccccgcnggg tttngttgtt | 660 |
| accccacnt nnaccgctta cactttgcca gcgccttanc gcccgctccc tttcnccttt | 720 |
| cttcccttcc tttcncnccn ctttccccg gggtttcccc cntcaaaccc cna | 773 |

<210> SEQ ID NO 4
<211> LENGTH: 828
<212> TYPE: DNA
<213> ORGANISM: Homo sapien
<220> FEATURE:
<221> NAME/KEY: misc_feature
<222> LOCATION: (1)...(828)
<223> OTHER INFORMATION: n = A,T,C or G

<400> SEQUENCE: 4

| | |
|---|---|
| cctcctgagt cctactgacc tgtgctttct ggtgtggagt ccagggctgc taggaaaagg | 60 |
| aatgggcaga cacaggtgta tgccaatgtt tctgaaatgg gtataatttc gtcctctcct | 120 |
| tcggaacact ggctgtctct gaagacttct cgctcagttt cagtgaggac acacacaaag | 180 |
| acgtgggtga ccatgttgtt tgtggggtgc agagatggga ggggtggggc ccaccctgga | 240 |
| agagtggaca gtgacacaag gtggacactc tctacagatc actgaggata agctggagcc | 300 |
| acaatgcatg aggcacacac acagcaagga tgacnctgta aacatagccc acgctgtcct | 360 |

-continued

```
gngggcactg ggaagcctan atnaggccgt gagcanaaag aaggggagga tccactagtt      420
ctanagcggc cgccaccgcg gtgganctcc anctttgtt cccttagtg agggttaatt      480 gcgcgcttgg cntaatcatg gtcatanctn tttcctgtgt gaaattgtta tccgctcaca      540
attccacaca acatacganc cggaaacata aantgtaaac ctggggtgcc taatgantga      600
ctaactcaca ttaattgcgt tgcgctcact gcccgctttc caatcnggaa acctgtcttg      660
ccncttgcat tnatgaatcn gccaaccccc ggggaaaagc gtttgcgttt tgggcgctct      720
tccgcttcct cnctcantta ntccctncnc tcggtcattc cggctgcngc aaaccggttc      780 accnctcca aaggggtat tccggtttcc ccnaatccgg gganancc                    828
```

<210> SEQ ID NO 5
<211> LENGTH: 834
<212> TYPE: DNA
<213> ORGANISM: Homo sapien
<220> FEATURE:
<221> NAME/KEY: misc_feature
<222> LOCATION: (1)...(834)
<223> OTHER INFORMATION: n = A,T,C or G

<400> SEQUENCE: 5

```
tttttttttt ttttttactga tagatggaat ttattaagct tttcacatgt gatagcacat      60
agttttaatt gcatccaaag tactaacaaa aactctagca atcaagaatg gcagcatgtt     120 atttatataac aatcaacacc tgtggctttt aaaatttggt tttcataaga taatttatac     180
tgaagtaaat ctagccatgc ttttaaaaaa tgctttaggt cactccaagc ttggcagtta     240
acatttggca taaacaataa taaaacaatc acaatttaat aaataacaaa tacaacattg     300
taggccataa tcatatacag tataaggaaa aggtggtagt gttgagtaag cagttattag     360
aatagaatac cttggcctct atgcaaatat gtctagacac tttgattcac tcagccctga     420
cattcagttt tcaaagtagg agacaggttc tacagtatca ttttacagtt tccaacacat     480
tgaaaacaag tagaaaatga tgagttgatt tttattaatg cattacatcc tcaagagtta     540
tcaccaaccc ctcagttata aaaattttc aagtttatatt agtcatataa cttggtgtgc     600
ttattttaaa ttagtgctaa atggattaag tgaagacaac aatggtcccc taatgtgatt     660
gatattggtc attttacca gcttctaaat ctnaactttc aggcttttga actgaaacat     720
tgnatnacag tgttccanag ttncaaccta ctggaacatt acagtgtgct tgattcaaaa     780
tgttattttg ttaaaaatta aattttaacc tggtggaaaa ataatttgaa atna           834
```

<210> SEQ ID NO 6
<211> LENGTH: 818
<212> TYPE: DNA
<213> ORGANISM: Homo sapien
<220> FEATURE:
<221> NAME/KEY: misc_feature
<222> LOCATION: (1)...(818)
<223> OTHER INFORMATION: n = A,T,C or G

<400> SEQUENCE: 6

```
tttttttttt tttttttttt aagaccctca tcaatagatg gagacataca gaaatagtca      60
aaccacatct acaaaatgcc agtatcaggc ggcggcttcg aagccaaagt gatgtttgga     120
tgtaaagtga atattagtt ggcggatgaa gcagatagtg aggaaagttg agccaataat     180
gacgtgaagt ccgtggaagc ctgtggctac aaaaaatgtt gagccgtaga tgccgtcgga     240
aatggtgaag ggagactcga agtactctga ggcttgtagg agggtaaaat agagacccag     300
taaaattgta ataagcagtg cttgaattat ttggtttcgg ttgttttcta ttagactatg     360
```

```
gtgagctcag gtgattgata ctcctgatgc gagtaatacg gatgtgttta ggagtgggac    420
ttctagggga tttagcgggg tgatgcctgt tgggggccag tgccctccta gttgggggt     480 aggggctagg ctggagtggt aaaaggctca gaaaaatcct gcgaagaaaa aaacttctga    540
ggtaataaat aggattatcc cgtatcgaag gccttttgg acaggtggtg tgtggtggcc     600
ttggtatgtg ctttctcgtg ttacatcgcg ccatcattgg tatatggtta gtgtgttggg    660
ttantanggc ctantatgaa gaactttgg antggaatta aatcaatngc ttggccggaa     720
gtcattanga nggctnaaaa ggccctgtta ngggtctggg ctnggttta cccnacccat     780 ggaatncncc ccccggacna ntgnatccct attcttaa                             818
```

<210> SEQ ID NO 7
<211> LENGTH: 817
<212> TYPE: DNA
<213> ORGANISM: Homo sapien
<220> FEATURE:
<221> NAME/KEY: misc_feature
<222> LOCATION: (1)...(817)
<223> OTHER INFORMATION: n = A,T,C or G

<400> SEQUENCE: 7

```
tttttttttt tttttttttt tggctctaga gggggtagag gggtgctat aggtaaata      60 cgggccctat ttcaaagatt tttaggggaa ttaattctag gacgatgggt atgaaactgt    120
ggtttgctcc acagatttca gagcattgac cgtagtatac ccccggtcgt gtagcggtga    180
aagtggtttg gtttagacgt ccgggaattg catctgtttt taagcctaat gtggggacag    240
ctcatgagtg caagacgtct tgtgatgtaa ttattatacn aatgggggct tcaatcggga    300
gtactactcg attgtcaacg tcaaggagtc gcaggtcgcc tggttctagg aataatgggg    360
gaagtatgta ggaattgaag attaatccgc cgtagtcggt gttctcctag gttcaatacc    420
attggtggcc aattgatttg atggtaaggg gagggatcgt tgaactcgtc tgttatgtaa    480 aggatnccttt ngggatggga aggcnataa ggactangga tnaatggcgg gcangatatt    540
tcaaacngtc tctanttcct gaaacgtctg aaatgttaat aanaattaan tttngttatt    600
gaatnttnng gaaaagggct tacaggacta gaaaccaaat angaaaanta atnntaangg    660
cnttatcntn aaaggtnata accnctccta tnatcccacc caatngnatt ccccacncnn    720
acnattggat nccccanttc canaaaggc cnccccccgg tgnanncnc cttttgttcc      780 cttnantgan ggttattcnc ccctngcntt atcancc                              817
```

<210> SEQ ID NO 8
<211> LENGTH: 799
<212> TYPE: DNA
<213> ORGANISM: Homo sapien
<220> FEATURE:
<221> NAME/KEY: misc_feature
<222> LOCATION: (1)...(799)
<223> OTHER INFORMATION: n = A,T,C or G

<400> SEQUENCE: 8

```
catttccggg tttactttct aaggaaagcc gagcggaagc tgctaacgtg ggaatcggtg    60
cataaggaga actttctgct ggcacgcgct aggacaagc gggagagcga ctccgagcgt    120
ctgaagcgca cgtcccagaa ggtggacttg cactgaaac agctgggaca catccgcgag   180
tacgaacagc gcctgaaagt gctggagcgg gaggtccagc agtgtagccg cgtcctgggg   240 tgggtgccg angcctganc cgctctgcct tgctgccccc angtgggccg ccaccccctg    300
acctgcctgg gtccaaacac tgagccctgc tggcggactt caaggganaac ccccacangg   360
```

| | |
|---|---:|
| ggattttgct cctanantaa ggctcatctg ggcctcggcc ccccacctg gttggccttg | 420 |
| tctttgangt gagccccatg tccatctggg ccactgtcng gaccacctt ngggagtgtt | 480 |
| ctccttacaa ccacannatg cccggctcct cccggaaacc antcccancc tgngaaggat | 540 |
| caagncctgn atccactnnt nctanaaccg gccnccnccg cngtggaacc cnccttntgt | 600 |
| tcctttcnt tnagggttaa tnncgccttg gccttnccan ngtcctncnc nttttccnnt | 660 |
| gttnaaattg ttangcnccc nccnntcccn cnncnncnan cccgacccnn annttnnann | 720 |
| ncctgggggt nccnncngat tgacccnncc nccctntant tgcnttnggg nncnntgccc | 780 |
| ctttccctct ngggannncg | 799 |

<210> SEQ ID NO 9
<211> LENGTH: 801
<212> TYPE: DNA
<213> ORGANISM: Homo sapien
<220> FEATURE:
<221> NAME/KEY: misc_feature
<222> LOCATION: (1)...(801)
<223> OTHER INFORMATION: n = A,T,C or G

<400> SEQUENCE: 9

| | |
|---|---:|
| acgccttgat cctcccaggc tgggactggt tctggagga gccgggcatg ctgtggtttg | 60 |
| taangatgac actcccaaag gtggtcctga cagtggccca gatggacatg gggctcacct | 120 |
| caaggacaag gccaccaggt gcgggggccg aagcccacat gatccttact ctatgagcaa | 180 |
| aatcccctgt gggggcttct ccttgaagtc cgccancagg gctcagtctt tggacccang | 240 |
| caggtcatgg ggttgtngnc caactggggg ccncaacgca aaanggcnca gggcctcngn | 300 |
| cacccatccc angacgcggc tacactnctg gacctcccnc tccaccactt tcatgcgctg | 360 |
| ttcntacccg cgnatntgtc ccanctgttt cngtgccnac tccancttct nggacgtgcg | 420 |
| ctacatacgc ccggantcnc nctcccgctt tgtccctatc cacgtnccan caacaaattt | 480 |
| cnccntantg caccnattcc cacntttnnc agntttccnc nncgngcttc cttntaaaag | 540 |
| ggttganccc cggaaaatnc cccaaagggg ggggccngg tacccaactn cccccctnata | 600 |
| gctgaantcc ccatnaccnn gnctcnatgg anccntcct tttaannacn ttctnaactt | 660 |
| gggaananncc ctcgnccntn ccccccnttaa tcccnccttg cnangnncnt ccccnntcc | 720 |
| ncccnnntng gcntntnann cnaaaaaggc ccnnnancaa tctcctnncn cctcanttcg | 780 |
| ccanccctcg aaatcggccn c | 801 |

<210> SEQ ID NO 10
<211> LENGTH: 789
<212> TYPE: DNA
<213> ORGANISM: Homo sapien
<220> FEATURE:
<221> NAME/KEY: misc_feature
<222> LOCATION: (1)...(789)
<223> OTHER INFORMATION: n = A,T,C or G

<400> SEQUENCE: 10

| | |
|---|---:|
| cagtctatnt ggccagtgtg gcagctttcc ctgtggctgc cggtgccaca tgcctgtccc | 60 |
| acagtgtggc cgtggtgaca gcttcagccg ccctcaccgg gttcaccttc tcagccctgc | 120 |
| agatcctgcc ctacacactg gcctccctct accaccggga gaagcaggtg ttcctgccca | 180 |
| aataccgagg ggacactgga ggtgctagca gtgaggacag cctgatgacc agcttcctgc | 240 |
| caggccctaa gcctggagct cccttcccta atggacacgt gggtgctgga ggcagtggcc | 300 |
| tgctcccacc tccacccgcg ctctgcgggg cctctgcctg tgatgtctcc gtacgtgtgg | 360 |

```
tggtgggtga gcccaccgan gccagggtgg ttccgggccg gggcatctgc ctggacctcg    420
ccatcctgga tagtgcttcc tgctgtccca ngtggccca tccctgttta tgggctccat    480
tgtccagctc agccagtctg tcactgccta tatggtgtct gccgcaggcc tgggtctggt    540
cccatttact ttgctacaca ggtantattt gacaagaacg anttggccaa atactcagcg    600
ttaaaaaatt ccagcaacat tggggtgga aggcctgcct cactgggtcc aactccccgc    660
tcctgttaac cccatggggc tgccggcttg ccgccaatt tctgttgctg ccaaantnat    720
gtggctctct gctgccacct gttgctggct gaagtgcnta cngcncanct nggggggtng    780 ggngttccc                                                            789
```

\<210\> SEQ ID NO 11
\<211\> LENGTH: 772
\<212\> TYPE: DNA
\<213\> ORGANISM: Homo sapien
\<220\> FEATURE:
\<221\> NAME/KEY: misc_feature
\<222\> LOCATION: (1)...(772)
\<223\> OTHER INFORMATION: n = A,T,C or G

\<400\> SEQUENCE: 11

```
cccaccctac ccaaatatta gacaccaaca cagaaaagct agcaatggat tcccttctac     60
tttgttaaat aaataagtta aatatttaaa tgcctgtgtc tctgtgatgg caacagaagg    120
accaacaggc cacatcctga taaaggtaa aggggggtg gatcagcaaa agacagtgc      180 tgtgggctga ggggacctgg ttcttgtgtg ttgcccctca ggactcttcc cctacaaata    240
actttcatat gttcaaatcc catggaggag tgtttcatcc tagaaactcc catgcaagag    300
ctacattaaa cgaagctgca ggttaagggg cttanagatg ggaaaccagg tgactgagtt    360
tattcagctc ccaaaaaccc ttctctaggt gtgtctcaac taggaggcta gctgttaacc    420
ctgagcctgg gtaatccacc tgcagagtcc ccgcattcca gtgcatggaa cccttctggc    480
ctccctgtat aagtccagac tgaaaccccc ttggaaggnc tccagtcagg cagccctana    540
aactggggaa aaaagaaaag gacgccccan cccccagctg tgcanctacg cacctcaaca    600
gcacagggtg gcagcaaaaa aaccacttta ctttggcaca aacaaaaact nggggggca    660 accccggcac cccnangggg gttaacagga ancngggnaa cntggaaccc aattnaggca    720
ggcccnccac cccnaatntt gctgggaaat ttttcctccc ctaaattntt tc            772
```

\<210\> SEQ ID NO 12
\<211\> LENGTH: 751
\<212\> TYPE: DNA
\<213\> ORGANISM: Homo sapien
\<220\> FEATURE:
\<221\> NAME/KEY: misc_feature
\<222\> LOCATION: (1)...(751)
\<223\> OTHER INFORMATION: n = A,T,C or G

\<400\> SEQUENCE: 12

```
gccccaattc cagctgccac accacccacg gtgactgcat tagttcggat gtcatacaaa     60
agctgattga agcaaccctc tactttttgg tcgtgagcct tttgcttggt gcaggtttca    120
ttggctgtgt tggtgacgtt gtcattgcaa cagaatgggg gaaaggcact gttctctttg    180
aagtanggtg agtcctcaaa atccgtatag ttggtgaagc cacagcactt gagcccttc     240 atggtggtgt tccacacttg agtgaagtct tcctgggaac cataatcttt cttgatggca    300
ggcactacca gcaacgtcag ggaagtgctc agccattgtg gtgtacacca aggcgaccac    360
agcagctgcn acctcagcaa tgaagatgan gaggangatg aagaagaacg tcncgagggc    420
```

| | |
|---|---:|
| acacttgctc tcagtcttan caccatanca gcccntgaaa accaananca aagaccacna | 480 |
| cnccggctgc gatgaagaaa tnaccccncg ttgacaaact tgcatggcac tgggaccac | 540 |
| agtggcccna aaaatcttca aaaggatgc cccatcnatt gaccccccaa atgcccactg | 600 |
| ccaacagggg ctgccccacn cncnnaacga tganccnatt gnacaagatc tncntggtct | 660 |
| tnatnaacnt gaaccctgcn tngtggctcc tgttcaggnc cnnggcctga cttctnaann | 720 |
| aangaactcn gaagncccca cnggananc g | 751 |

<210> SEQ ID NO 13
<211> LENGTH: 729
<212> TYPE: DNA
<213> ORGANISM: Homo sapien
<220> FEATURE:
<221> NAME/KEY: misc_feature
<222> LOCATION: (1)...(729)
<223> OTHER INFORMATION: n = A,T,C or G

<400> SEQUENCE: 13

| | |
|---|---:|
| gagccaggcg tccctctgcc tgcccactca gtggcaacac ccgggagctg ttttgtcctt | 60 |
| tgtggancct cagcagtncc ctctttcaga actcantgcc aaganccctg aacaggagcc | 120 |
| accatgcagt gcttcagctt cattaagacc atgatgatcc tcttcaattt gctcatcttt | 180 |
| ctgtgtggtg cagccctgtt ggcagtgggc atctgggtgt caatcgatgg gcatccttt | 240 |
| ctgaagatct tcgggccact gtcgtccagt gccatgcagt ttgtcaacgt gggctacttc | 300 |
| ctcatcgcag ccggcgttgt ggtcttagct ctaggttcc tgggctgcta tggtgctaag | 360 |
| actgagagca agtgtgccct cgtgacgttc ttcttcatcc tcctcctcat cttcattgct | 420 |
| gaggttgcaa tgctgtggtc gccttggtgt acaccacaat ggctgagcac ttcctgacgt | 480 |
| tgctggtaat gcctgccatc aanaaaagat tatgggttcc caggaanact tcactcaagt | 540 |
| gttggaacac caccatgaaa gggctcaagt gctgtggctt cnnccaacta tacggatttt | 600 |
| gaagantcac ctacttcaaa gaaaanagtg ccttccccc atttctgttg caattgacaa | 660 |
| acgtccccaa cacagccaat tgaaaacctg cacccaaccc aaangggtcc ccaaccanaa | 720 |
| attnaaggg | 729 |

<210> SEQ ID NO 14
<211> LENGTH: 816
<212> TYPE: DNA
<213> ORGANISM: Homo sapien
<220> FEATURE:
<221> NAME/KEY: misc_feature
<222> LOCATION: (1)...(816)
<223> OTHER INFORMATION: n = A,T,C or G

<400> SEQUENCE: 14

| | |
|---|---:|
| tgctcttcct caaagttgtt cttgttgcca taacaaccac cataggtaaa gcgggcgcag | 60 |
| tgttcgctga aggggttgta gtaccagcgc ggatgctct ccttgcagag tcctgtgtct | 120 |
| ggcaggtcca cgcagtgccc tttgtcactg ggaaatgga tgcgctggag ctcgtcaaag | 180 |
| ccactcgtgt attttcaca ggcagcctcg tccgacgcgt cggggcagtt gggggtgtct | 240 |
| tcacactcca ggaaactgtc natgcagcag ccattgctgc agcggaactg gtgggctga | 300 |
| cangtgccag agcacactgg atggcgcctt ccatgnnan gggccctgng gaaagtccc | 360 |
| tganccccan anctgcctct caaangcccc accttgcaca ccccgacagg ctagaatgga | 420 |
| atcttcttcc cgaaaggtag ttnttcttgt tgcccaancc anccccntaa acaaactctt | 480 |
| gcanatctgc tccgnggggg tcntantacc ancgtgggaa aagaaccca ggcngcgaac | 540 |

| | |
|---|---:|
| caancttgtt tggatncgaa gcnataatct nctnttctgc ttggtggaca gcaccantna | 600 |
| ctgtnnanct ttagnccntg gtcctcntgg gttgnncttg aacctaatcn ccnntcaact | 660 |
| gggacaaggt aantngccnt cctttnaatt cccnancntn cccctggtt tggggttttn | 720 |
| cncnctccta ccccagaaan nccgtgttcc ccccaacta ggggccnaaa ccnttnttc | 780 |
| cacaaccctn ccccacccac gggttcngnt ggttng | 816 |

<210> SEQ ID NO 15
<211> LENGTH: 783
<212> TYPE: DNA
<213> ORGANISM: Homo sapien
<220> FEATURE:
<221> NAME/KEY: misc_feature
<222> LOCATION: (1)...(783)
<223> OTHER INFORMATION: n = A,T,C or G

<400> SEQUENCE: 15

| | |
|---|---:|
| ccaaggcctg ggcaggcata nacttgaagg tacaacccca ggaaccctg gtgctgaagg | 60 |
| atgtggaaaa cacagattgg cgcctactgc ggggtgacac ggatgtcagg gtagagagga | 120 |
| aagacccaaa ccaggtggaa ctgtggggac tcaaggaang cacctacctg ttccagctga | 180 |
| cagtgactag ctcagaccac ccagaggaca cggccaacgt cacagtcact gtgctgtcca | 240 |
| ccaagcagac agaagactac tgcctcgcat ccaacaangt gggtcgctgc cggggctctt | 300 |
| tcccacgctg gtactatgac cccacggagc agatctgcaa gagtttcgtt tatggaggct | 360 |
| gcttgggcaa caagaacaac taccttcggg aagaagagtg cattctancc tgtcngggtg | 420 |
| tgcaaggtgg gcctttgana ngcanctctg gggctcangc gactttcccc cagggcccct | 480 |
| ccatggaaag gcgccatcca ntgttctctg gcacctgtca gcccacccag ttccgctgca | 540 |
| ncaatggctg ctgcatcnac antttcctng aattgtgaca acaccccca ntgccccaa | 600 |
| ccctcccaac aaagcttccc tgttnaaaaa tacnccantt ggcttttnac aaacncccgg | 660 |
| cnccctccntt ttccccnntn aacaaagggc nctngcnttt gaactgcccn aaccengaa | 720 |
| tctnccnngg aaaantncc ccccctggtt cctnnaance cctccncnaa anctncccc | 780 |
| ccc | 783 |

<210> SEQ ID NO 16
<211> LENGTH: 801
<212> TYPE: DNA
<213> ORGANISM: Homo sapien
<220> FEATURE:
<221> NAME/KEY: misc_feature
<222> LOCATION: (1)...(801)
<223> OTHER INFORMATION: n = A,T,C or G

<400> SEQUENCE: 16

| | |
|---|---:|
| gccccaattc cagctgccac accacccacg gtgactgcat tagttcggat gtcatacaaa | 60 |
| agctgattga agcaaccctc tacttttggg tcgtgagcct tttgcttggt gcaggtttca | 120 |
| ttggctgtgt tggtgacgtt gtcattgcaa cagaatgggg gaaaggcact gttctctttg | 180 |
| aagtagggtg agtcctcaaa atccgtatag ttggtgaagc cacagcactt gagccctttc | 240 |
| atggtggtgt tccacacttg agtgaagtct tcctgggaac cataatcttt cttgatggca | 300 |
| ggcactacca gcaacgtcag gaagtgctca gccattgtgg tgtacaccaa ggcgaccaca | 360 |
| gcagctgcaa cctcagcaat gaagatgagg aggaggatga agaagaacgt cncgagggca | 420 |
| cacttgctct ccgtcttagc accatagcag cccangaaac caagagcaaa gaccacaacg | 480 |
| ccngctgcga atgaaagaaa ntacccacgt tgacaaactg catggccact ggacgacagt | 540 |

-continued

| | |
|---|---|
| tggcccgaan atcttcagaa aagggatgcc ccatcgattg aacacccana tgcccactgc | 600 |
| cnacagggct gcnccncncn gaaagaatga gccattgaag aaggatcntc ntggtcttaa | 660 |
| tgaactgaaa ccntgcatgg tggcccctgt tcagggctct tggcagtgaa ttctganaaa | 720 |
| aaggaacngc ntnagccccc ccaaangana aacacccccc gggtgttgcc ctgaattggc | 780 |
| ggccaaggan ccctgccccn g | 801 |

<210> SEQ ID NO 17
<211> LENGTH: 740
<212> TYPE: DNA
<213> ORGANISM: Homo sapien
<220> FEATURE:
<221> NAME/KEY: misc_feature
<222> LOCATION: (1)...(740)
<223> OTHER INFORMATION: n = A,T,C or G

<400> SEQUENCE: 17

| | |
|---|---|
| gtgagagcca ggcgtccctc tgcctgccca ctcagtggca acacccggga gctgttttgt | 60 |
| cctttgtgga gcctcagcag ttccctcttt cagaactcac tgccaagagc cctgaacagg | 120 |
| agccaccatg cagtgcttca gcttcattaa gaccatgatg atcctcttca atttgctcat | 180 |
| ctttctgtgt ggtgcagccc tgttggcagt gggcatctgg gtgtcaatcg atgggcatc | 240 |
| ctttctgaag atcttcgggc cactgtcgtc cagtgccatg cagtttgtca cgtgggcta | 300 |
| cttcctcatc gcagccggcg ttgtggtctt tgctcttggt ttcctgggct gctatggtgc | 360 |
| taagacggag agcaagtgtg ccctcgtgac gttcttcttc atcctcctcc tcatcttcat | 420 |
| tgctgaagtt gcagctgctg tggtcgcctt ggtgtacacc acaatggctg aaccattcct | 480 |
| gacgttgctg gtantgcctg ccatcaanaa agattatggg ttcccaggaa aaattcactc | 540 |
| aantntggaa caccnccatg aaaagggctc caatttctgn tggcttcccc aactataccg | 600 |
| gaattttgaa agantcnccc tacttccaaa aaaaaanant tgcctttncc ccnttctgt | 660 |
| tgcaatgaaa acntcccaan acngccaatn aaaacctgcc cnnncaaaaa ggntcncaaa | 720 |
| caaaaaaant nnaagggttn | 740 |

<210> SEQ ID NO 18
<211> LENGTH: 802
<212> TYPE: DNA
<213> ORGANISM: Homo sapien
<220> FEATURE:
<221> NAME/KEY: misc_feature
<222> LOCATION: (1)...(802)
<223> OTHER INFORMATION: n = A,T,C or G

<400> SEQUENCE: 18

| | |
|---|---|
| ccgctggttg cgctggtcca gngnagccac gaagcacgtc agcatacaca gcctcaatca | 60 |
| caaggtcttc cagctgccgc acattacgca gggcaagagc ctccagcaac actgcatatg | 120 |
| ggatacactt tactttagca gccagggtga caactgagag gtgtcgaagc ttattcttct | 180 |
| gagcctctgt tagtggagga agattccggg cttcagctaa gtagtcagcg tatgtcccat | 240 |
| aagcaaacac tgtgagcagc cggaaggtag aggcaaagtc actctcagcc agctctctaa | 300 |
| cattgggcat gtccagcagt tctccaaaca cgtagacacc agnggcctcc agcacctgat | 360 |
| ggatgagtgt ggccagcgct gcccccttgg ccgacttggc taggagcaga aattgctcct | 420 |
| ggttctgccc tgtcaccttc acttccgcac tcatcactgc actgagtgtg ggggacttgg | 480 |
| gctcaggatg tccagagacg tggttccgcc ccctcnctta atgacaccgn ccanncaacc | 540 |
| gtcggctccc gccgantgng ttcgtcgtnc ctgggtcagg gtctgctggc cnctacttgc | 600 |

| | |
|---|---:|
| aancttcgtc nggcccatgg aattcaccnc accggaactn gtangatcca ctnnttctat | 660 |
| aaccggncgc caccgcnnnt ggaactccac tcttnttncc tttacttgag ggttaaggtc | 720 |
| acccttnncg ttaccttggt ccaaaccntn ccntgtgtcg anatngtnaa tcnggnccna | 780 |
| tnccanccnc atangaagcc ng | 802 |

<210> SEQ ID NO 19
<211> LENGTH: 731
<212> TYPE: DNA
<213> ORGANISM: Homo sapien
<220> FEATURE:
<221> NAME/KEY: misc_feature
<222> LOCATION: (1)...(731)
<223> OTHER INFORMATION: n = A,T,C or G

<400> SEQUENCE: 19

| | |
|---|---:|
| cnaagcttcc aggtnacggg ccgcnaancc tgacccnagg tancanaang cagncngcgg | 60 |
| gagcccaccg tcacgnggng ngtctttat nggagggggc ggagccacat cnctggacnt | 120 |
| cntgacccca actccccncc ncncantgca gtgatgagtg cagaactgaa ggtnacgtgg | 180 |
| caggaaccaa gancaaannc tgctccnntc caagtcggcn naggggggcgg ggctggccac | 240 |
| gcncatcent cnagtgctgn aaagccccnn cctgtctact tgtttggaga acngcnnnga | 300 |
| catgcccagn gttanataac nggcngagag tnantttgcc tctcccttcc ggctgcgcan | 360 |
| cgngtntgct tagnggacat aacctgacta cttaactgaa cccnngaatc tnccnccect | 420 |
| ccactaagct cagaacaaaa aacttcgaca ccactcantt gtcacctgnc tgctcaagta | 480 |
| aagtgtaccc catnccaat gtntgctnga ngctctgncc tgcnttangt tcggtcctgg | 540 |
| gaagacctat caattnaagc tatgtttctg actgcctctt gctccctgna caancnacc | 600 |
| cnncnntcca aggggggnc ggccccaat cccccaacc ntnaattnan tttanccccn | 660 |
| cccccnggcc cggccttta cnancntcnn nnacngggna aaaccnnngc tttncccaac | 720 |
| nnaatccncc t | 731 |

<210> SEQ ID NO 20
<211> LENGTH: 754
<212> TYPE: DNA
<213> ORGANISM: Homo sapien
<220> FEATURE:
<221> NAME/KEY: misc_feature
<222> LOCATION: (1)...(754)
<223> OTHER INFORMATION: n = A,T,C or G

<400> SEQUENCE: 20

| | |
|---|---:|
| tttttttttt ttttttttt taaaaacccc ctccattnaa tgnaaacttc cgaaattgtc | 60 |
| caaccccctc ntccaaatnn ccntttccgg gnggggttc caaacccaan ttannttgg | 120 |
| annttaaatt aaatnttnnt tggnggnnna anccnaatgt nangaaagtt naacccanta | 180 |
| tnancttnaa tncctggaaa ccngtngntt ccaaaaatnt ttaaccctta antccctccg | 240 |
| aaatngttna nggaaaaccc aanttctcnt aaggttgttt gaaggntnaa tnaaaanccc | 300 |
| nnccaattgt ttttngccac gcctgaatta attggnttcc gntgttttcc nttaaaanaa | 360 |
| ggnnanccc ggttantnaa tccccccnnc cccaattata ccganttttt ttngaattgg | 420 |
| ganccccncgg gaattaacgg ggnnnntccc tnttgggggg cnggnccccc ccncntcggg | 480 |
| ggttnggnc aggncnnaat tgtttaaggg tccgaaaaat ccctccnaga aaaaaanctc | 540 |
| ccaggntgag nntngggttt ncccccccc canggcccct ctcgnanagt tgggggttgg | 600 |
| ggggcctggg attttntttc ccctnttncc tcccccccc ccnggganag aggttngngt | 660 |

-continued

```
tttgntcnnc ggccccnccn aagancttttn ccganttnan ttaaatccnt gcctnggcga      720
agtccnttgn agggntaaan ggcccccctnn cggg                                  754
```

<210> SEQ ID NO 21
<211> LENGTH: 755
<212> TYPE: DNA
<213> ORGANISM: Homo sapien
<220> FEATURE:
<221> NAME/KEY: misc_feature
<222> LOCATION: (1)...(755)
<223> OTHER INFORMATION: n = A,T,C or G

<400> SEQUENCE: 21

```
atcancccat gaccccnaac nngggaccnc tcanccggnc nnncnaccnc cggccnatca        60
nngtnagnnc actncnnttn natcacnccc cnccnactac gcccncnanc cnacgcncta       120
nncanatncc actgannqcg cgangtngan ngagaaanct nataccanag ncaccanacn       180
ccagctgtcc nanaangcct nnnatacngg nnnatccaat ntgnanccte cnaagtattn       240 nncnncanat gattttcctn anccgattac ccntnccccc tanccctcc cccccaacna        300 cgaaggcnct ggccnaagg nngcgncncc ccgctagntc cccnncaagt cncncncta        360 aactcanccn nattacncgc ttcntgagta tcactccccg aatctcaccc tactcaactc      420
aaaaanatcn gatacaaaat aatncaagcc tgnttatnac actntgactg ggtctctatt     480
ttagnggtcc ntnaancntc ctaatacttc cagtctncct tcnccaattt ccnaanggct     540
ctttcngaca gcatnttttg gttcccnntt gggttcttan ngaattgccc ttcntngaac     600
gggctcntct tttccttcgg ttanccctggn ttcnnccggc cagttattat ttcccnttt     660 aaattcntnc cntttantttt tggcnttcna aaccccggc cttgaaaacg gcccccctggt    720 aaaaggttgt tttganaaaa ttttttgtttt gttcc                                755
```

<210> SEQ ID NO 22
<211> LENGTH: 849
<212> TYPE: DNA
<213> ORGANISM: Homo sapien
<220> FEATURE:
<221> NAME/KEY: misc_feature
<222> LOCATION: (1)...(849)
<223> OTHER INFORMATION: n = A,T,C or G

<400> SEQUENCE: 22

```
tttttttttt tttttangtg tngtcgtgca ggtagaggct tactacaant gtgaanacgt       60
acgctnggan taangcgacc cganttctag gannncnccct aaaatcanac tgtgaagatn     120
atcctgnnna cggaagggtc accggnngat nntgctaggg tgnccnctcc cannncnttn      180
cataactcng nggccctgcc caccaccttc ggcggcccng ngccgggcc cgggtcattn       240 gnnttaaccn cactnngcna ncggtttccn ncccnncng acccnggcga tccggggtnc       300
tctgtcttcc cctgnagncn anaaantggg ccncggnccc ctttaccccct nnacaagcca    360 cngccntcta nccncngccc ccctccant nngggggact gccnanngct ccgttnctng      420 nnacccnccnn gggtnctcg gttgtcgant cnaccgnang ccanggattc cnaaggaagg    480
tgcgttnttg gccccctaccc ttcgctncgg nncacccttc ccgacnanga nccgctcccg    540
cncnncgnng cctcncctcg caacaccgc nctcntcngt ncggnnnccc ccccacccgc    600
nccctcncnc ngncgnancn ctccnccncc gtctcannca ccaccccgcc ccgccaggcc     660
ntcanccacn ggnngacnng nagcncnntc gcnccgcgcn cgncnccct cgccncngaa     720 ctncntcngg ccantnncgc tcaanccnna cnaaacgccg ctgcgcggcc cgnagcgncc    780
```

| | |
|---|---|
| ncctccncga gtcctcccgn cttccnaccc angnnttccn cgaggacacn nnaccccgcc | 840 |
| nncangcgg | 849 |

<210> SEQ ID NO 23
<211> LENGTH: 872
<212> TYPE: DNA
<213> ORGANISM: Homo sapien
<220> FEATURE:
<221> NAME/KEY: misc_feature
<222> LOCATION: (1)...(872)
<223> OTHER INFORMATION: n = A,T,C or G

<400> SEQUENCE: 23

| | |
|---|---|
| gcgcaaacta tacttcgctc gnactcgtgc gcctcgctnc tcttttcctc cgcaaccatg | 60 |
| tctgacnanc ccgattnggc ngatatcnan aagntcganc agtccaaact gantaacaca | 120 |
| cacacncnan aganaaatcc nctgccttcc anagtanacn attgaacnng agaaccangc | 180 |
| nggcgaatcg taatnaggcg tgcgccgcca atntgtcncc gtttattntn ccagntcnc | 240 |
| ctnccnaccc tacntcttcn nagctgtcnn accctngtn cgnaccccc naggtcggga | 300 |
| tcgggttttnn nntgaccgng cnnccctcc ccccntccat nacgancnc ccgcaccacc | 360 |
| nanngcncgc nccccgnnct cttcgccncc ctgtcctntn ccctgtngc ctggcncngn | 420 |
| accgcattga ccctcgccnn ctncnngaaa ncgnanacgt ccgggttgnn annancgctg | 480 |
| tgggnnngcg tctgcnccgc gttccttccn ncnncttcca ccatcttcnt tacngggtct | 540 |
| ccncgccntc tcnnncacnc cctgggacgc tntcctntgc cccccttac tccccccctt | 600 |
| cgncgtgncc cgnccccacc ntcatttnca nacgntcttc acaannncct ggntnnctcc | 660 |
| cnancgncn gtcanccnag ggaaggggng ggnnccnntg nttgacgttg nggngangtc | 720 |
| cgaanantcc tcnccntcan cnctacccct cgggcgnnct ctcngttncc aacttancaa | 780 |
| ntctcccccg ngngcncntc tcagcctcnc ccnccccnct ctctgcantg tnctctgctc | 840 |
| tnaccnntac gantnttcgn cnccctcttt cc | 872 |

<210> SEQ ID NO 24
<211> LENGTH: 815
<212> TYPE: DNA
<213> ORGANISM: Homo sapien
<220> FEATURE:
<221> NAME/KEY: misc_feature
<222> LOCATION: (1)...(815)
<223> OTHER INFORMATION: n = A,T,C or G

<400> SEQUENCE: 24

| | |
|---|---|
| gcatgcaagc ttgagtattc tatagngtca cctaaatanc ttggcntaat catggtcnta | 60 |
| nctgncttcc tgtgtcaaat gtatacnaan tanatatgaa tctnatntga caagannnta | 120 |
| tcntncatta gtaacaantg tnntgtccat cctgtcngan canattccca tnnattncgn | 180 |
| cgcattcncn gcncantatn taatngggaa ntcnnntnnn ncaccnncat ctatcntncc | 240 |
| gcncccctgac tggnagagat ggatnanttc tnntntgacc nacatgttca tcttggattn | 300 |
| aananccccc cgcngnccac cggttngnng cnagccnntc ccaagacctc ctgtggaggt | 360 |
| aacctgcgtc aganncatca aacntgggaa acccgcnncc angtnnaagt ngnnncanan | 420 |
| gatcccgtcc aggnttnacc atcccttcnc agcgccccct ttngtgcctt anagngnagc | 480 |
| gtgtccnanc cnctcaacat ganacgcgcc agnccanccg caattnggca caatgtcgnc | 540 |
| gaaccccta gggggantna tncaaancc caggattgtc cncncangaa atcccncanc | 600 |
| cccnccctac ccnnctttgg gacngtgacc aantcccgga gtnccagtcc ggccngnctc | 660 |

-continued

| | |
|---|---|
| ccccaccggt nnccntgggg gggtgaanct cngnntcanc cngncgaggn ntcgnaagga | 720 |
| accggnccth ggncgaanng ancnntcnga agngccncnt cgtataaccc ccctcncca | 780 |
| nccnacngnt agntcccccc cngggtncgg aangg | 815 |

<210> SEQ ID NO 25
<211> LENGTH: 775
<212> TYPE: DNA
<213> ORGANISM: Homo sapien
<220> FEATURE:
<221> NAME/KEY: misc_feature
<222> LOCATION: (1)...(775)
<223> OTHER INFORMATION: n = A,T,C or G

<400> SEQUENCE: 25

| | |
|---|---|
| ccgagatgtc tcgctccgtg gccttagctg tgctcgcgct actctctctt tctggcctgg | 60 |
| aggctatcca gcgtactcca aagattcagg tttactcacg tcatccagca gagaatggaa | 120 |
| agtcaaattt cctgaattgc tatgtgtctg ggtttcatcc atccgacatt gaanttgact | 180 |
| tactgaagaa tgganagaga attgaaaaag tggagcattc agacttgtct ttcagcaagg | 240 |
| actggtcttt ctatctcntg tactacactg aattcacccc cactgaaaaa gatgagtatg | 300 |
| cctgccgtgt gaaccatgtg actttgtcac agcccaagat agttaagtgg gatcgagaca | 360 |
| tgtaagcagn cnncatggaa gtttgaagat gccgcatttg gattggatga attccaaatt | 420 |
| ctgcttgctt gcnttttaat antgatatgc ntatacaccc tacccttat gnccccaaat | 480 |
| tgtaggggtt acatnantgt tcncntngga catgatcttc ctttataant ccnccnttcg | 540 |
| aattgcccgt cncccngttn ngaatgtttc cnnaaccacg gttggctccc ccaggtcncc | 600 |
| tcttacggaa gggcctgggc cnctttcaa ggttggggga accnaaaatt tcncttntgc | 660 |
| ccncccncca cnntcttgng nncncanttt ggaacccttc cnattcccct tggcctcnna | 720 |
| nccttnncta anaaaacttn aaancgtngc naaannttn acttcccccc ttacc | 775 |

<210> SEQ ID NO 26
<211> LENGTH: 820
<212> TYPE: DNA
<213> ORGANISM: Homo sapien
<220> FEATURE:
<221> NAME/KEY: misc_feature
<222> LOCATION: (1)...(820)
<223> OTHER INFORMATION: n = A,T,C or G

<400> SEQUENCE: 26

| | |
|---|---|
| anattantac agtgtaatct tttcccagag gtgtgtanag ggaacggggc ctagaggcat | 60 |
| cccanagata ncttatanca acagtgcttt gaccaagagc tgctgggcac atttcctgca | 120 |
| gaaaaggtgg cggtccccat cactcctcct ctcccatagc catcccagag gggtgagtag | 180 |
| ccatcangcc ttcggtggga gggagtcang gaaacaacan accacagagc anacagacca | 240 |
| ntgatgacca tgggcgggag cgagcctctt ccctgnaccg gggtggcana nganagccta | 300 |
| nctgaggggt cacactataa acgttaacga ccnagatnan cacctgcttc aagtgcaccc | 360 |
| ttcctacctg acnaccagng accnnnaact gcngcctggg dacagcnctg ggancagcta | 420 |
| acnnagcact cacctgcccc ccatggccg tncgcntccc tggtcctgnc aagggaagct | 480 |
| ccctgttgga attncgggga naccaaggga ncccctcct ccanctgtga aggaaaaann | 540 |
| gatggaattt tnccccttccg gccnntcccc tcttccttta cacgcccct nntactcntc | 600 |
| tccctctntt ntcctgncnc acttttnacc ccnnnatttc ccttnattga tcggannctn | 660 |
| ganattccac tnncgcctnc cntcnatcng naanacnaaa nactntctna cccngggat | 720 |

| | |
|---|---:|
| gggnncctcg ntcatcctct cttttttcnct accnccnnttt ctttgcctct ccttngatca | 780 |
| tccaaccntc gntggccntn cccccccnnn tcctttnccc | 820 |

<210> SEQ ID NO 27
<211> LENGTH: 818
<212> TYPE: DNA
<213> ORGANISM: Homo sapien
<220> FEATURE:
<221> NAME/KEY: misc_feature
<222> LOCATION: (1)...(818)
<223> OTHER INFORMATION: n = A,T,C or G

<400> SEQUENCE: 27

| | |
|---|---:|
| tctggtgat ggcctcttcc tcctcaggga cctctgactg ctctgggcca aagaatctct | 60 |
| tgtttcttct ccgagcccca ggcagcggtg attcagccct gcccaacctg attctgatga | 120 |
| ctgcggatgc tgtgacggac ccaaggggca aatagggtcc caggtccag ggaggggcgc | 180 |
| ctgctgagca cttccgcccc tcaccctgcc cagcccctgc catgagctct gggctgggtc | 240 |
| tccgcctcca gggttctgct cttccangca ngccancaag tggcgctggg ccacactggc | 300 |
| ttcttcctgc cccntccctg gctctgantc tctgtcttcc tgtcctgtgc angcnccttg | 360 |
| gatctcagtt tccctcnctc anngaactct gtttctgann tcttcantta actntganttt | 420 |
| tatnaccnan tggnctgtnc tgtcnnactt taatgggccn gaccggctaa tccctccctc | 480 |
| nctcccttcc anttcnnnna accngcttnc cntcntctcc ccntancccg ccngggaanc | 540 |
| ctcctttgcc ctnaccangg gccnnnaccg cccntnnctn gggggcnng gtnnctncnc | 600 |
| ctgntnnccc cnctcncnnt tncctcgtcc cnncnncgcn nngcannttc ncgtcccnn | 660 |
| tnnctcttcn ngtntcgnaa ngtcncntn tnnnnngncn ngtnnntncn tccctctcnc | 720 |
| cnnntgnang tnnttnnnnc ncngnncccc nnnncnnnnn nggnnntnnn tctncncngc | 780 |
| cccnnccccc ngnattaagg cctccnntct ccggccnc | 818 |

<210> SEQ ID NO 28
<211> LENGTH: 731
<212> TYPE: DNA
<213> ORGANISM: Homo sapien
<220> FEATURE:
<221> NAME/KEY: misc_feature
<222> LOCATION: (1)...(731)
<223> OTHER INFORMATION: n = A,T,C or G

<400> SEQUENCE: 28

| | |
|---|---:|
| aggaagggcg gagggatatt gtangggatt gagggatagg agnataangg gggaggtgtg | 60 |
| tcccaacatg anggtgnngt tctcttttga angaggggttg ngtttttann ccnggtgggt | 120 |
| gattnaaccc cattgtatgg agnnaaaggn tttnagggat ttttcggctc ttatcagtat | 180 |
| ntanattcct gtnaatcgga aaatnatntt tcnncnggaa aatnttgctc ccatccgnaa | 240 |
| attnctcccg ggtagtgcat nttnggggn cngccangtt tcccaggctg ctanaatcgt | 300 |
| actaaagntt naagtgggan tncaaatgaa aacctnncac agagnatccn tacccgactg | 360 |
| tnnnttncct tcgccctntg actctgcnng agcccaatac ccnngngnat gtcncccngn | 420 |
| nnngcgncnc tgaaannnnc tcgnggctnn gancatcang gggtttcgca tcaaaagcnn | 480 |
| cgtttcncat naaggcactt tngcctcatc caaccnctng ccctcnncca tttgccgtc | 540 |
| nggttcncct acgctnnctng cncctnnntn ganattttnc ccgcctnggg naaccctcct | 600 |
| gnaatgggta gggncttntc ttttnaccnn gnggtntact aatcnnсctnc acgcntnctt | 660 |

| | |
|---|---|
| tctcnacccc cccccttttt caatcccanc ggcnaatggg gtctccccnn cganggggggg | 720 |
| nnncccannc c | 731 |

<210> SEQ ID NO 29
<211> LENGTH: 822
<212> TYPE: DNA
<213> ORGANISM: Homo sapien
<220> FEATURE:
<221> NAME/KEY: misc_feature
<222> LOCATION: (1)...(822)
<223> OTHER INFORMATION: n = A,T,C or G

<400> SEQUENCE: 29

| | |
|---|---|
| actagtccag tgtggtggaa ttccattgtg ttggggncnc ttctatgant antnttagat | 60 |
| cgctcanacc tcacanccctc ccnacnangc ctataangaa nannaataga nctgtncnnt | 120 |
| atntntacnc tcatanncct cnnnacccac tccctcttaa cccntactgt gcctatngcn | 180 |
| tnnctantct ntgccgcctn cnanccaccn gtgggccnac cncnngnatt ctcnatctcc | 240 |
| tcnccatntn gcctananta ngtncatacc ctatacctac nccaatgcta nnnctaancn | 300 |
| tccatnantt annntaacta ccactgacnt ngactttcnc atnanctcct aatttgaatc | 360 |
| tactctgact cccacngcct annnattagc ancntccccc nacnatntct caaccaaatc | 420 |
| ntcaacaacc tatctanctg ttcnccaacc nttncctccg atccccnnac aaccccccctc | 480 |
| ccaaatacccc nccacctgac ncctaacccn caccatcccg gcaagccnan ggncatttan | 540 |
| ccactggaat cacnatngga naaaaaaaac ccnaactctc tancncnnat ctccctaana | 600 |
| aatnctcctn naatttactn ncantnccat caanccccacn tgaaacnnaa ccctgttttt | 660 |
| tanatcccctt ctttcgaaaa ccnacccttt annncccaac ctttngggcc ccccncctnc | 720 |
| ccnaatgaag gncncccaat cnangaaacg nccntgaaaa ancnaggcna anannntccg | 780 |
| canatcctat cccttanttn ggggnccctt ncccngggcc cc | 822 |

<210> SEQ ID NO 30
<211> LENGTH: 787
<212> TYPE: DNA
<213> ORGANISM: Homo sapien
<220> FEATURE:
<221> NAME/KEY: misc_feature
<222> LOCATION: (1)...(787)
<223> OTHER INFORMATION: n = A,T,C or G

<400> SEQUENCE: 30

| | |
|---|---|
| cggccgcctg ctctggcaca tgcctcctga atggcatcaa aagtgatgga ctgcccattg | 60 |
| ctagagaaga ccttctctcc tactgtcatt atggagccct gcagactgag ggctcccctt | 120 |
| gtctgcagga tttgatgtct gaagtcgtgg agtgtggctt ggagctcctc atctacatna | 180 |
| gctggaagcc ctggagggcc tctctcgcca gcctcccccct tctctccacg ctctccangg | 240 |
| acaccagggg ctccaggcag cccattattc ccagnangac atggtgtttc tccacgcgga | 300 |
| cccatggggc ctgnaaggcc agggtctcct ttgacaccat ctctcccgtc ctgcctggca | 360 |
| ggccgtggga tccactantt ctanaacggn cgccaccncg gtgggagctc cagcttttgt | 420 |
| tcccnttaat gaaggttaat tgcncgcttg gcgtaatcat nggtcanaac tntttcctgt | 480 |
| gtgaaattgt ttntccccctc ncnattccnc ncnacatacn aacccggaan cataaagtgt | 540 |
| taaagcctgg gggtngccctn nngaatnaac tnaactcaat taattgcgtt ggctcatggc | 600 |
| ccgctttccn ttcnggaaaa ctgtcntccc ctgcnttnnt gaatcggcca cccccccggg | 660 |
| aaaagcggtt tgcnttttng ggggntcctt ccncttcccc cctcnctaan ccctncgcct | 720 |

| | |
|---|---|
| cggtcgttnc nggtngcggg gaangggnat nnnctcccnc naaggggng agnnngntat | 780 |
| ccccaaa | 787 |

<210> SEQ ID NO 31
<211> LENGTH: 799
<212> TYPE: DNA
<213> ORGANISM: Homo sapien
<220> FEATURE:
<221> NAME/KEY: misc_feature
<222> LOCATION: (1)...(799)
<223> OTHER INFORMATION: n = A,T,C or G

<400> SEQUENCE: 31

| | |
|---|---|
| tttttttttt tttttttggc gatgctactg tttaattgca ggaggtgggg gtgtgtgtac | 60 |
| catgtaccag ggctattaga agcaagaagg aaggagggag ggcagagcgc cctgctgagc | 120 |
| aacaaaggac tcctgcagcc ttctctgtct gtctcttggc gcaggcacat ggggaggcct | 180 |
| cccgcagggt gggggccacc agtccagggg tgggagcact acanggggtg ggagtgggtg | 240 |
| gtggctggtn cnaatggcct gncacanatc cctacgattc ttgacacctg gatttcacca | 300 |
| ggggaccttc tgttctccca nggnaacttc ntnnatctcn aaagaacaca actgtttctt | 360 |
| cngcanttct ggctgttcat ggaaagcaca ggtgtccnat ttnggctggg acttggtaca | 420 |
| tatggttccg gcccacctct cccntcnaan aagtaattca ccccccccn cntctnttg | 480 |
| cctgggccct taantaccca caccggaact canttantta ttcatcttng gntgggcttg | 540 |
| ntnatcnccn cctgaagcg ccaagttgaa aggccacgcc gtncccntc cccatagnan | 600 |
| nttttnncnt canctaatgc ccccccnggc aacnatccaa tccccccccn tggggcccc | 660 |
| agcccanggc ccccgnctcg ggnnccngn cncgnantcc ccaggntctc ccantcngnc | 720 |
| ccnnngcncc cccgcacgca gaacanaagg ntgagccnc cgcannnnnn nggtnncnac | 780 |
| ctcgccccc ccnncgnng | 799 |

<210> SEQ ID NO 32
<211> LENGTH: 789
<212> TYPE: DNA
<213> ORGANISM: Homo sapien
<220> FEATURE:
<221> NAME/KEY: misc_feature
<222> LOCATION: (1)...(789)
<223> OTHER INFORMATION: n = A,T,C or G

<400> SEQUENCE: 32

| | |
|---|---|
| tttttttttt tttttttttt tttttttttt tttttttttt tttttttttt tttttttttt | 60 |
| ttttnccnag ggcaggttta ttgacaacct cncgggacac aancaggctg gggacaggac | 120 |
| ggcaacaggc tccggcggcg gcggcggcgg ccctacctgc ggtaccaaat ntgcagcctc | 180 |
| cgctcccgct tgatnttcct ctgcagctgc aggatgcnt aaaacagggc ctcggccntn | 240 |
| ggtgggcacc ctgggatttn aatttccacg ggcacaatgc ggtcgcancc cctcaccacc | 300 |
| nattaggaat agtggtntta cccncncg ttggcncact cccntggaa accacttntc | 360 |
| gcggctccgg catctggtct taaaccttgc aaacnctggg gccctctttt tggttantnt | 420 |
| nccngccaca atcatnactc agactggcnc gggctggccc caaaaaancn ccccaaaacc | 480 |
| ggnccatgtc ttnncggggt tgctgcnatn tncatcacct cccgggcnca ncaggncaac | 540 |
| ccaaaagttc ttgngggccn caaaaaanct ccgggggnc ccagtttcaa caaagtcatc | 600 |
| cccccttggcc cccaaatcct cccccgntt nctgggtttg ggaacccacg cctctnnctt | 660 |
| tggnnggcaa gntggntccc ccttcgggcc cccggtgggc ccnnctctaa ngaaaacncc | 720 |

```
ntcctnnnca ccatccccc nngnnacgnc tancaangna tcccttttt tanaaacggg      780 cccccncg                                                             789
```

<210> SEQ ID NO 33
<211> LENGTH: 793
<212> TYPE: DNA
<213> ORGANISM: Homo sapien
<220> FEATURE:
<221> NAME/KEY: misc_feature
<222> LOCATION: (1)...(793)
<223> OTHER INFORMATION: n = A,T,C or G

<400> SEQUENCE: 33

```
gacagaacat gttggatggt ggagcacctt tctatacgac ttacaggaca gcagatgggg      60
aattcatggc tgttggagca atanaacccc agttctacga gctgctgatc aaaggacttg     120
gactaaagtc tgatgaactt cccaatcaga tgagcatgga tgattggcca gaaatgaana    180
agaagtttgc agatgtattt gcaaagaaga cgaaggcaga gtggtgtcaa atctttgacg    240
gcacagatgc ctgtgtgact ccggttctga cttttgagga ggttgttcat catgatcaca    300
acaangaacg gggctcgttt atcaccantg aggagcagga cgtgagcccc cgccctgcac    360
ctctgctgtt aaacaccca gccatccctt ctttcaaaag ggatccacta cttctagagc     420
ggncgccacc gcggtggagc tccagctttt gttcccttta gtgagggtta attgcgcgct    480
tggcgtaatc atggtcatan ctgtttcctg tgtgaaattg ttatccgctc acaattccac    540
acaacatacg anccggaagc atnaaatttt aaagcctggn ggtngcctaa tgantgaact    600
nactcacatt aattggcttt gcgctcactg cccgctttcc agtccggaaa acctgtcctt    660
gccagctgcc nttaatgaat cnggccaccc cccggggaaa aggcngtttg cttnttgggg    720
cgcncttccc gctttctcgc ttcctgaant ccttccccc ggtctttcgg cttgcggcna    780
acggtatcna cct                                                      793
```

<210> SEQ ID NO 34
<211> LENGTH: 756
<212> TYPE: DNA
<213> ORGANISM: Homo sapien
<220> FEATURE:
<221> NAME/KEY: misc_feature
<222> LOCATION: (1)...(756)
<223> OTHER INFORMATION: n = A,T,C or G

<400> SEQUENCE: 34

```
gccgcgaccg gcatgtacga gcaactcaag ggcgagtgga accgtaaaag ccccaatctt     60
ancaagtgcg gggaanagct gggtcgactc aagctagttc ttctggagct caacttcttg   120
ccaaccacag ggaccaagct gaccaaacag cagctaattc tggcccgtga catactggag   180 atcgggccc aatggagcat cctacgcaan gacatcccct ccttgagcg ctacatggcc    240 cagctcaaat gctactactt tgattacaan gagcagctcc ccgagtcagc ctatatgcac   300
cagctcttgg gcctcaacct cctcttcctg ctgtcccaga accgggtggc tgantnccac   360
acgganttgg ancggctgcc tgcccaanga catacanacc aatgtctaca tcnaccacca   420
gtgtcctgga gcaatactga tgganggcag ctaccncaaa gtnttcctgg ccnagggtaa   480 catccccgc cgagagctac accttcttca ttgacatcct gctcgacact atcagggatg    540
aaaatcgcng ggttgctcca gaaaggctnc aanaanatcc ttttcnctga aggccccgg    600 atncnctagt nctagaatcg gccgccatc gcggtggganc ctccaacctt tcgttnccct   660
```

| | |
|---|---|
| ttactgaggg ttnattgccg cccttggcgt tatcatggtc acnccngttn cctgtgttga | 720 |
| aattnttaac cccccacaat tccacgccna cattng | 756 |

<210> SEQ ID NO 35
<211> LENGTH: 834
<212> TYPE: DNA
<213> ORGANISM: Homo sapien
<220> FEATURE:
<221> NAME/KEY: misc_feature
<222> LOCATION: (1)...(834)
<223> OTHER INFORMATION: n = A,T,C or G

<400> SEQUENCE: 35

| | |
|---|---|
| ggggatctct anatcnacct gnatgcatgg ttgtcggtgt ggtcgctgtc gatgaanatg | 60 |
| aacaggatct tgcccttgaa gctctcggct gctgtnttta agttgctcag tctgccgtca | 120 |
| tagtcagaca cnctcttggg caaaaaacan caggatntga gtcttgattt cacctccaat | 180 |
| aatcttcngg gctgtctgct cggtgaactc gatgacnang ggcagctggt tgtgtntgat | 240 |
| aaantccanc angttctcct tggtgacctc cccttcaaag ttgttccggc cttcatcaaa | 300 |
| cttctnnaan angannancc canctttgtc gagctggnat ttgganaaca cgtcactgtt | 360 |
| ggaaactgat cccaaatggt atgtcatcca tcgcctctgc tgcctgcaaa aaacttgctt | 420 |
| ggcncaaatc cgactccccn tccttgaaag aagccnatca cacccccctc cctggactcc | 480 |
| nncaangact ctnccgctnc cccntccnng cagggttggt ggcanncgg gccntgcgc | 540 |
| ttcttcagcc agttcacnat nttcatcagc ccctctgcca gctgttntat tccttggggg | 600 |
| ggaanccgtc tctcccttcc tgaannaact ttgaccgtng aatagccgc gcntcnccnt | 660 |
| acntnctggg ccgggttcaa antccctccn ttgncnntcn cctcgggcca ttctggattt | 720 |
| nccnaacttt ttccttcccc cnccccncgg ngtttggntt tttcatnggg ccccaactct | 780 |
| gctnttggcc antccctgg gggcntntan cnccccctnt ggtcccntng ggcc | 834 |

<210> SEQ ID NO 36
<211> LENGTH: 814
<212> TYPE: DNA
<213> ORGANISM: Homo sapien
<220> FEATURE:
<221> NAME/KEY: misc_feature
<222> LOCATION: (1)...(814)
<223> OTHER INFORMATION: n = A,T,C or G

<400> SEQUENCE: 36

| | |
|---|---|
| cggncgcttt ccngccgcgc cccgtttcca tgacnaaggc tcccttcang ttaaatacnn | 60 |
| cctagnaaac attaatgggt tgctctacta atacatcata cnaaccagta agcctgccca | 120 |
| naacgccaac tcaggccatt cctaccaaag gaagaaaggc tggtctctcc accccctgta | 180 |
| ggaaaggcct gccttgtaag acaccacaat ncggctgaat ctnaagtctt gtgttttact | 240 |
| aatgaaaaaa aaaataaac aanaggtttt gttctcatgg ctgcccaccg cagcctggca | 300 |
| ctaaaacanc ccagcgctca cttctgcttg ganaaatatt ctttgctctt ttggacatca | 360 |
| ggcttgatgg tatcactgcc acntttccac ccagctgggc nccctteccc catntttgtc | 420 |
| antganctgg aaggcctgaa ncttagtctc caaaagtctc ngcccacaag accggccacc | 480 |
| aggggangtc ntttncagtg gatctgccaa anantacccn tatcatcnnt gaataaaaag | 540 |
| gccctgaac ganatgcttc cancanccll taagacccat aatcctngaa ccatggtgcc | 600 |
| cttccggtct gatccnaaag gaatgttcct gggtcccant ccctcctttg ttncttacgt | 660 |
| tgtntttggac ccntgctngn atnacccaan tganatcccc ngaagcaccc tncccctggc | 720 |

-continued

```
atttganttt cntaaattct ctgccctacn nctgaaagca cnattccctn ggcnccnaan    780
ggngaactca agaaggtctn ngaaaaacca cncn                                814
```

<210> SEQ ID NO 37
<211> LENGTH: 760
<212> TYPE: DNA
<213> ORGANISM: Homo sapien
<220> FEATURE:
<221> NAME/KEY: misc_feature
<222> LOCATION: (1)...(760)
<223> OTHER INFORMATION: n = A,T,C or G

<400> SEQUENCE: 37

```
gcatgctgct cttcctcaaa gttgttcttg ttgccataac aaccaccata ggtaaagcgg     60
gcgcagtgtt cgctgaaggg gttgtagtac cagcgcggga tgctctcctt gcagagtcct    120
gtgtctggca ggtccacgca atgccctttg tcactgggga aatggatgcg ctggagctcg    180
tcnaanccac tcgtgtattt ttcacangca gcctcctccg aagcntccgg gcagttgggg    240
gtgtcgtcac actccactaa actgtcgatn cancagccca ttgctgcagc ggaactgggt    300
gggctgacag gtgccagaac acactggatn ggcctttcca tggaagggcc tgggggaaat    360 cnccctnancc caaactgcct ctcaaaggcc accttgcaca ccccgacagg ctagaaatgc    420
actcttcttc ccaaaggtag ttgttcttgt tgcccaagca ncctccanca aaccaaaanc    480
ttgcaaaatc tgctccgtgg gggtcatnnn taccanggtt ggggaaanaa acccggcngn    540
ganccncctt gtttgaatgc naaggnaata atcctcctgt cttgcttggg tggaanagca    600
caattgaact gttaacnttg ggccgngttc cnctngggtg gtctgaaact aatcaccgtc    660
actggaaaaa ggtangtgcc ttccttgaat tcccaaantt cccctngntt tgggtnnttt    720
ctcctctncc ctaaaaatcg tnttcccccc ccntanggcg                          760
```

<210> SEQ ID NO 38
<211> LENGTH: 724
<212> TYPE: DNA
<213> ORGANISM: Homo sapien
<220> FEATURE:
<221> NAME/KEY: misc_feature
<222> LOCATION: (1)...(724)
<223> OTHER INFORMATION: n = A,T,C or G

<400> SEQUENCE: 38

```
tttttttttt tttttttttt tttttttttt ttttttaaaaa ccccctccat tgaatgaaaa    60
cttccnaaat tgtccaaccc cctcnnccaa atnnccattt ccgggggggg gttccaaacc    120
caaattaatt ttgganttta aattaaatnt tnattngggg aanaanccaa atgtnaagaa    180
aatttaaccc attataaact taaatnccctn gaaaccnctg gnttccaaaa attttttaacc    240 cttaaatccc tccgaaattg ntaanggaaa accaaattcn cctaaggctn tttgaaggtt    300
ngatttaaac ccccttnant tntttttnacc cnngnctnaa ntatttngnt tccggtgttt    360
tcctnttaan cntnggtaac tcccgntaat gaannnccct aanccaatta aaccgaattt    420
tttttgaatt ggaaattccn ngggaattna ccggggtttt tcccntttgg gggccatncc    480
cccnctttcg gggtttgggn ntaggttgaa tttttnnang nccaaaaaaa nccccaaana    540
aaaaaactcc caagnnttaa ttngaatntc cccttccca ggccttttgg gaaggngggg    600
tttntggggg ccngggantt cnttcccccn ttnccnccc ccccccnggt aaanggttat    660
ngnntttggt ttttgggccc cttnanggac cttccggatn gaaattaaat ccccgggncg    720
gccg                                                                 724
```

<210> SEQ ID NO 39
<211> LENGTH: 751
<212> TYPE: DNA
<213> ORGANISM: Homo sapien
<220> FEATURE:
<221> NAME/KEY: misc_feature
<222> LOCATION: (1)...(751)
<223> OTHER INFORMATION: n = A,T,C or G

<400> SEQUENCE: 39

| | | | | | |
|---|---|---|---|---|---|
| ttttttttttt | tttttctttg | ctcacattta | atttttattt | tgattttttt | taatgctgca | 60 |
| caacacaata | tttatttcat | ttgtttcttt | tatttcattt | tatttgtttg | ctgctgctgt | 120 |
| tttatttatt | tttactgaaa | gtgagaggga | acttttgtgg | ccttttttcc | ttttttctgta | 180 |
| ggccgcctta | agctttctaa | atttggaaca | tctaagcaag | ctgaaggaa | aaggggttt | 240 |
| cgcaaaatca | ctcgggggaa | nggaaaggtt | gctttgttaa | tcatgccta | tggtgggtga | 300 |
| ttaactgctt | gtacaattac | ntttcacttt | taattaattg | tgctnaangc | tttaattana | 360 |
| cttgggggtt | ccctccccan | accaaccccn | ctgacaaaaa | gtgccngccc | tcaaatnatg | 420 |
| tcccggcnnt | cnttgaaaca | cacngcngaa | ngttctcatt | ntccccncnc | caggtnaaaa | 480 |
| tgaagggtta | ccatntttaa | cnccacctcc | acntggcnnn | gcctgaatcc | tcnaaaancn | 540 |
| ccctcaancn | aattnctnng | ccccggtcnc | gcntnngtcc | cnccccgggct | ccgggaantn | 600 |
| caccccccnga | anncnntnnc | naacnaaatt | ccgaaaatat | tcccnntcnc | tcaattcccc | 660 |
| cnnagactnt | cctcnncnan | cncaattttc | ttttnntcac | gaacncgnnc | cnnaaaatgn | 720 |
| nnnncnnctc | cnctngtccn | naatcnccan | c | | | 751 |

<210> SEQ ID NO 40
<211> LENGTH: 753
<212> TYPE: DNA
<213> ORGANISM: Homo sapien
<220> FEATURE:
<221> NAME/KEY: misc_feature
<222> LOCATION: (1)...(753)
<223> OTHER INFORMATION: n = A,T,C or G

<400> SEQUENCE: 40

| | | | | | |
|---|---|---|---|---|---|
| gtggtattt | ctgtaagatc | aggtgttcct | ccctcgtagg | tttagaggaa | acaccctcat | 60 |
| agatgaaaac | ccccccgaga | cagcagcact | gcaactgcca | agcagccggg | gtaggagggg | 120 |
| cgccctatgc | acagctgggc | ccttgagaca | gcagggcttc | gatgtcaggc | tcgatgtcaa | 180 |
| tggtctggaa | gcggcggctg | tacctgcgta | ggggcacacc | gtcagggccc | accaggaact | 240 |
| tctcaaagtt | ccaggcaacn | tcgttgcgac | acaccggaga | ccaggtgatn | agcttggggt | 300 |
| cggtcataan | cgcggtggcg | tcgtcgctgg | gagctggcag | ggcctcccgc | aggaaggcna | 360 |
| ataaaaggtg | cgcccccgca | ccgttcanct | cgcacttctc | naanaccatg | angttgggct | 420 |
| cnaacccacc | accanncccgg | acttccttga | nggaattccc | aaatctcttc | gntcttgggc | 480 |
| ttctnctgat | gccctanctg | gttgcccngn | atgccaanca | ncccaancc | ccgggtcct | 540 |
| aaancacccn | cctcctcntt | tcatctgggt | tnttntcccc | ggaccntggt | tcctctcaag | 600 |
| ggancccata | tctcnaccan | tactcaccnt | ncccccccnt | gnnaccanc | cttctanngn | 660 |
| ttcccncccg | ncctctggcc | cntcaaanan | gcttncacna | cctgggtctg | ccttccccccc | 720 |
| tncctatct | gnacccncn | tttgtctcan | tnt | | | 753 |

<210> SEQ ID NO 41
<211> LENGTH: 341
<212> TYPE: DNA
<213> ORGANISM: Homo sapien

<400> SEQUENCE: 41

| | | | | | |
|---|---|---|---|---|---|
| actatatcca | tcacaacaga | catgcttcat | cccatagact | tcttgacata | gcttcaaatg | 60 |
| agtgaaccca | tccttgattt | atatacatat | atgttctcag | tattttggga | gcctttccac | 120 |
| ttctttaaac | cttgttcatt | atgaacactg | aaaataggaa | tttgtgaaga | gttaaaaagt | 180 |
| tatagcttgt | ttacgtagta | agttttttgaa | gtctacattc | aatccagaca | cttagttgag | 240 |
| tgttaaactg | tgattttta | aaaatatcat | ttgagaatat | tctttcagag | gtattttcat | 300 |
| ttttactttt | tgattaattg | tgttttatat | attagggtag | t | | 341 |

<210> SEQ ID NO 42
<211> LENGTH: 101
<212> TYPE: DNA
<213> ORGANISM: Homo sapien

<400> SEQUENCE: 42

| | | | | | |
|---|---|---|---|---|---|
| acttactgaa | tttagttctg | tgctcttcct | tatttagtgt | tgtatcataa | atactttgat | 60 |
| gtttcaaaca | ttctaaataa | ataattttca | gtggcttcat | a | | 101 |

<210> SEQ ID NO 43
<211> LENGTH: 305
<212> TYPE: DNA
<213> ORGANISM: Homo sapien

<400> SEQUENCE: 43

| | | | | | |
|---|---|---|---|---|---|
| acatctttgt | tacagtctaa | gatgtgttct | taaatcacca | ttccttcctg | gtcctcaccc | 60 |
| tccagggtgg | tctcacactg | taattagagc | tattgaggag | tctttacagc | aaattaagat | 120 |
| tcagatgcct | tgctaagtct | agagttctag | agttatgttt | cagaaagtct | aagaaaccca | 180 |
| cctcttgaga | ggtcagtaaa | gaggacttaa | tatttcatat | ctacaaaatg | accacaggat | 240 |
| tggatacaga | acgagagtta | tcctggataa | ctcagagctg | agtacctgcc | cgggggccgc | 300 |
| tcgaa | | | | | | 305 |

<210> SEQ ID NO 44
<211> LENGTH: 852
<212> TYPE: DNA
<213> ORGANISM: Homo sapien
<220> FEATURE:
<221> NAME/KEY: misc_feature
<222> LOCATION: (1)...(852)
<223> OTHER INFORMATION: n = A,T,C or G

<400> SEQUENCE: 44

| | | | | | |
|---|---|---|---|---|---|
| acataaatat | cagagaaaag | tagtctttga | aatatttacg | tccaggagtt | ctttgtttct | 60 |
| gattatttgg | tgtgtgtttt | ggtttgtgtc | caaagtattg | gcagcttcag | ttttcatttt | 120 |
| ctctccatcc | tcgggcattc | ttcccaaatt | tatataccag | tcttcgtcca | tccacacgct | 180 |
| ccagaatttc | tcttttgtag | taatatctca | tagctcggct | gagcttttca | taggtcatgc | 240 |
| tgctgttgtt | cttcttttta | ccccatagct | gagccactgc | ctctgatttc | aagaacctga | 300 |
| agacgccctc | agatcggtct | tcccatttta | ttaatcctgg | gttcttgtct | gggttcaaga | 360 |
| ggatgtcgcg | gatgaattcc | cataagtgag | tccctctcgg | gttgtgcttt | ttggtgtggc | 420 |
| acttggcagg | ggggtcttgc | tccttttca | tatcaggtga | ctctgcaaca | ggaaggtgac | 480 |

```
tggtggttgt catggagatc tgagcccggc agaaagtttt gctgtccaac aaatctactg      540
tgctaccata gttggtgtca tataaatagt tctngtcttt ccaggtgttc atgatggaag      600
gctcagtttg ttcagtcttg acaatgacat tgtgtgtgga ctggaacagg tcactactgc      660
actggccgtt ccacttcaga tgctgcaagt tgctgtagag gagntgcccc gccgtccctg      720
ccgcccgggt gaactcctgc aaactcatgc tgcaaggtg ctcgccgttg atgtcgaact       780
cntggaaagg gatacaattg gcatccagct ggttggtgtc caggaggtga tggagccact     840
cccacacctg gt                                                         852

<210> SEQ ID NO 45
<211> LENGTH: 234
<212> TYPE: DNA
<213> ORGANISM: Homo sapien

<400> SEQUENCE: 45
acaacagacc cttgctcgct aacgacctca tgctcatcaa gttggacgaa tccgtgtccg       60
agtctgacac catccggagc atcagcattg cttcgcagtg ccctaccgcg gggaactctt     120
gcctcgtttc tggctggggt ctgctggcga acggcagaat gcctaccgtg ctgcagtgcg     180
tgaacgtgtc ggtggtgtct gaggaggtct gcagtaagct ctatgacccg ctgt           234

<210> SEQ ID NO 46
<211> LENGTH: 590
<212> TYPE: DNA
<213> ORGANISM: Homo sapien
<220> FEATURE:
<221> NAME/KEY: misc_feature
<222> LOCATION: (1)...(590)
<223> OTHER INFORMATION: n = A,T,C or G

<400> SEQUENCE: 46 acttttatt taaatgttta taaggcagat ctatgagaat gatagaaaac atggtgtgta        60
atttgatagc aatattttgg agattacaga gttttagtaa ttaccaatta cacagttaaa    120
aagaagataa tatattccaa gcanatacaa aatatctaat gaaagatcaa ggcaggaaaa    180
tgantataac taattgacaa tggaaaatca attttaatgt gaattgcaca ttatccttta    240
aaagctttca aaanaaanaa ttattgcagt ctanttaatt caaacagtgt taaatggtat    300
caggataaan aactgaaggg canaaagaat taattttcac ttcatgtaac ncacccanat    360
ttacaatggc ttaaatgcan ggaaaaagca gtggaagtag ggaagtantc aaggtctttc    420
tggtctctaa tctgccttac tctttgggtg tggctttgat cctctggaga cagctgccag    480
ggctcctgtt atatccacaa tcccagcagc aagatgaagg gatgaaaaag gacacatgct    540
gccttccttt gaggagactt catctcactg gccaacactc agtcacatgt                590

<210> SEQ ID NO 47
<211> LENGTH: 774
<212> TYPE: DNA
<213> ORGANISM: Homo sapien
<220> FEATURE:
<221> NAME/KEY: misc_feature
<222> LOCATION: (1)...(774)
<223> OTHER INFORMATION: n = A,T,C or G

<400> SEQUENCE: 47 acaaggggc ataatgaagg agtgggggana gattttaaag aaggaaaaaa aacgaggccc        60
tgaacagaat tttcctgnac aacgggctt caaataatt ttcttgggga ggttcaagac       120
gcttcactgc ttgaaactta aatggatgtg ggacanaatt ttctgtaatg accctgaggg     180
```

```
cattacagac gggactctgg gaggaaggat aaacagaaag gggacaaagg ctaatcccaa      240
aacatcaaag aaaggaaggt ggcgtcatac ctcccagcct acacagttct ccagggctct      300
cctcatccct ggaggacgac agtggaggaa caactgacca tgtccccagg ctcctgtgtg      360
ctggctcctg gtcttcagcc cccagctctg gaagcccacc ctctgctgat cctgcgtggc      420
ccacactcct tgaacacaca tccccaggtt atattcctgg acatggctga acctcctatt      480
cctacttccg agatgccttg ctccctgcag cctgtcaaaa tcccactcac cctccaaacc      540
acggcatggg aagcctttct gacttgcctg attactccag catcttggaa caatccctga      600
ttccccactc cttagaggca agatagggtg gttaagagta gggctggacc acttggagcc      660
aggctgctgg cttcaaattn tggctcattt acgagctatg ggaccttggg caagtnatct      720
tcacttctat gggcntcatt ttgttctacc tgcaaaatgg gggataataa tagt            774

<210> SEQ ID NO 48
<211> LENGTH: 124
<212> TYPE: DNA
<213> ORGANISM: Homo sapien
<220> FEATURE:
<221> NAME/KEY: misc_feature
<222> LOCATION: (1)...(124)
<223> OTHER INFORMATION: n = A,T,C or G

<400> SEQUENCE: 48
canaaattga aattttataa aaaggcattt ttctcttata tccataaaat gatataattt      60
ttgcaantat anaaatgtgt cataaattat aatgttcctt aattacagct caacgcaact     120
tggt                                                                  124

<210> SEQ ID NO 49
<211> LENGTH: 147
<212> TYPE: DNA
<213> ORGANISM: Homo sapien
<220> FEATURE:
<221> NAME/KEY: misc_feature
<222> LOCATION: (1)...(147)
<223> OTHER INFORMATION: n = A,T,C or G

<400> SEQUENCE: 49
gccgatgcta ctattttatt gcaggaggtg ggggtgtttt tattattctc tcaacagctt      60
tgtggctaca ggtggtgtct gactgcatna aaaanttttt tacgggtgat tgcaaaaatt     120
ttagggcacc catatcccaa gcantgt                                         147

<210> SEQ ID NO 50
<211> LENGTH: 107
<212> TYPE: DNA
<213> ORGANISM: Homo sapien

<400> SEQUENCE: 50
acattaaatt aataaaagga ctgttgggt tctgctaaaa cacatggctt gatatattgc       60
atggtttgag gttaggagga gttaggcata tgttttggga gagggt                    107

<210> SEQ ID NO 51
<211> LENGTH: 204
<212> TYPE: DNA
<213> ORGANISM: Homo sapien

<400> SEQUENCE: 51
gtcctaggaa gtctagggga cacacgactc tgggtcacg gggccgacac acttgcacgg       60
cgggaaggaa aggcagagaa gtgacaccgt caggggaaa tgacagaaag gaaaatcaag     120
```

| | |
|---|---|
| gccttgcaag gtcagaaagg ggactcaggg cttccaccac agccctgccc cacttggcca | 180 |
| cctcccttttt gggaccagca atgt | 204 |

<210> SEQ ID NO 52
<211> LENGTH: 491
<212> TYPE: DNA
<213> ORGANISM: Homo sapien
<220> FEATURE:
<221> NAME/KEY: misc_feature
<222> LOCATION: (1)...(491)
<223> OTHER INFORMATION: n = A,T,C or G

<400> SEQUENCE: 52

| | |
|---|---|
| acaaagataa catttatctt ataacaaaaa tttgatagtt ttaaaggtta gtattgtgta | 60 |
| gggtattttc caaagactaa agagataac tcagtaaaaa agttagaaat gtataaaaca | 120 |
| ccatcagaca ggttttttaaa aaacaacata ttacaaaatt agacaatcat ccttaaaaaa | 180 |
| aaaacttctt gtatcaattt cttttgttca aaatgactga cttaantatt tttaaatatt | 240 |
| tcanaaacac ttcctcaaaa attttcaana tggtagcttt canatgtncc ctcagtccca | 300 |
| atgttgctca gataaataaa tctcgtgaga acttaccacc caccacaagc tttctggggc | 360 |
| atgcaacagt gtcttttctt tnctttttct ttttttttttt ttacaggcac agaaactcat | 420 |
| caattttatt tggataacaa agggtctcca aattatattg aaaataaat ccaagttaat | 480 |
| atcactcttg t | 491 |

<210> SEQ ID NO 53
<211> LENGTH: 484
<212> TYPE: DNA
<213> ORGANISM: Homo sapien
<220> FEATURE:
<221> NAME/KEY: misc_feature
<222> LOCATION: (1)...(484)
<223> OTHER INFORMATION: n = A,T,C or G

<400> SEQUENCE: 53

| | |
|---|---|
| acataattta gcagggctaa ttaccataag atgctattta ttaanaggtn tatgatctga | 60 |
| gtattaacag ttgctgaagt ttggtatttt tatgcagcat tttctttttg ctttgataac | 120 |
| actacagaac ccttaaggac actgaaaatt agtaagtaaa gttcagaaac attagctgct | 180 |
| caatcaaatc tctacataac actatagtaa ttaaaacgtt aaaaaaaagt gttgaaatct | 240 |
| gcactagtat anaccgctcc tgtcaggata anactgcttt ggaacagaaa gggaaaaanc | 300 |
| agctttgant ttctttgtgc tgatangagg aaaggctgaa ttaccttgtt gcctctccct | 360 |
| aatgattggc aggtcnggta aatnccaaaa catattccaa ctcaacactt cttttccncg | 420 |
| tancttgant ctgtgtattc caggancagg cggatggaat gggccagccc ncggatgttc | 480 |
| cant | 484 |

<210> SEQ ID NO 54
<211> LENGTH: 151
<212> TYPE: DNA
<213> ORGANISM: Homo sapien

<400> SEQUENCE: 54

| | |
|---|---|
| actaaacctc gtgcttgtga actccataca gaaaacggtg ccatccctga acacggctgg | 60 |
| ccactgggta tactgctgac aaccgcaaca acaaaaacac aaatccttgg cactggctag | 120 |
| tctatgtcct ctcaagtgcc ttttttgtttg t | 151 |

-continued

```
<210> SEQ ID NO 55
<211> LENGTH: 91
<212> TYPE: DNA
<213> ORGANISM: Homo sapien

<400> SEQUENCE: 55
acctggcttg tctccgggtg gttcccggcg cccccacgg tccccagaac ggacactttc      60
gccctccagt ggatactcga gccaaagtgg t                                    91

<210> SEQ ID NO 56
<211> LENGTH: 133
<212> TYPE: DNA
<213> ORGANISM: Homo sapien

<400> SEQUENCE: 56
ggcggatgtg cgttggttat atacaaatat gtcattttat gtaagggact tgagtatact    60
tggatttttg gtatctgtgg gttgggggga cggtccagga accaataccc catggatacc   120
aagggacaac tgt                                                       133

<210> SEQ ID NO 57
<211> LENGTH: 147
<212> TYPE: DNA
<213> ORGANISM: Homo sapien
<220> FEATURE:
<221> NAME/KEY: misc_feature
<222> LOCATION: (1)...(147)
<223> OTHER INFORMATION: n = A,T,C or G

<400> SEQUENCE: 57
actctggaga acctgagccg ctgctccgcc tctgggatga ggtgatgcan gcngtggcgc    60
gactgggagc tgagcccttc cctttgcgcc tgcctcagag gattgttgcc gacntgcana   120
tctcantggg ctggatncat gcagggt                                        147

<210> SEQ ID NO 58
<211> LENGTH: 198
<212> TYPE: DNA
<213> ORGANISM: Homo sapien
<220> FEATURE:
<221> NAME/KEY: misc_feature
<222> LOCATION: (1)...(198)
<223> OTHER INFORMATION: n = A,T,C or G

<400> SEQUENCE: 58
acagggatat aggtttnaag ttattgtnat tgtaaaatac attgaatttt ctgtatactc    60
tgattacata catttatcct ttaaaaaaga tgtaaatctt aatttttatg ccatctatta   120
atttaccaat gagttaccttt gtaaatgaga agtcatgata gcactgaatt ttaactagtt   180
ttgacttcta agtttggt                                                  198

<210> SEQ ID NO 59
<211> LENGTH: 330
<212> TYPE: DNA
<213> ORGANISM: Homo sapien

<400> SEQUENCE: 59
acaacaaatg ggttgtgagg aagtcttatc agcaaaactg gtgatggcta ctgaaaagat    60
ccattgaaaa ttatcattaa tgattttaaa tgacaagtta tcaaaaactc actcaatttt   120
cacctgtgct agcttgctaa aatgggagtt aactctagag caaatatagt atcttctgaa   180
tacagtcaat aaatgacaaa gccagggcct acaggtggtt tccagacttt ccagacccag   240
```

```
cagaaggaat ctattttatc acatggatct ccgtctgtgc tcaaaatacc taatgatatt      300
tttcgtcttt attggacttc tttgaagagt                                        330

<210> SEQ ID NO 60
<211> LENGTH: 175
<212> TYPE: DNA
<213> ORGANISM: Homo sapien

<400> SEQUENCE: 60
accgtgggtg ccttctacat tcctgacggc tccttcacca acatctggtt ctacttcggc       60
gtcgtgggct ccttcctctt catcctcatc cagctggtgc tgctcatcga ctttgcgcac      120
tcctggaacc agcggtggct gggcaaggcc gaggagtgcg attcccgtgc ctggt           175

<210> SEQ ID NO 61
<211> LENGTH: 154
<212> TYPE: DNA
<213> ORGANISM: Homo sapien

<400> SEQUENCE: 61
accccacttt tcctcctgtg agcagtctgg acttctcact gctacatgat gagggtgagt       60
ggttgttgct cttcaacagt atcctcccct ttccggatct gctgagccgg acagcagtgc      120
tggactgcac agccccgggg ctccacattg ctgt                                  154

<210> SEQ ID NO 62
<211> LENGTH: 30
<212> TYPE: DNA
<213> ORGANISM: Homo sapien

<400> SEQUENCE: 62
cgctcgagcc ctatagtgag tcgtattaga                                        30

<210> SEQ ID NO 63
<211> LENGTH: 89
<212> TYPE: DNA
<213> ORGANISM: Homo sapien

<400> SEQUENCE: 63
acaagtcatt tcagcaccct ttgctcttca aaactgacca tcttttatat ttaatgcttc       60
ctgtatgaat aaaaatggtt atgtcaagt                                         89

<210> SEQ ID NO 64
<211> LENGTH: 97
<212> TYPE: DNA
<213> ORGANISM: Homo sapien

<400> SEQUENCE: 64
accggagtaa ctgagtcggg acgctgaatc tgaatccacc aataaataaa ggttctgcag       60
aatcagtgca tccaggattg gtccttggat ctggggt                                97

<210> SEQ ID NO 65
<211> LENGTH: 377
<212> TYPE: DNA
<213> ORGANISM: Homo sapien
<220> FEATURE:
<221> NAME/KEY: misc_feature
<222> LOCATION: (1)...(377)
<223> OTHER INFORMATION: n = A,T,C or G
```

```
<400> SEQUENCE: 65
acaacaanaa ntcccttctt taggccactg atggaaacct ggaaccccct tttgatggca      60
gcatggcgtc ctaggccttg acacagcggc tggggtttgg gctntcccaa accgcacacc     120
ccaaccctgg tctacccaca nttctggcta tgggctgtct ctgccactga acatcagggt     180
tcggtcataa natgaaatcc caanggggac agaggtcagt agaggaagct caatgagaaa     240
ggtgctgttt gctcagccag aaaacagctg cctggcattc gccgctgaac tatgaacccg     300 tggggtgaa ctaccccan gaggaatcat gcctgggcga tgcaanggtg ccaacaggag       360
gggcgggagg agcatgt                                                    377

<210> SEQ ID NO 66
<211> LENGTH: 305
<212> TYPE: DNA
<213> ORGANISM: Homo sapien

<400> SEQUENCE: 66
acgcctttcc ctcagaattc agggaagaga ctgtcgcctg ccttcctccg ttgttgcgtg      60
agaacccgtg tgccccttcc caccatatcc accctcgctc catctttgaa ctcaaacacg     120
aggaactaac tgcaccctgg tcctctcccc agtccccagt tcaccctcca tccctcacct     180
tcctccactc taaggggatat caacactgcc cagcacaggg gccctgaatt tatgtggttt    240
ttatatattt tttaataaga tgcactttat gtcattttttt aataaagtct gaagaattac    300
tgttt                                                                 305

<210> SEQ ID NO 67
<211> LENGTH: 385
<212> TYPE: DNA
<213> ORGANISM: Homo sapien

<400> SEQUENCE: 67
actacacaca ctccacttgc ccttgtgaga cactttgtcc cagcacttta ggaatgctga      60
ggtcggacca gccacatctc atgtgcaaga ttgcccagca gacatcaggt ctgagagttc     120 ccctttaaa aaggggact tgcttaaaaa agaagtctag ccacgattgt gtagagcagc       180
tgtgctgtgc tggagattca cttttgagag agttctcctc tgagacctga tctttagagg     240
ctgggcagtc ttgcacatga gatggggctg gtctgatctc agcactcctt agtctgcttg     300
cctctcccag ggcccagcc tggccacacc tgcttacagg gcactctcag atgcccatac      360
catagtttct gtgctagtgg accgt                                           385

<210> SEQ ID NO 68
<211> LENGTH: 73
<212> TYPE: DNA
<213> ORGANISM: Homo sapien

<400> SEQUENCE: 68
acttaaccag atatatttttt accccagatg gggatattct ttgtaaaaaa tgaaaataaa     60 gttttttttaa tgg                                                       73

<210> SEQ ID NO 69
<211> LENGTH: 536
<212> TYPE: DNA
<213> ORGANISM: Homo sapien
<220> FEATURE:
<221> NAME/KEY: misc_feature
<222> LOCATION: (1)...(536)
<223> OTHER INFORMATION: n = A,T,C or G
```

```
<400> SEQUENCE: 69
actagtccag tgtggtggaa ttccattgtg ttgggggctc tcaccctcct ctcctgcagc      60
tccagctttg tgctctgcct ctgaggagac catggcccag catctgagta ccctgctgct     120
cctgctggcc accctagctg tggccctggc ctggagcccc aaggaggagg ataggataat     180
cccgggtggc atctataacg cagacctcaa tgatgagtgg gtacagcgtg cccttcactt     240
cgccatcagc gagtataaca aggccaccaa agatgactac tacagacgtc cgctgcgggt     300
actaagagcc aggcaacaga ccgttggggg ggtgaattac ttcttcgacg tagaggtggg     360
ccgaaccata tgtaccaagt cccagcccaa cttggacacc tgtgccttcc atgaacagcc     420
agaactgcag aagaaacagt tgtgctcttt cgagatctac gaagttccct ggggagaaca     480
gaangtccct gggtgaaatc caggtgtcaa gaaatcctan ggatctgttg ccaggc         536

<210> SEQ ID NO 70
<211> LENGTH: 477
<212> TYPE: DNA
<213> ORGANISM: Homo sapien

<400> SEQUENCE: 70 atgacccta acaggggccc tctcagccct cctaatgacc tccggcctag ccatgtgatt      60
tcacttccac tccataacgc tcctcatact aggcctacta accaacacac taaccatata     120
ccaatgatgg cgcgatgtaa cacgagaaag cacataccaa ggccaccaca caccacctgt     180
ccaaaaaggc cttcgatacg ggataatcct atttattacc tcagaagttt ttttcttcgc     240
agggattttt ctgagccttt taccactcca gcctagcccc taccccccaa ctaggagggc     300
actggccccc aacaggcatc accccgctaa atcccctaga agtccactc ctaaacacat      360 ccgtattact cgcatcagga gtatcaatca cctgagctca ccatagtcta atagaaaaca     420
accgaaacca aattattcaa agcactgctt attacaattt tactgggtct ctattt        477

<210> SEQ ID NO 71
<211> LENGTH: 533
<212> TYPE: DNA
<213> ORGANISM: Homo sapien
<220> FEATURE:
<221> NAME/KEY: misc_feature
<222> LOCATION: (1)...(533)
<223> OTHER INFORMATION: n = A,T,C or G

<400> SEQUENCE: 71
agagctatag gtacagtgtg atctcagctt tgcaaacaca ttttctacat agatagtact      60
aggtattaat agatatgtaa agaaagaaat cacaccatta ataatggtaa gattggttta     120
tgtgatttta gtggtatttt tggcacccct atatatgttt tccaaacttt cagcagtgat     180
attatttcca taacttaaaa agtgagtttg aaaagaaaa tctccagcaa gcatctcatt      240
taaataaagg tttgtcatct ttaaaaatac agcaatatgt gacttttttaa aaagctgtc    300 aaataggtgt gaccctacta ataattatta gaaatacatt taaaacatc gagtacctca     360 agtcagtttg ccttgaaaaa tatcaaatat aactcttaga gaaatgtaca taaagaatg      420 cttcgtaatt ttggagtang aggttccctc ctcaatttg tatttttaaa aagtacatgg    480
taaaaaaaaa aattcacaac agtatataag gctgtaaaat gaagaattct gcc           533

<210> SEQ ID NO 72
<211> LENGTH: 511
<212> TYPE: DNA
<213> ORGANISM: Homo sapien
```

```
<220> FEATURE:
<221> NAME/KEY: misc_feature
<222> LOCATION: (1)...(511)
<223> OTHER INFORMATION: n = A,T,C or G

<400> SEQUENCE: 72
tattacggaa aaacacacca cataattcaa ctancaaaga anactgcttc agggcgtgta      60
aaatgaaagg cttccaggca gttatctgat taaagaacac taaagagggg acaaggctaa    120
aagccgcagg atgtctacac tatancaggc gctatttggg ttggctggag agctgtgga    180
aaacatggan agattggtgc tgganatcgc cgtggctatt cctcattgtt attacanagt    240
gaggttctct gtgtgcccac tggtttgaaa accgttctnc aataatgata gaatagtaca    300
cacatgagaa ctgaaatggc ccaaacccag aaagaaagcc caactagatc ctcagaanac    360
gcttctaggg acaataaccg atgaagaaaa gatggcctcc ttgtgccccc gtctgttatg    420
atttctctcc attgcagcna naaacccgtt cttctaagca aacncaggtg atgatggcna    480
aaatacaccc cctcttgaag naccnggagg a                                   511

<210> SEQ ID NO 73
<211> LENGTH: 499
<212> TYPE: DNA
<213> ORGANISM: Homo sapien
<220> FEATURE:
<221> NAME/KEY: misc_feature
<222> LOCATION: (1)...(499)
<223> OTHER INFORMATION: n = A,T,C or G

<400> SEQUENCE: 73
cagtgccagc actggtgcca gtaccagtac caataacagt gccagtgcca gtgccagcac     60
cagtggtggc ttcagtgctg gtgccagcct gaccgccact ctcacatttg ggctcttcgc    120
tggccttggt ggagctggtg ccagcaccag tggcagctct ggtgcctgtg gtttctccta    180
caagtgagat tttagatatt gttaatcctg ccagtctttc tcttcaagcc agggtgcatc    240
ctcagaaacc tactcaacac agcactctag gcagccacta tcaatcaatt gaagttgaca    300
ctctgcatta aatctatttg ccatttctga aaaaaaaaa aaaaaagggg cggccgctcg    360
antctagagg gcccgtttaa acccgctgat cagcctcgac tgtgccttct anttgccagc    420
catctgttgt ttgcccctcc cccgntgcct tccttgaccc tggaaagtgc cactcccact    480
gtcctttcct aantaaaat                                                 499

<210> SEQ ID NO 74
<211> LENGTH: 537
<212> TYPE: DNA
<213> ORGANISM: Homo sapien
<220> FEATURE:
<221> NAME/KEY: misc_feature
<222> LOCATION: (1)...(537)
<223> OTHER INFORMATION: n = A,T,C or G

<400> SEQUENCE: 74
tttcatagga gaacacactg aggagatact tgaagaattt ggattcagcc gcgaagagat     60
ttatcagctt aactcagata aaatcattga agtaataag gtaaaagcta gtctctaact    120
tccaggccca cggctcaagt gaatttgaat actgcattta cagtgtagag taacacataa    180
cattgtatgc atggaaacat ggaggaacag tattacagtg tcctaccact ctaatcaaga    240
aaagaattac agactctgat tctacagtga tgattgaatt ctaaaaatgg taatcattag    300
ggcttttgat ttataanact ttgggtactt atactaaatt atggtagtta tactgccttc    360
```

```
cagtttgctt gatatatttg ttgatattaa gattcttgac ttatattttg aatgggttct    420
actgaaaaan gaatgatata ttcttgaaga catcgatata catttattta cactcttgat    480
tctacaatgt agaaaatgaa ggaaatgccc caaattgtat ggtgataaaa gtcccgt       537
```

<210> SEQ ID NO 75
<211> LENGTH: 467
<212> TYPE: DNA
<213> ORGANISM: Homo sapien
<220> FEATURE:
<221> NAME/KEY: misc_feature
<222> LOCATION: (1)...(467)
<223> OTHER INFORMATION: n = A,T,C or G

<400> SEQUENCE: 75

```
caaanacaat tgttcaaaag atgcaaatga tacactactg ctgcagctca caaacacctc    60
tgcatattac acgtacctcc tcctgctcct caagtagtgt ggtctatttt gccatcatca    120
cctgctgtct gctagaaga acggctttct gctgcaangg agagaaatca taacagacgg     180
tggcacaagg aggccatctt ttcctcatcg gttattgtcc ctagaagcgt cttctgagga    240
tctagttggg ctttctttct gggtttgggc catttcantt ctcatgtgtg tactattcta    300
tcattattgt ataacggttt tcaaaccngt gggcacncag agaacctcac tctgtaataa    360
caatgaggaa tagccacggt gatctccagc accaaatctc tccatgttnt tccagagctc    420
ctccagccaa cccaaatagc cgctgctatn gtgtagaaca tccctgn                 467
```

<210> SEQ ID NO 76
<211> LENGTH: 400
<212> TYPE: DNA
<213> ORGANISM: Homo sapien
<220> FEATURE:
<221> NAME/KEY: misc_feature
<222> LOCATION: (1)...(400)
<223> OTHER INFORMATION: n = A,T,C or G

<400> SEQUENCE: 76

```
aagctgacag cattcgggcc gagatgtctc gctccgtggc cttagctgtg ctcgcgctac    60
tctctctttc tggcctggag gctatccagc gtactccaaa gattcaggtt tactcacgtc    120
atccagcaga gaatgaaaag tcaaatttcc tgaattgcta tgtgtctggg tttcatccat    180
ccgacattga agttgactta ctgaagaatg gagagagaat tgaaaagtg gagcattcag     240 acttgtcttt cagcaaggac tggtctttct atctcttgta ctacactgaa ttcacccca    300 ctgaaaaaga tgagtatgcc tgccgtgtga accatgtgac tttgtcacag cccaagatng    360
ttnagtggga tcganacatg taagcagcan catgggaggt                          400
```

<210> SEQ ID NO 77
<211> LENGTH: 248
<212> TYPE: DNA
<213> ORGANISM: Homo sapien

<400> SEQUENCE: 77

```
ctggagtgcc ttggtgtttc aagcccctgc aggaagcaga atgcaccttc tgaggcacct    60
ccagctgccc cggcggggga tgcgaggctc ggagcaccct tgcccggctg tgattgctgc    120
caggcactgt tcatctcagc ttttctgtcc ctttgctccc ggcaagcgct tctgctgaaa    180
gttcatatct ggagcctgat gtcttaacga ataaggtcc catgctccac ccgaaaaaaa    240
aaaaaaaa                                                            248
```

<210> SEQ ID NO 78
<211> LENGTH: 201
<212> TYPE: DNA
<213> ORGANISM: Homo sapien

<400> SEQUENCE: 78

| actagtccag tgtggtggaa ttccattgtg ttgggcccaa cacaatggct acctttaaca | 60 |
| tcacccagac cccgccctgc ccgtgcccca cgctgctgct aacgacagta tgatgcttac | 120 |
| tctgctactc ggaaactatt tttatgtaat taatgtatgc tttcttgttt ataaatgcct | 180 |
| gatttaaaaa aaaaaaaaaa a | 201 |

<210> SEQ ID NO 79
<211> LENGTH: 552
<212> TYPE: DNA
<213> ORGANISM: Homo sapien
<220> FEATURE:
<221> NAME/KEY: misc_feature
<222> LOCATION: (1)...(552)
<223> OTHER INFORMATION: n = A,T,C or G

<400> SEQUENCE: 79

| tcctttttgtt aggttttttga gacaaccctaa gacctaaaact gtgtcacaga cttctgaatg | 60 |
| tttaggcagt gctagtaatt tcctcgtaat gattctgtta ttactttcct attctttatt | 120 |
| cctctttctt ctgaagatta atgaagttga aaattgaggt ggataaatac aaaaaggtag | 180 |
| tgtgatagta taagtatcta agtgcagatg aaagtgtgtt atatatatcc attcaaaatt | 240 |
| atgcaagtta gtaattactc agggttaact aaattacttt aatatgctgt tgaacctact | 300 |
| ctgttccttg gctagaaaaa attataaaca ggactttgtt agtttgggaa gccaaattga | 360 |
| taatattcta tgttctaaaa gttgggctat acataaanta tnaagaaata tggaattta | 420 |
| ttcccaggaa tatggggttc atttatgaat antacccggg anagaagttt tgantnaaac | 480 |
| cngttttggt taatacgtta atatgtcctn aatnaacaag gcntgactta tttccaaaaa | 540 |
| aaaaaaaaaa aa | 552 |

<210> SEQ ID NO 80
<211> LENGTH: 476
<212> TYPE: DNA
<213> ORGANISM: Homo sapien
<220> FEATURE:
<221> NAME/KEY: misc_feature
<222> LOCATION: (1)...(476)
<223> OTHER INFORMATION: n = A,T,C or G

<400> SEQUENCE: 80

| acagggattt gagatgctaa ggccccagag atcgtttgat ccaaccctct tattttcaga | 60 |
| ggggaaaatg gggcctagaa gttacagagc atctagctgg tgcgctggca ccctggcct | 120 |
| cacacagact cccgagtagc tgggactaca ggcacacagt cactgaagca ggccctgttt | 180 |
| gcaattcacg ttgccacctc caacttaaac attcttcata tgtgatgtcc ttagtcacta | 240 |
| aggttaaact ttcccaccca gaaaggcaa cttagataaa atcttagagt actttcatac | 300 |
| tcttctaagt cctcttccag cctcactttg agtcctcctt gggggttgat aggaantntc | 360 |
| tcttggcttt ctcaataaaa tctctatcca tctcatgttt aatttggtac gcntaaaaat | 420 |
| gctgaaaaaa ttaaaatgtt ctggtttcnc tttaaaaaaa aaaaaaaaaa aaaaaa | 476 |

<210> SEQ ID NO 81
<211> LENGTH: 232
<212> TYPE: DNA
<213> ORGANISM: Homo sapien
<220> FEATURE:
<221> NAME/KEY: misc_feature
<222> LOCATION: (1)...(232)
<223> OTHER INFORMATION: n = A,T,C or G

<400> SEQUENCE: 81

| | | | | |
|---|---|---|---|---|
| tttttttttg | tatgccntcn | ctgtggngtt | attgttgctg | ccaccctgga ggagcccagt | 60 |
| ttcttctgta | tctttctttt | ctggggatc | ttcctggctc | tgcccctcca ttcccagcct | 120 |
| ctcatcccca | tcttgcactt | ttgctagggt | tggaggcgct | ttcctggtag cccctcagag | 180 |
| actcagtcag | cgggaataag | tcctaggggt | gggggtgtg | gcaagccggc ct | 232 |

<210> SEQ ID NO 82
<211> LENGTH: 383
<212> TYPE: DNA
<213> ORGANISM: Homo sapien
<220> FEATURE:
<221> NAME/KEY: misc_feature
<222> LOCATION: (1)...(383)
<223> OTHER INFORMATION: n = A,T,C or G

<400> SEQUENCE: 82

| | | | | |
|---|---|---|---|---|
| aggcgggagc | agaagctaaa | gccaaagccc | aagaagagtg | gcagtgccag cactggtgcc | 60 |
| agtaccagta | ccaataacat | gccagtgcca | gtgccagcac | cagtggtggc ttcagtgctg | 120 |
| gtgccagcct | gaccgccact | ctcacatttg | ggctcttcgc | tggccttggt ggagctggtg | 180 |
| ccagcaccag | tggcagctct | ggtgcctgtg | gtttctccta | caagtgagat tttagatatt | 240 |
| gttaatcctg | ccagtctttc | tcttcaagcc | agggtgcatc | ctcagaaacc tactcaacac | 300 |
| agcactctng | gcagccacta | tcaatcaatt | gaagttgaca | ctctgcatta aatctatttg | 360 |
| ccatttcaaa | aaaaaaaaaa | aaa | | | 383 |

<210> SEQ ID NO 83
<211> LENGTH: 494
<212> TYPE: DNA
<213> ORGANISM: Homo sapien
<220> FEATURE:
<221> NAME/KEY: misc_feature
<222> LOCATION: (1)...(494)
<223> OTHER INFORMATION: n = A,T,C or G

<400> SEQUENCE: 83

| | | | | |
|---|---|---|---|---|
| accgaattgg | gaccgctggc | ttataagcga | tcatgtcctc | cagtattacc tcaacgagca | 60 |
| gggagatcga | gtctatacgc | tgaagaaatt | tgacccgatg | ggacaacaga cctgctcagc | 120 |
| ccatcctgct | cggttctccc | cagatgacaa | atactctcga | caccgaatca ccatcaagaa | 180 |
| acgcttcaag | gtgctcatga | cccagcaacc | gcgccctgtc | ctctgagggt ccttaaactg | 240 |
| atgtcttttc | tgccacctgt | tacccctcgg | agactccgta | accaaactct tcggactgtg | 300 |
| agccctgatg | ccttttttgcc | agccatactc | tttggcntcc | agtctctcgt ggcgattgat | 360 |
| tatgcttgtg | tgaggcaatc | atggtggcat | cacccatnaa | gggaacacat ttganttttt | 420 |
| tttcncatat | tttaaattac | naccagaata | nttcagaata | aatgaattga aaaactctta | 480 |
| aaaaaaaaaa | aaaa | | | | 494 |

<210> SEQ ID NO 84
<211> LENGTH: 380
<212> TYPE: DNA
<213> ORGANISM: Homo sapien
<220> FEATURE:
<221> NAME/KEY: misc_feature
<222> LOCATION: (1)...(380)
<223> OTHER INFORMATION: n = A,T,C or G

<400> SEQUENCE: 84
gctggtagcc tatggcgtgg ccacggangg gctcctgagg cacgggacag tgacttccca      60
agtatcctgc gccgcgtctt ctaccgtccc tacctgcaga tcttcgggca gattccccag     120
gaggacatgg acgtggccct catggagcac agcaactgct cgtcggagcc cggcttctgg     180
gcacaccctc ctggggccca ggcgggcacc tgcgtctccc agtatgccaa ctggctggtg     240
gtgctgctcc tcgtcatctt cctgctcgtg gccaacatcc tgctggtcac ttgctcattg     300
ccatgttcag ttacacattc ggcaaagtac agggcaacag cnatctctac tgggaaggcc     360
agcgttnccg cctcatccgg                                                 380

<210> SEQ ID NO 85
<211> LENGTH: 481
<212> TYPE: DNA
<213> ORGANISM: Homo sapien
<220> FEATURE:
<221> NAME/KEY: misc_feature
<222> LOCATION: (1)...(481)
<223> OTHER INFORMATION: n = A,T,C or G

<400> SEQUENCE: 85
gagttagctc ctccacaacc ttgatgaggt cgtctgcagt ggcctctcgc ttcataccgc      60
tnccatcgtc atactgtagg tttgccacca cctcctgcat cttggggcgg ctaatatcca     120
ggaaactctc aatcaagtca ccgtcnatna aacctgtggc tggttctgtc ttccgctcgg     180
tgtgaaagga tctccagaag gagtgctcga tcttccccac acttttgatg actttattga     240
gtcgattctg catgtccagc aggaggttgt accagctctc tgacagtgag gtcaccagcc     300
ctatcatgcc nttgaacgtg ccgaagaaca ccgagccttg tgtgggggt gnagtctcac      360 ccagattctg cattaccaga nagccgtggc aaaaganatt gacaactcgc ccaggnngaa     420
aaagaacacc tcctggaagt gctngccgct cctcgtccnt tggtggnngc gcntnccttt     480
t                                                                    481

<210> SEQ ID NO 86
<211> LENGTH: 472
<212> TYPE: DNA
<213> ORGANISM: Homo sapien
<220> FEATURE:
<221> NAME/KEY: misc_feature
<222> LOCATION: (1)...(472)
<223> OTHER INFORMATION: n = A,T,C or G

<400> SEQUENCE: 86
aacatcttcc tgtataatgc tgtgtaatat cgatccgatn ttgtctgctg agaattcatt      60
acttggaaaa gcaacttnaa gcctggacac tggtattaaa attcacaata tgcaacactt     120
taaacagtgt gtcaatctgc tcccttactt tgtcatcacc agtctgggaa taagggtatg     180
ccctattcac acctgttaaa agggcgctaa gcatttttga ttcaacatct ttttttttga     240
cacaagtccg aaaaaagcaa agtaaacag ttnttaattt gttagccaat tcactttctt     300
catgggacag agccatttga tttaaaaagc aaattgcata atattgagct ttgggagctg     360

```
atatntgagc ggaagantag cctttctact tcaccagaca caactccttt catattggga    420 tgtttnacnaa agttatgtct cttacagatg ggatgctttt gtggcaattc tg           472

<210> SEQ ID NO 87
<211> LENGTH: 413
<212> TYPE: DNA
<213> ORGANISM: Homo sapien
<220> FEATURE:
<221> NAME/KEY: misc_feature
<222> LOCATION: (1)...(413)
<223> OTHER INFORMATION: n = A,T,C or G

<400> SEQUENCE: 87
agaaaccagt atctctnaaa acaacctctc ataccttgtg gacctaatttt tgtgtgcgtg    60 tgtgtgtgcg cgcatattat atagacaggc acatctttt tactttgta aaagcttatg     120 cctctttggt atctatatct gtgaaagttt taatgatctg ccataatgtc ttggggacct   180
ttgtcttctg tgtaaatggt actagagaaa cacctatnt tatgagtcaa tctagttngt    240
tttattcgac atgaaggaaa tttccagatn acaacactna caaactctcc cttgactagg   300
ggggacaaag aaaagcanaa ctgaacatna gaaacaattn cctggtgaga aattncataa   360
acagaaattg ggtngtatat tgaaananng catcattnaa acgttttttt ttt          413

<210> SEQ ID NO 88
<211> LENGTH: 448
<212> TYPE: DNA
<213> ORGANISM: Homo sapien
<220> FEATURE:
<221> NAME/KEY: misc_feature
<222> LOCATION: (1)...(448)
<223> OTHER INFORMATION: n = A,T,C or G

<400> SEQUENCE: 88
cgcagcgggt cctctctatc tagctccagc ctctcgcctg ccccactccc cgcgtcccgc    60
gtcctagccn accatggccg ggcccctgcg cgccccgctg ctcctgctgg ccatcctggc   120
cgtggccctg gccgtgagcc ccgcggccgg ctccagtccc ggcaagccgc cgcgcctggt   180
gggaggccca tggaccccgc gtggaagaag aaggtgtgcg gcgtgcactg gactttgccg   240
tcggcnanta caacaaaccc gcaacnactt ttaccnagcn cgcgctgcag gttgtgccgc   300
cccaancaaa ttgttactng gggtaantaa ttcttggaag ttgaacctgg gccaaacnng   360
tttaccagaa ccnagccaat tngaacaatt nccctccat aacagcccct tttaaaaagg   420
gaancantcc tgntctttc caaatttt                                       448

<210> SEQ ID NO 89
<211> LENGTH: 463
<212> TYPE: DNA
<213> ORGANISM: Homo sapien
<220> FEATURE:
<221> NAME/KEY: misc_feature
<222> LOCATION: (1)...(463)
<223> OTHER INFORMATION: n = A,T,C or G

<400> SEQUENCE: 89
gaattttgtg cactggccac tgtgatggaa ccattgggcc aggatgcttt gagtttatca    60
gtagtgattc tgccaaagtt ggtgttgtaa catgagtatg taaaatgtca aaaaattagc   120
agaggtctag gtctgcatat cagcagacag tttgtccgtg tattttgtag ccttgaagtt   180
ctcagtgaca agtnnttct gatgcgaagt tctnattcca gtgttttagt cctttgcatc   240
tttnatgttn agacttgcct ctntnaaatt gcttttgtnt tctgcaggta ctatctgtgg   300
```

| | |
|---|---|
| tttaacaaaa tagaannact tctctgcttn gaanatttga atatcttaca tctnaaaatn | 360 |
| aattctctcc ccatannaaa acccangccc ttgggganaat ttgaaaaang gntccttcnn | 420 |
| aattcnnana anttcagntn tcatacaaca naacngganc ccc | 463 |

<210> SEQ ID NO 90
<211> LENGTH: 400
<212> TYPE: DNA
<213> ORGANISM: Homo sapien
<220> FEATURE:
<221> NAME/KEY: misc_feature
<222> LOCATION: (1)...(400)
<223> OTHER INFORMATION: n = A,T,C or G

<400> SEQUENCE: 90

| | |
|---|---|
| agggattgaa ggtctnttnt actgtcggac tgttcancca ccaactctac aagttgctgt | 60 |
| cttccactca ctgtctgtaa gcntnttaac ccagactgta tcttcataaa tagaacaaat | 120 |
| tcttcaccag tcacatcttc taggacccttt ttggattcag ttagtataag ctcttccact | 180 |
| tcctttgtta agacttcatc tggtaaagtc ttaagttttg tagaaaggaa tttaattgct | 240 |
| cgttctctaa caatgtcctc tccttgaagt atttggctga acaacccacc tnaagtccct | 300 |
| ttgtgcatcc attttaaata tacttaatag ggcattggtn cactaggtta aattctgcaa | 360 |
| gagtcatctg tctgcaaaag ttgcgttagt atatctgcca | 400 |

<210> SEQ ID NO 91
<211> LENGTH: 480
<212> TYPE: DNA
<213> ORGANISM: Homo sapien
<220> FEATURE:
<221> NAME/KEY: misc_feature
<222> LOCATION: (1)...(480)
<223> OTHER INFORMATION: n = A,T,C or G

<400> SEQUENCE: 91

| | |
|---|---|
| gagctcggat ccaataatct ttgtctgagg gcagcacaca tatncagtgc catggnaact | 60 |
| ggtctacccc acatgggagc agcatgccgt agntatataa ggtcattccc tgagtcagac | 120 |
| atgcctcttt gactaccgtg tgccagtgct ggtgattctc acacacctcc nnccgctctt | 180 |
| tgtggaaaaa ctggcacttg nctggaacta gcaagacatc acttacaaat tcacccacga | 240 |
| gacacttgaa aggtgtaaca aagcgactct tgcattgctt tttgtccctc cggcaccagt | 300 |
| tgtcaatact aacccgctgg tttgcctcca tcacatttgt gatctgtagc tctggataca | 360 |
| tctcctgaca gtactgaaga acttcttctt ttgtttcaaa agcaactctt ggtgcctgtt | 420 |
| ngatcaggtt cccatttccc agtccgaatg ttcacatggc atatnttact tcccacaaaa | 480 |

<210> SEQ ID NO 92
<211> LENGTH: 477
<212> TYPE: DNA
<213> ORGANISM: Homo sapien
<220> FEATURE:
<221> NAME/KEY: misc_feature
<222> LOCATION: (1)...(477)
<223> OTHER INFORMATION: n = A,T,C or G

<400> SEQUENCE: 92

| | |
|---|---|
| atacagccca natcccacca cgaagatgcg cttgttgact gagaacctga tgcggtcact | 60 |
| ggtcccgctg tagccccagc gactctccac ctgctggaag cggttgatgc tgcactcctt | 120 |
| cccacgcagg cagcagcggg gccggtcaat gaactccact cgtggcttgg ggttgacggt | 180 |
| taantgcagg aagaggctga ccacctcgcg gtccaccagg atgcccgact gtgcgggacc | 240 |

```
tgcagcgaaa ctcctcgatg gtcatgagcg ggaagcgaat gangcccagg gccttgccca      300
gaaccttccg cctgttctct ggcgtcacct gcagctgctg ccgctnacac tcggcctcgg      360
accagcggac aaacggcgtt gaacagccgc acctcacgga tgcccantgt gtcgcgctcc      420
aggaacggcn ccagcgtgtc caggtcaatg tcggtgaanc ctccgcgggt aatggcg         477
```

<210> SEQ ID NO 93
<211> LENGTH: 377
<212> TYPE: DNA
<213> ORGANISM: Homo sapien
<220> FEATURE:
<221> NAME/KEY: misc_feature
<222> LOCATION: (1)...(377)
<223> OTHER INFORMATION: n = A,T,C or G

<400> SEQUENCE: 93

```
gaacggctgg accttgcctc gcattgtgct gctggcagga ataccttggc aagcagctcc       60
agtccgagca gccccagacc gctgccgccc gaagctaagc ctgcctctgg ccttcccctc      120
cgcctcaatg cagaaccant agtgggagca ctgtgtttag agttaagagt gaacactgtn      180
tgattttact tgggaatttc ctctgttata tagcttttcc caatgctaat ttccaaacaa      240
caacaacaaa ataacatgtt tgcctgttna gttgtataaa agtangtgat tctgtatnta      300
aagaaaatat tactgttaca tatactgctt gcaanttctg tatttattgg tnctctggaa      360
ataaatatat tattaaa                                                    377
```

<210> SEQ ID NO 94
<211> LENGTH: 495
<212> TYPE: DNA
<213> ORGANISM: Homo sapien
<220> FEATURE:
<221> NAME/KEY: misc_feature
<222> LOCATION: (1)...(495)
<223> OTHER INFORMATION: n = A,T,C or G

<400> SEQUENCE: 94

```
ccctttgagg ggttagggtc cagttcccag tggaagaaac aggccaggag aantgcgtgc       60
cgagctgang cagatttccc acagtgaccc cagagccctg ggctatagtc tctgacccct      120
ccaaggaaag accaccttct ggggacatgg gctggagggc aggacctaga ggcaccaagg      180
gaaggcccca ttccggggct gttccccgag gaggaaggga aggggctctg tgtgccccc       240 acgaggaana ggccctgant cctgggatca nacacccctt cacgtgtatc cccacacaaa      300
tgcaagctca ccaaggtccc ctctcagtcc cttccctaca ccctgaacgg ncactggccc      360
acacccaccc agancancca cccgccatgg ggaatgtnct caaggaatcg cngggcaacg      420
tggactctng tcccnnaagg gggcagaatc tccaatagan gganngaacc cttgctnana      480
aaaaaaaana aaaaa                                                      495
```

<210> SEQ ID NO 95
<211> LENGTH: 472
<212> TYPE: DNA
<213> ORGANISM: Homo sapien
<220> FEATURE:
<221> NAME/KEY: misc_feature
<222> LOCATION: (1)...(472)
<223> OTHER INFORMATION: n = A,T,C or G

<400> SEQUENCE: 95

```
ggttacttgg tttcattgcc accacttagt ggatgtcatt tagaaccatt ttgtctgctc       60
cctctggaag ccttgcgcag agcggacttt gtaattgttg gagaataact gctgaatttt      120
```

| tagctgtttt gagttgattc gcaccactgc accacaactc aatatgaaaa ctatttnact | 180 |
| tatttattat cttgtgaaaa gtatacaatg aaaattttgt tcatactgta tttatcaagt | 240 |
| atgatgaaaa gcaatagata tatattcttt tattatgttn aattatgatt gccattatta | 300 |
| atcggcaaaa tgtggagtgt atgttctttt cacagtaata tatgccttt gtaacttcac | 360 |
| ttggttattt tattgtaaat gaattacaaa attcttaatt taagaaaatg gtangttata | 420 |
| tttanttcan taatttcttt ccttgtttac gttaattttg aaaagaatgc at | 472 |

<210> SEQ ID NO 96
<211> LENGTH: 476
<212> TYPE: DNA
<213> ORGANISM: Homo sapien
<220> FEATURE:
<221> NAME/KEY: misc_feature
<222> LOCATION: (1)...(476)
<223> OTHER INFORMATION: n = A,T,C or G

<400> SEQUENCE: 96

| ctgaagcatt tcttcaaact tntctacttt tgtcattgat acctgtagta agttgacaat | 60 |
| gtggtgaaat ttcaaaatta tatgtaactt ctactagttt tactttctcc cccaagtctt | 120 |
| ttttaactca tgatttttac acacacaatc cagaacttat tatatagcct ctaagtcttt | 180 |
| attcttcaca gtagatgatg aaagagtcct ccagtgtctt gngcanaatg ttctagntat | 240 |
| agctggatac atacngtggg agttctataa actcatacct cagtgggact naaccaaaat | 300 |
| tgtgttagtc tcaattccta ccacactgag ggagcctccc aaatcactat attcttatct | 360 |
| gcaggtactc ctccagaaaa acngacaggg caggcttgca tgaaaaagtn acatctgcgt | 420 |
| tacaaagtct atcttcctca nangtctgtn aaggaacaat ttaatcttct agcttt | 476 |

<210> SEQ ID NO 97
<211> LENGTH: 479
<212> TYPE: DNA
<213> ORGANISM: Homo sapien
<220> FEATURE:
<221> NAME/KEY: misc_feature
<222> LOCATION: (1)...(479)
<223> OTHER INFORMATION: n = A,T,C or G

<400> SEQUENCE: 97

| actctttcta atgctgatat gatcttgagt ataagaatgc atatgtcact agaatggata | 60 |
| aaataatgct gcaaacttaa tgttcttatg caaaatggaa cgctaatgaa acacagctta | 120 |
| caatcgcaaa tcaaaactca caagtgctca tctgttgtag atttagtgta ataagactta | 180 |
| gattgtgctc cttcggatat gattgttttct canatcttgg gcaatnttcc ttagtcaaat | 240 |
| caggctacta gaattctgtt attggatatn tgagagcatg aaattttaa naatacactt | 300 |
| gtgattatna aattaatcac aaatttcact tatacctgct atcagcagct agaaaaacat | 360 |
| ntnnttttta natcaaagta ttttgtgttt ggaantgtnn aaatgaaatc tgaatgtggg | 420 |
| ttcnatctta ttttttcccn gacnactant tncttttta gggnctattc tganccatc | 479 |

<210> SEQ ID NO 98
<211> LENGTH: 461
<212> TYPE: DNA
<213> ORGANISM: Homo sapien

<400> SEQUENCE: 98

| agtgacttgt cctccaacaa aaccccttga tcaagtttgt ggcactgaca atcagaccta | 60 |
| tgctagttcc tgtcatctat tcgctactaa atgcagactg gagggacca aaaagggca | 120 |

| | |
|---|---:|
| tcaactccag ctggattatt ttggagcctg caaatctatt cctacttgta cggactttga | 180 |
| agtgattcag tttcctctac ggatgagaga ctggctcaag aatatcctca tgcagcttta | 240 |
| tgaagccact ctgaacacgc tggttatcta gatgagaaca gagaaataaa gtcagaaaat | 300 |
| ttacctggag aaaagaggct ttggctgggg accatcccat tgaaccttct cttaaggact | 360 |
| ttaagaaaaa ctaccacatg ttgtgtatcc tggtgccggc cgtttatgaa ctgaccaccc | 420 |
| tttggaataa tcttgacgct cctgaacttg ctcctctgcg a | 461 |

<210> SEQ ID NO 99
<211> LENGTH: 171
<212> TYPE: DNA
<213> ORGANISM: Homo sapien

<400> SEQUENCE: 99

| | |
|---|---:|
| gtggccgcgc gcaggtgttt cctcgtaccg cagggccccc tcccttcccc aggcgtccct | 60 |
| cggcgcctct gcgggcccga ggaggagcgg ctggcgggtg gggggagtgt gacccaccct | 120 |
| cggtgagaaa agccttctct agcgatctga gaggcgtgcc ttgggggtac c | 171 |

<210> SEQ ID NO 100
<211> LENGTH: 269
<212> TYPE: DNA
<213> ORGANISM: Homo sapien

<400> SEQUENCE: 100

| | |
|---|---:|
| cggccgcaag tgcaactcca gctggggccg tgcggacgaa gattctgcca gcagttggtc | 60 |
| cgactgcgac gacggcggcg gcgacagtcg caggtgcagc gcgggcgcct ggggtcttgc | 120 |
| aaggctgagc tgacgccgca gaggtcgtgt cacgtccac gaccttgacg ccgtcgggga | 180 |
| cagccggaac agagcccggt gaagcgggag gcctcgggga gccctcgggg aagggcggcc | 240 |
| cgagagatac gcaggtgcag gtggccgcc | 269 |

<210> SEQ ID NO 101
<211> LENGTH: 405
<212> TYPE: DNA
<213> ORGANISM: Homo sapien

<400> SEQUENCE: 101

| | |
|---|---:|
| tttttttttt ttttggaatc tactgcgagc acagcaggtc agcaacaagt ttattttgca | 60 |
| gctagcaagg taacagggta ggcatggtt acatgttcag gtcaacttcc tttgtcgtgg | 120 |
| ttgattggtt tgtctttatg ggggcggggt gggtagggg aaacgaagca aataacatgg | 180 |
| agtgggtgca ccctccctgt agaacctggt tacaaagctt ggggcagttc acctggtctg | 240 |
| tgaccgtcat tttcttgaca tcaatgttat tagaagtcag gatatctttt agagagtcca | 300 |
| ctgttctgga gggagattag ggtttcttgc caaatccaac aaaatccact gaaaagttg | 360 |
| gatgatcagt acgaataccg aggcatattc tcatatcggt ggcca | 405 |

<210> SEQ ID NO 102
<211> LENGTH: 470
<212> TYPE: DNA
<213> ORGANISM: Homo sapien

<400> SEQUENCE: 102

| | |
|---|---:|
| tttttttttt tttttttttt tttttttttt tttttttttt tttttttttt tttttttttt | 60 |
| ggcacttaat ccattttat ttcaaaatgt ctacaaattt aatcccatta tacggtattt | 120 |
| tcaaaatcta aattattcaa attagccaaa tccttaccaa ataataccca aaaatcaaaa | 180 |

| | |
|---|---|
| atatacttct tcagcaaac ttgttacata aattaaaaaa atatatacgg ctggtgtttt | 240 |
| caaagtacaa ttatcttaac actgcaaaca ttttaaggaa ctaaaataaa aaaaaacact | 300 |
| ccgcaaaggt taaagggaac aacaaattct tttacaacac cattataaaa atcatatctc | 360 |
| aaatcttagg ggaatatata cttcacacgg gatcttaact tttactcact ttgttttattt | 420 |
| ttttaaacca ttgtttgggc ccaacacaat ggaatccccc ctggactagt | 470 |

<210> SEQ ID NO 103
<211> LENGTH: 581
<212> TYPE: DNA
<213> ORGANISM: Homo sapien

<400> SEQUENCE: 103

| | |
|---|---|
| tttttttttt ttttttttga ccccctctt ataaaaaaca agttaccatt ttattttact | 60 |
| tacacatatt tattttataa ttggtattag atattcaaaa ggcagctttt aaaatcaaac | 120 |
| taaatggaaa ctgccttaga tacataattc ttaggaatta gcttaaaatc tgcctaaagt | 180 |
| gaaaatcttc tctagctctt ttgactgtaa attttgact cttgtaaaac atccaaattc | 240 |
| attttcttg tctttaaaat tatctaatct ttccattttt tccctattcc aagtcaattt | 300 |
| gcttctctag cctcatttcc tagctcttat ctactattag taagtggctt ttttcctaaa | 360 |
| agggaaaaca ggaagagaaa tggcacacaa aacaaacatt ttatattcat atttctacct | 420 |
| acgttaataa aatagcattt tgtgaagcca gctcaaaaga aggcttagat cctttatgt | 480 |
| ccattttagt cactaaacga tatcaaagtg ccagaatgca aaaggtttgt gaacatttat | 540 |
| tcaaaagcta atataagata tttcacatac tcatctttct g | 581 |

<210> SEQ ID NO 104
<211> LENGTH: 578
<212> TYPE: DNA
<213> ORGANISM: Homo sapien

<400> SEQUENCE: 104

| | |
|---|---|
| tttttttttt tttttttttt ttttctctt ctttttttt gaaatgagga tcgagttttt | 60 |
| cactctctag atagggcatg aagaaaactc atctttccag ctttaaaata acaatcaaat | 120 |
| ctcttatgct atatcatatt ttaagttaaa ctaatgagtc actggcttat cttcctga | 180 |
| aggaaatctg ttcattcttc tcattcatat agttatatca agtactacct tgcatattga | 240 |
| gaggttttc ttctctattt acacatatat ttccatgtga atttgtatca aacctttatt | 300 |
| ttcatgcaaa ctagaaaata atgtttcttt tgcataagag aagagaacaa tatagcatta | 360 |
| caaaactgct caaattgttt gttaagttat ccattataat tagttggcag gagctaatac | 420 |
| aaatcacatt tacgacagca ataataaaac tgaagtacca gttaaatatc caaataatt | 480 |
| aaaggaacat tttagcctg ggtataatta gctaattcac tttacaagca tttattagaa | 540 |
| tgaattcaca tgttattatt cctagcccaa cacaatgg | 578 |

<210> SEQ ID NO 105
<211> LENGTH: 538
<212> TYPE: DNA
<213> ORGANISM: Homo sapien

<400> SEQUENCE: 105

| | |
|---|---|
| tttttttttt tttttcagta ataatcagaa caatatttat ttttatattt aaaattcata | 60 |
| gaaaagtgcc ttcacttaa taaagtttg tttctcaaag tgatcagagg aattagatat | 120 |
| gtcttgaaca ccaatattaa tttgaggaaa atacaccaaa atacattaag taaattattt | 180 |

-continued

```
aagatcatag agcttgtaag tgaaaagata aaatttgacc tcagaaactc tgagcattaa      240
aaatccacta ttagcaaata aattactatg gacttcttgc tttaattttg tgatgaatat      300
ggggtgtcac tggtaaacca acacattctg aaggatacat tacttagtga tagattctta      360
tgtactttgc taatacgtgg atatgagttg acaagtttct ctttcttcaa tcttttaagg      420
ggcgagaaat gaggaagaaa agaaaaggat tacgcatact gttctttcta tggaaggatt      480
agatatgttt cctttgccaa tattaaaaaa ataataatgt ttactactag tgaaaccc       538
```

<210> SEQ ID NO 106
<211> LENGTH: 473
<212> TYPE: DNA
<213> ORGANISM: Homo sapien

<400> SEQUENCE: 106

```
tttttttttt ttttttagtc aagtttctat ttttattata attaaagtct tggtcatttc       60
atttattagc tctgcaactt acatatttaa attaaagaaa cgttttagac aactgtacaa      120
tttataaatg taaggtgcca ttattgagta atatattcct ccaagagtgg atgtgtccct      180
tctcccacca actaatgaac agcaacatta gtttaatttt attagtagat atacactgct      240
gcaaacgcta attctcttct ccatccccat gtgatattgt gtatatgtgt gagttggtag      300
aatgcatcac aatctacaat caacagcaag atgaagctag gctgggcttt cggtgaaaat      360
agactgtgtc tgtctgaatc aaatgatctg acctatcctc ggtggcaaga actcttcgaa      420
ccgcttcctc aaaggcgctg ccacatttgt ggctctttgc acttgtttca aaa             473
```

<210> SEQ ID NO 107
<211> LENGTH: 1621
<212> TYPE: DNA
<213> ORGANISM: Homo sapien

<400> SEQUENCE: 107

```
cgccatggca ctgcagggca tctcggtcat ggagctgtcc ggcctggccc cgggcccgtt       60
ctgtgctatg gtcctggctg acttcggggc gcgtgtggta cgcgtggacc ggcccggctc      120
ccgctacgac gtgagccgct tgggccgggg caagcgctcg ctagtgctgg acctgaagca      180
gccgcgggga gccgccgtgc tgcggcgtct gtgcaagcgg tcggatgtgc tgctggagcc      240
cttccgccgc ggtgtcatgg agaaaactcca gctgggccca gagattctgc agcgggaaaa      300
tccaaggctt atttatgcca ggctgagtgg atttggccag tcaggaagct tctgccggtt      360
agctggccac gatatcaact atttggcttt gtcaggtgtt ctctcaaaaa ttggcagaag      420
tggtgagaat ccgtatgccc cgctgaatct cctggctgac tttgctggtg gtggccttat      480
gtgtgcactg gcattataa tggctctttt tgaccgcaca cgcactgaca agggtcaggt      540
cattgatgca aatatggtgg aaggaacagc atatttaagt tcttttctgt ggaaaactca      600
gaaatcgagt ctgtgggaag cacctcgagg acagaacatg ttggatggtg gagcaccttt      660
ctatacgact tacaggacag cagatgggga attcatggct gttggagcaa tagaacccca      720
gttctacgag ctgctgatca aaggacttgg actaaagtct gatgaacttc ccaatcagat      780
gagcatggat gattggccag aaatgaagaa gaagtttgca gatgtatttg caagaagac       840 gaaggcagag tggtgtcaaa tctttgacgg cacagatgcc tgtgtgactc cggttctgac      900
ttttgaggag gttgttcatc atgatcacaa caaggaacgg ggctcgttta tcaccagtga      960
ggagcaggac gtgagccccc gcctgcacc tctgctgtta aacacccag ccatcccttc      1020 tttcaaaagg gatcctttca taggagaaca cactgaggag atacttgaag aatttggatt      1080
```

```
cagccgcgaa gagatttatc agcttaactc agataaaatc attgaaagta ataaggtaaa      1140
agctagtctc taacttccag gcccacggct caagtgaatt tgaatactgc atttacagtg      1200
tagagtaaca cataacattg tatgcatgga acatggagg aacagtatta cagtgtccta       1260
ccactctaat caagaaaaga attacagact ctgattctac agtgatgatt gaattctaaa      1320
aatggttatc attagggctt ttgatttata aactttggg tacttatact aaattatggt       1380
agttattctg ccttccagtt tgcttgatat atttgttgat attaagattc ttgacttata      1440
ttttgaatgg gttctagtga aaaggaatg atatattctt gaagacatcg atatacattt       1500
atttacactc ttgattctac aatgtagaaa atgaggaaat gccacaaatt gtatggtgat      1560
aaaagtcacg tgaaacaaaa aaaaaaaaaa aaaaaaaaaa aaaaaaaaaa aaaaaaaaaa      1620
a                                                                     1621
```

<210> SEQ ID NO 108
<211> LENGTH: 382
<212> TYPE: PRT
<213> ORGANISM: Homo sapien

<400> SEQUENCE: 108

```
Met Ala Leu Gln Gly Ile Ser Val Met Glu Leu Ser Gly Leu Ala Pro
 1               5                  10                  15
Gly Pro Phe Cys Ala Met Val Leu Ala Asp Phe Gly Ala Arg Val Val
                20                  25                  30
Arg Val Asp Arg Pro Gly Ser Arg Tyr Asp Val Ser Arg Leu Gly Arg
            35                  40                  45
Gly Lys Arg Ser Leu Val Leu Asp Leu Lys Gln Pro Arg Gly Ala Ala
        50                  55                  60
Val Leu Arg Arg Leu Cys Lys Arg Ser Asp Val Leu Leu Glu Pro Phe
    65                  70                  75                  80
Arg Arg Gly Val Met Glu Lys Leu Gln Leu Gly Pro Glu Ile Leu Gln
                    85                  90                  95
Arg Glu Asn Pro Arg Leu Ile Tyr Ala Arg Leu Ser Gly Phe Gly Gln
                100                 105                 110
Ser Gly Ser Phe Cys Arg Leu Ala Gly His Asp Ile Asn Tyr Leu Ala
            115                 120                 125
Leu Ser Gly Val Leu Ser Lys Ile Gly Arg Ser Gly Glu Asn Pro Tyr
        130                 135                 140
Ala Pro Leu Asn Leu Leu Ala Asp Phe Ala Gly Gly Leu Met Cys
145                 150                 155                 160
Ala Leu Gly Ile Ile Met Ala Leu Phe Asp Arg Thr Arg Thr Asp Lys
                    165                 170                 175
Gly Gln Val Ile Asp Ala Asn Met Val Glu Gly Thr Ala Tyr Leu Ser
                180                 185                 190
Ser Phe Leu Trp Lys Thr Gln Lys Ser Ser Leu Trp Glu Ala Pro Arg
            195                 200                 205
Gly Gln Asn Met Leu Asp Gly Ala Pro Phe Tyr Thr Thr Tyr Arg
        210                 215                 220
Thr Ala Asp Gly Glu Phe Met Ala Val Gly Ala Ile Glu Pro Gln Phe
225                 230                 235                 240
Tyr Glu Leu Leu Ile Lys Gly Leu Gly Leu Lys Ser Asp Glu Leu Pro
                    245                 250                 255
Asn Gln Met Ser Met Asp Asp Trp Pro Glu Met Lys Lys Lys Phe Ala
                260                 265                 270
```

```
Asp Val Phe Ala Lys Lys Thr Lys Ala Glu Trp Cys Gln Ile Phe Asp
            275                 280                 285
Gly Thr Asp Ala Cys Val Thr Pro Val Leu Thr Phe Glu Glu Val Val
        290                 295                 300
His His Asp His Asn Lys Glu Arg Gly Ser Phe Ile Thr Ser Glu Glu
305                 310                 315                 320
Gln Asp Val Ser Pro Arg Pro Ala Pro Leu Leu Leu Asn Thr Pro Ala
                325                 330                 335
Ile Pro Ser Phe Lys Arg Asp Pro Phe Ile Gly Glu His Thr Glu Glu
            340                 345                 350
Ile Leu Glu Glu Phe Gly Phe Ser Arg Glu Glu Ile Tyr Gln Leu Asn
        355                 360                 365
Ser Asp Lys Ile Ile Glu Ser Asn Lys Val Lys Ala Ser Leu
370                 375                 380

<210> SEQ ID NO 109
<211> LENGTH: 1524
<212> TYPE: DNA
<213> ORGANISM: Homo sapien

<400> SEQUENCE: 109
ggcacgaggc tgcgccaggg cctgagcgga ggcggggca gcctcgccag cggggcccc       60 gggcctggcc atgcctcact gagccagcgc ctgcgcctct acctcgccga cagctggaac    120
cagtgcgacc tagtggctct cacctgcttc ctcctgggcg tgggctgccg gctgaccccg    180
ggtttgtacc acctgggccg cactgtcctc tgcatcgact tcatggtttt cacggtgcgg    240
ctgcttcaca tcttcacggt caacaaacag ctggggccca agatcgtcat cgtgagcaag    300
atgatgaagg acgtgttctt cttcctcttc ttcctcggcg tgtggctggt agcctatggc    360
gtggccacgg aggggctcct gaggccacgg gacagtgact cccaagtat cctgcgccgc     420 gtcttctacc gtccctacct gcagatcttc gggcagattc cccaggagga catggacgtg    480
gccctcatgg agcacagcaa ctgctcgtcg gagcccggct ctgggcaca ccctcctggg     540 gcccaggcgg gcacctgcgt ctcccagtat gccaactggc tggtggtgct gctcctcgtc    600
atcttcctgc tcgtggccaa catcctgctg gtcaacttgc tcattgccat gttcagttac    660
acattcggca agtacagggg caacagcgat ctctactgga aggcgcagcg ttaccgcctc    720
atccgggaat tccactctcg gcccgcgctg gccccgccct ttatcgtcat ctcccacttg    780
cgcctcctgc tcaggcaatt gtgcaggcga ccccggagcc cccagccgtc ctccccggcc    840
ctcgagcatt tccgggttta cctttctaag gaagccgagc ggaagctgct aacgtgggaa    900
tcggtgcata aggagaactt tctgctggca cgcgctaggg acaagcggga gagcgactcc    960
gagcgtctga gcgcacgtc ccagaaggtg acttggcac tgaaacagct gggacacatc     1020
cgcgagtacg aacagcgcct gaaagtgctg agcggggagg tccagcagtg tagccgcgtc    1080
ctggggtggg tggccgaggc cctgagccgc tctgccttgc tgccccagg tgggccgcca    1140 cccctgacc tgcctgggtc caaagactga gccctgctgg cggacttcaa ggagaagccc     1200 ccacaggga ttttgctcct agagtaaggc tcatctgggc ctcggccccc gcacctggtg     1260
gccttgtcct tgaggtgagc ccatgtccca tctgggccac tgtcaggacc acctttggga    1320
gtgtcatcct tacaaaccac agcatgcccg gctcctccca gaaccagtcc cagcctggga    1380
ggatcaaggc ctggatcccg ggccgttatc catctggagg ctgcagggtc cttggggtaa    1440
```

| | | |
|---|---|---|
| cagggaccac agacccctca ccactcacag attcctcaca ctggggaaat aaagccattt | 1500 |
| cagaggaaaa aaaaaaaaaa aaaa | 1524 |

<210> SEQ ID NO 110
<211> LENGTH: 3410
<212> TYPE: DNA
<213> ORGANISM: Homo sapien

<400> SEQUENCE: 110

| | | |
|---|---|---|
| gggaaccagc ctgcacgcgc tggctccggg tgacagccgc gcgcctcggc caggatctga | 60 |
| gtgatgagac gtgtccccac tgaggtgccc cacagcagca ggtgttgagc atgggctgag | 120 |
| aagctggacc ggcaccaaag ggctggcaga atgggcgcc tggctgattc ctaggcagtt | 180 |
| ggcggcagca aggaggagag gccgcagctt ctggagcaga gccgagacga agcagttctg | 240 |
| gagtgcctga acggccccct gagccctacc cgcctggccc actatggtcc agaggctgtg | 300 |
| ggtgagccgc ctgctgcggc accggaaagc ccagctcttg ctggtcaacc tgctaacctt | 360 |
| tggcctggag gtgtgtttgg ccgcaggcat cacctatgtg ccgcctctgc tgctggaagt | 420 |
| gggggtagag gagaagttca tgaccatggt gctgggcatt ggtccagtgc tgggcctggt | 480 |
| ctgtgtcccg ctcctaggct cagccagtga ccactggcgt ggacgctatg ccgccgccg | 540 |
| gcccttcatc tggcactgt ccttgggcat cctgctgagc ctctttctca tcccaagggc | 600 |
| cggctggcta gcagggctgc tgtgcccgga tcccaggccc ctggagctgg cactgctcat | 660 |
| cctgggcgtg gggctgctgg acttctgtgg ccaggtgtgc ttcactccac tggaggccct | 720 |
| gctctctgac ctcttccggg acccggacca ctgtcgccag gcctactctg tctatgcctt | 780 |
| catgatcagt cttgggggct gcctgggcta cctcctgcct gccattgact gggacaccag | 840 |
| tgccctggcc ccctacctgg gcacccagga ggagtgcctc tttggcctgc tcaccctcat | 900 |
| cttcctcacc tgcgtagcag ccacactgct ggtggctgag gaggcagcgc tgggccccac | 960 |
| cgagccagca gaagggctgt cggccccctc cttgtcgccc cactgctgtc catgccgggc | 1020 |
| ccgcttggct ttccggaacc tgggcgccct gcttccccgg ctgcaccagc tgtgctgccg | 1080 |
| catgccccgc accctgcgcc ggctcttcgt ggctgagctg tgcagctgga tggcactcat | 1140 |
| gaccttcacg ctgttttaca cggatttcgt gggcgagggg ctgtaccagg gcgtgcccag | 1200 |
| agctgagccg ggcaccgagg cccggagaca ctatgatgaa ggcgttcgga tgggcagcct | 1260 |
| ggggctgttc ctgcagtgcg ccatctccct ggtcttctct ctggtcatgg accggctggt | 1320 |
| gcagcgattc ggcactcgag cagtctattt ggccagtgtg cagctttcc ctgtggctgc | 1380 |
| cggtgccaca tgcctgtccc acagtgtggc cgtggtgaca gcttcagccg ccctcaccgg | 1440 |
| gttcaccttc tcagccctgc agatcctgcc ctacacactg gcctccctct accaccggga | 1500 |
| gaagcaggtg ttcctgccca ataccgagg ggacactgga ggtgctagca gtgaggacag | 1560 |
| cctgatgacc agcttcctgc caggccctaa gcctggagct cccttcccta atggacacgt | 1620 |
| gggtgctgga ggcagtggcc tgctcccacc tccacccgcg ctctgcgggg cctctgcctg | 1680 |
| tgatgtctcc gtacgtgtgg tggtgggtga gcccaccgag gccagggtgg ttccgggccg | 1740 |
| ggcatctgc ctggacctcg ccatcctgga tagtgccttc ctgctgtccc aggtggcccc | 1800 |
| atccctgttt atgggctcca ttgtccagct cagccagtct gtcactgcct atatggtgtc | 1860 |
| tgccgcaggc ctgggtctgg tcgccatttta ctttgctaca caggtagtat ttgacaagag | 1920 |
| cgacttggcc aaatactcag cgtagaaaac ttccagcaca ttgggtgga gggcctgcct | 1980 |
| cactgggtcc cagctccccg ctcctgttag ccccatgggg ctgccgggct ggccgccagt | 2040 |

```
ttctgttgct gccaaagtaa tgtggctctc tgctgccacc ctgtgctgct gaggtgcgta   2100
gctgcacagc tgggggctgg ggcgtccctc tcctctctcc ccagtctcta gggctgcctg   2160
actggaggcc ttccaagggg gtttcagtct ggacttatac agggaggcca gaagggctcc   2220
atgcactgga atgcggggac tctgcaggtg gattacccag gctcagggtt aacagctagc   2280
ctcctagttg agacacacct agagaagggt ttttgggagc tgaataaact cagtcacctg   2340
gtttcccatc tctaagcccc ttaacctgca gcttcgttta atgtagctct tgcatgggag   2400
tttctaggat gaaacactcc tccatgggat ttgaacatat gacttatttg taggggaaga   2460
gtcctgaggg gcaacacaca agaaccaggt cccctcagcc cacagcactg tcttttttgct  2520 gatccacccc cctcttacct tttatcagga tgtggcctgt tggtccttct gttgccatca   2580
cagagacaca ggcatttaaa tatttaactt atttatttaa caaagtagaa gggaatccat   2640
tgctagcttt tctgtgttgg tgtctaatat ttgggtaggg tgggggatcc ccaacaatca   2700
ggtcccctga gatagctggt cattgggctg atcattgcca gaatcttctt ctcctggggt   2760
ctggcccccc aaaatgccta acccaggacc ttggaaattc tactcatccc aaatgataat   2820
tccaaatgct gttacccaag gttagggtgt tgaaggaagg tagagggtgg ggcttcaggt   2880
ctcaacggct tccctaacca ccctcttct cttggcccag cctggttccc cccacttcca    2940
ctcccctcta ctctctctag gactgggctg atgaaggcac tgcccaaaat ttcccctacc   3000
cccaactttc ccctaccccc aactttcccc accagctcca caaccctgtt tggagctact   3060
gcaggaccag aagcacaaag tgcggtttcc caagcctttg tccatctcag cccccagagt   3120
atatctgtgc ttggggaatc tcacacagaa actcaggagc accccctgcc tgagctaagg   3180
gaggtcttat ctctcagggg gggtttaagt gccgtttgca ataatgtcgt cttatttatt   3240
tagcggggtg aatattttat actgtaagtg agcaatcaga gtataatgtt tatggtgaca   3300
aaattaaagg ctttcttata tgtttaaaaa aaaaaaaaa aaaaaaaaaa aaaaaaaaa    3360 aaaaaaara aaaaaaaaa aaaaaaaaaa aaaaaataa aaaaaaaaa              3410
```

<210> SEQ ID NO 111
<211> LENGTH: 1289
<212> TYPE: DNA
<213> ORGANISM: Homo sapien

<400> SEQUENCE: 111

```
agccaggcgt ccctctgcct gcccactcag tggcaacacc cgggagctgt tttgtccttt    60
gtggagcctc agcagttccc tctttcagaa ctcactgcca agagccctga acaggagcca   120
ccatgcagtg cttcagcttc attaagacca tgatgatcct cttcaatttg ctcatctttc   180
tgtgtggtgc agccctgttg gcagtgggca tctgggtgtc aatcgatggg gcatcctttc   240
tgaagatctt cgggccactg tcgtccagtc catgcagtt tgtcaacgtg ggctacttcc    300
tcatcgcagc cggcgttgtg gtcttttgctc ttggtttcct gggctgctat ggtgctaaga   360
ctgagagcaa gtgtgccctc gtgacgttct tcttcatcct cctcctcatc ttcattgctg    420
aggttgcagc tgctgtggtc gccttggtgt acaccacaat ggctgagcac ttcctgacgt   480
tgctggtagt gcctgccatc aagaaagatt atggttccca ggaagacttc actcaagtgt   540
ggaacaccac catgaaaggg ctcaagtgct gtggcttcac caactatcg gattttgagg    600 actcacccta cttcaaagag aacagtgcct ttccccatt ctgttgcaat gacaacgtca   660
ccaacacagc caatgaaacc tgcaccaagc aaaaggctca cgaccaaaaa gtagagggtt   720
gcttcaatca gcttttgtat gacatccgaa ctaatgcagt caccgtgggt ggtgtggcag    780
```

-continued

```
ctggaattgg gggcctcgag ctggctgcca tgattgtgtc catgtatctg tactgcaatc    840
tacaataagt ccacttctgc ctctgccact actgctgcca catgggaact gtgaagaggc    900
accctggcaa gcagcagtga ttggggagg ggacaggatc taacaatgtc acttgggcca     960
gaatggacct gcccttctg ctccagactt ggggctagat agggaccact ccttttagcg    1020
atgcctgact ttccttccat tggtgggtgg atgggtgggg ggcattccag agcctctaag   1080
gtagccagtt ctgttgccca ttcccccagt ctattaaacc cttgatatgc ccctaggcc    1140 tagtggtgat cccagtgctc tactggggga tgagagaaag gcatttata gcctgggcat    1200 aagtgaaatc agcagagcct ctgggtggat gtgtagaagg cacttcaaaa tgcataaacc   1260
tgttacaatg ttaaaaaaaa aaaaaaaa                                      1289
```

<210> SEQ ID NO 112
<211> LENGTH: 315
<212> TYPE: PRT
<213> ORGANISM: Homo sapien

<400> SEQUENCE: 112

```
Met Val Phe Thr Val Arg Leu Leu His Ile Phe Thr Val Asn Lys Gln
 1               5                  10                  15

Leu Gly Pro Lys Ile Val Ile Ser Lys Met Met Lys Asp Val Phe
            20                  25                  30

Phe Phe Leu Phe Phe Leu Gly Val Trp Leu Val Ala Tyr Gly Val Ala
        35                  40                  45

Thr Glu Gly Leu Leu Arg Pro Arg Asp Ser Asp Phe Pro Ser Ile Leu
    50                  55                  60

Arg Arg Val Phe Tyr Arg Pro Tyr Leu Gln Ile Phe Gly Gln Ile Pro
65                  70                  75                  80

Gln Glu Asp Met Asp Val Ala Leu Met Glu His Ser Asn Cys Ser Ser
                85                  90                  95

Glu Pro Gly Phe Trp Ala His Pro Pro Gly Ala Gln Ala Gly Thr Cys
            100                 105                 110

Val Ser Gln Tyr Ala Asn Trp Leu Val Val Leu Leu Val Ile Phe
        115                 120                 125

Leu Leu Val Ala Asn Ile Leu Leu Val Asn Leu Leu Ile Ala Met Phe
    130                 135                 140

Ser Tyr Thr Phe Gly Lys Val Gln Gly Asn Ser Asp Leu Tyr Trp Lys
145                 150                 155                 160

Ala Gln Arg Tyr Arg Leu Ile Arg Glu Phe His Ser Arg Pro Ala Leu
                165                 170                 175

Ala Pro Pro Phe Ile Val Ile Ser His Leu Arg Leu Leu Leu Arg Gln
            180                 185                 190

Leu Cys Arg Arg Pro Arg Ser Pro Gln Pro Ser Ser Pro Ala Leu Glu
        195                 200                 205

His Phe Arg Val Tyr Leu Ser Lys Glu Ala Glu Arg Lys Leu Leu Thr
    210                 215                 220

Trp Glu Ser Val His Lys Glu Asn Phe Leu Leu Ala Arg Ala Arg Asp
225                 230                 235                 240

Lys Arg Glu Ser Asp Ser Glu Arg Leu Lys Arg Thr Ser Gln Lys Val
                245                 250                 255

Asp Leu Ala Leu Lys Gln Leu Gly His Ile Arg Glu Tyr Glu Gln Arg
            260                 265                 270

Leu Lys Val Leu Glu Arg Glu Val Gln Gln Cys Ser Arg Val Leu Gly
        275                 280                 285
```

```
Trp Val Ala Glu Ala Leu Ser Arg Ser Ala Leu Leu Pro Pro Gly Gly
290                 295                 300

Pro Pro Pro Asp Leu Pro Gly Ser Lys Asp
305             310             315

<210> SEQ ID NO 113
<211> LENGTH: 553
<212> TYPE: PRT
<213> ORGANISM: Homo sapien

<400> SEQUENCE: 113

Met Val Gln Arg Leu Trp Val Ser Arg Leu Leu Arg His Arg Lys Ala
 1               5                  10                  15

Gln Leu Leu Val Asn Leu Leu Thr Phe Gly Leu Glu Val Cys Leu
            20                  25                  30

Ala Ala Gly Ile Thr Tyr Val Pro Pro Leu Leu Glu Val Gly Val
                35                  40                  45

Glu Glu Lys Phe Met Thr Met Val Leu Gly Ile Gly Pro Val Leu Gly
 50                  55                  60

Leu Val Cys Val Pro Leu Leu Gly Ser Ala Ser Asp His Trp Arg Gly
 65                  70                  75                  80

Arg Tyr Gly Arg Arg Pro Phe Ile Trp Ala Leu Ser Leu Gly Ile
                85                  90                  95

Leu Leu Ser Leu Phe Leu Ile Pro Arg Ala Gly Trp Leu Ala Gly Leu
                100                 105                 110

Leu Cys Pro Asp Pro Arg Pro Leu Glu Leu Ala Leu Leu Ile Leu Gly
                115                 120                 125

Val Gly Leu Leu Asp Phe Cys Gly Gln Val Cys Phe Thr Pro Leu Glu
130                 135                 140

Ala Leu Leu Ser Asp Leu Phe Arg Asp Pro Asp His Cys Arg Gln Ala
145                 150                 155                 160

Tyr Ser Val Tyr Ala Phe Met Ile Ser Leu Gly Gly Cys Leu Gly Tyr
                165                 170                 175

Leu Leu Pro Ala Ile Asp Trp Asp Thr Ser Ala Leu Ala Pro Tyr Leu
                180                 185                 190

Gly Thr Gln Glu Glu Cys Leu Phe Gly Leu Leu Thr Leu Ile Phe Leu
                195                 200                 205

Thr Cys Val Ala Ala Thr Leu Leu Val Ala Glu Glu Ala Ala Leu Gly
210                 215                 220

Pro Thr Glu Pro Ala Glu Gly Leu Ser Ala Pro Ser Leu Ser Pro His
225                 230                 235                 240

Cys Cys Pro Cys Arg Ala Arg Leu Ala Phe Arg Asn Leu Gly Ala Leu
                245                 250                 255

Leu Pro Arg Leu His Gln Leu Cys Cys Arg Met Pro Arg Thr Leu Arg
                260                 265                 270

Arg Leu Phe Val Ala Glu Leu Cys Ser Trp Met Ala Leu Met Thr Phe
                275                 280                 285

Thr Leu Pro Tyr Thr Asp Phe Val Gly Glu Gly Leu Tyr Gln Gly Val
                290                 295                 300

Pro Arg Ala Glu Pro Gly Thr Glu Ala Arg His Tyr Asp Glu Gly
305                 310                 315                 320

Val Arg Met Gly Ser Leu Gly Leu Phe Leu Gln Cys Ala Ile Ser Leu
                325                 330                 335

Val Phe Ser Leu Val Met Asp Arg Leu Val Gln Arg Phe Gly Thr Arg
                340                 345                 350
```

```
Ala Val Tyr Leu Ala Ser Val Ala Phe Pro Val Ala Gly Ala
        355                 360                 365

Thr Cys Leu Ser His Ser Val Ala Val Thr Ala Ser Ala Ala Leu
    370                 375                 380

Thr Gly Phe Thr Phe Ser Ala Leu Gln Ile Leu Pro Tyr Thr Leu Ala
385                 390                 395                 400

Ser Leu Tyr His Arg Glu Lys Gln Val Phe Leu Pro Lys Tyr Arg Gly
                405                 410                 415

Asp Thr Gly Gly Ala Ser Ser Glu Asp Ser Leu Met Thr Ser Phe Leu
                420                 425                 430

Pro Gly Pro Lys Pro Gly Ala Pro Phe Pro Asn Gly His Val Gly Ala
                435                 440                 445

Gly Gly Ser Gly Leu Leu Pro Pro Pro Ala Leu Cys Gly Ala Ser
                450                 455                 460

Ala Cys Asp Val Ser Val Arg Val Val Gly Glu Pro Thr Glu Ala
465                 470                 475                 480

Arg Val Val Pro Gly Arg Gly Ile Cys Leu Asp Leu Ala Ile Leu Asp
                485                 490                 495

Ser Ala Phe Leu Leu Ser Gln Val Ala Pro Ser Leu Phe Met Gly Ser
                500                 505                 510

Ile Val Gln Leu Ser Gln Ser Val Thr Ala Tyr Met Val Ser Ala Ala
                515                 520                 525

Gly Leu Gly Leu Val Ala Ile Tyr Phe Ala Thr Gln Val Val Phe Asp
                530                 535                 540

Lys Ser Asp Leu Ala Lys Tyr Ser Ala
545                 550

<210> SEQ ID NO 114
<211> LENGTH: 241
<212> TYPE: PRT
<213> ORGANISM: Homo sapien

<400> SEQUENCE: 114

Met Gln Cys Phe Ser Phe Ile Lys Thr Met Met Ile Leu Phe Asn Leu
  1               5                  10                  15

Leu Ile Phe Leu Cys Gly Ala Ala Leu Leu Ala Val Gly Ile Trp Val
                 20                  25                  30

Ser Ile Asp Gly Ala Ser Phe Leu Lys Ile Phe Gly Pro Leu Ser Ser
                 35                  40                  45

Ser Ala Met Gln Phe Val Asn Val Gly Tyr Phe Leu Ile Ala Ala Gly
         50                  55                  60

Val Val Val Phe Ala Leu Gly Phe Leu Gly Cys Tyr Gly Ala Lys Thr
 65                  70                  75                  80

Glu Ser Lys Cys Ala Leu Val Thr Phe Phe Ile Leu Leu Leu Ile
                 85                  90                  95

Phe Ile Ala Glu Val Ala Ala Ala Val Val Ala Leu Val Tyr Thr Thr
                100                 105                 110

Met Ala Glu His Phe Leu Thr Leu Leu Val Val Pro Ala Ile Lys Lys
            115                 120                 125

Asp Tyr Gly Ser Gln Glu Asp Phe Thr Gln Val Trp Asn Thr Thr Met
        130                 135                 140

Lys Gly Leu Lys Cys Cys Gly Phe Thr Asn Tyr Thr Asp Phe Glu Asp
145                 150                 155                 160

Ser Pro Tyr Phe Lys Glu Asn Ser Ala Phe Pro Pro Phe Cys Cys Asn
                165                 170                 175
```

| Asp | Asn | Val | Thr | Asn | Thr | Ala | Asn | Glu | Thr | Cys | Thr | Lys | Gln | Lys | Ala |
|||| 180 ||||| 185 ||||| 190 |||

| His | Asp | Gln | Lys | Val | Glu | Gly | Cys | Phe | Asn | Gln | Leu | Leu | Tyr | Asp | Ile |
||||| 195 ||||| 200 ||||| 205 ||

| Arg | Thr | Asn | Ala | Val | Thr | Val | Gly | Gly | Val | Ala | Ala | Gly | Ile | Gly | Gly |
|||| 210 ||||| 215 ||||| 220 |||

| Leu | Glu | Leu | Ala | Ala | Met | Ile | Val | Ser | Met | Tyr | Leu | Tyr | Cys | Asn | Leu |
| 225 |||||| 230 ||||| 235 |||| 240 |

Gln

<210> SEQ ID NO 115
<211> LENGTH: 366
<212> TYPE: DNA
<213> ORGANISM: Homo sapien

<400> SEQUENCE: 115

```
gctctttctc tcccctcctc tgaatttaat tctttcaact tgcaatttgc aaggattaca        60
catttcactg tgatgtatat tgtgttgcaa aaaaaaaaa gtgtctttgt ttaaaattac       120
ttggtttgtg aatccatctt gcttttccc cattggaact agtcattaac ccatctctga       180
actggtagaa aaacatctga agagctagtc tatcagcatc tgacaggtga attggatggt       240
tctcagaacc atttcaccca gacagcctgt ttctatcctg tttaataaat tagtttgggt       300
tctctacatg cataacaaac cctgctccaa tctgtcacat aaaagtctgt gacttgaagt       360
ttagtc                                                                 366
```

<210> SEQ ID NO 116
<211> LENGTH: 282
<212> TYPE: DNA
<213> ORGANISM: Homo sapien
<220> FEATURE:
<221> NAME/KEY: misc_feature
<222> LOCATION: (1)...(282)
<223> OTHER INFORMATION: n = A,T,C or G

<400> SEQUENCE: 116

```
acaaagatga accatttcct atattatagc aaaattaaaa tctacccgta ttctaatatt        60
gagaaatgag atnaaacaca atnttataaa gtctacttag agaagatcaa gtgacctcaa       120
agactttact attttcatat tttaagacac atgatttatc ctattttagt aacctggttc       180
atacgttaaa caaaggataa tgtgaacagc agagaggatt tgttggcaga aaatctatgt       240
tcaatctnga actatctana tcacagacat ttctattcct tt                         282
```

<210> SEQ ID NO 117
<211> LENGTH: 305
<212> TYPE: DNA
<213> ORGANISM: Homo sapien
<220> FEATURE:
<221> NAME/KEY: misc_feature
<222> LOCATION: (1)...(305)
<223> OTHER INFORMATION: n = A,T,C or G

<400> SEQUENCE: 117

```
acacatgtcg cttcactgcc ttcttagatg cttctggtca acatanagga acagggacca        60
tatttatcct ccctcctgaa acaattgcaa ataanacaa aatatatgaa acaattgcaa       120
aataaggcaa atatatgaa acaacaggtc tcgagatatt ggaaatcagt caatgaagga       180
tactgatccc tgatcactgt cctaatgcag gatgtgggaa acagatgagg tcacctctgt       240
```
gactgcccca gcttactgcc tgtagagagt ttctangctg cagttcagac agggagaaat    300
tgggt    305

<210> SEQ ID NO 118
<211> LENGTH: 71
<212> TYPE: DNA
<213> ORGANISM: Homo sapien
<220> FEATURE:
<221> NAME/KEY: misc_feature
<222> LOCATION: (1)...(71)
<223> OTHER INFORMATION: n = A,T,C or G

<400> SEQUENCE: 118
accaaggtgt ntgaatctct gacgtgggga tctctgattc ccgcacaatc tgagtggaaa    60
aantcctggg t    71

<210> SEQ ID NO 119
<211> LENGTH: 212
<212> TYPE: DNA
<213> ORGANISM: Homo sapien
<220> FEATURE:
<221> NAME/KEY: misc_feature
<222> LOCATION: (1)...(212)
<223> OTHER INFORMATION: n = A,T,C or G

<400> SEQUENCE: 119
actccggttg gtgtcagcag cacgtggcat tgaacatngc aatgtggagc ccaaaccaca    60
gaaaatgggg tgaaattggc caactttcta tnaacttatg ttggcaantt tgccaccaac    120
agtaagctgg cccttctaat aaaagaaaat tgaaaggttt ctcactaanc ggaattaant    180
aatggantca aganactccc aggcctcagc gt    212

<210> SEQ ID NO 120
<211> LENGTH: 90
<212> TYPE: DNA
<213> ORGANISM: Homo sapien
<220> FEATURE:
<221> NAME/KEY: misc_feature
<222> LOCATION: (1)...(90)
<223> OTHER INFORMATION: n = A,T,C or G

<400> SEQUENCE: 120
actcgttgca natcaggggc cccccagagt caccgttgca ggagtccttc tggtcttgcc    60
ctccgccggc gcagaacatg ctggggtggt    90

<210> SEQ ID NO 121
<211> LENGTH: 218
<212> TYPE: DNA
<213> ORGANISM: Homo sapien
<220> FEATURE:
<221> NAME/KEY: misc_feature
<222> LOCATION: (1)...(218)
<223> OTHER INFORMATION: n = A,T,C or G

<400> SEQUENCE: 121
tgtancgtga anacgacaga nagggttgtc aaaaatggag aanccttgaa gtcattttga    60
gaataagatt tgctaaaaga tttggggcta aacatggtt attgggagac atttctgaag    120
atatncangt aaaattangga atgaattcat ggttcttttg ggaattcctt tacgatngcc    180
agcatanact tcatgtgggg atancagcta cccttgta    218

<210> SEQ ID NO 122
<211> LENGTH: 171
<212> TYPE: DNA
<213> ORGANISM: Homo sapien

<400> SEQUENCE: 122 tagggtgta tgcaactgta aggacaaaaa ttgagactca actggcttaa ccaataaagg    60
catttgttag ctcatggaac aggaagtcgg atggtgggc atcttcagtg ctgcatgagt    120
caccaccccg gcgggtcat ctgtgccaca ggtccctgtt gacagtgcgg t              171

<210> SEQ ID NO 123
<211> LENGTH: 76
<212> TYPE: DNA
<213> ORGANISM: Homo sapien
<220> FEATURE:
<221> NAME/KEY: misc_feature
<222> LOCATION: (1)...(76)
<223> OTHER INFORMATION: n = A,T,C or G

<400> SEQUENCE: 123
tgtagcgtga agacnacaga atggtgtgtg ctgtgctatc caggaacaca tttattatca    60
ttatcaanta ttgtgt                                                    76

<210> SEQ ID NO 124
<211> LENGTH: 131
<212> TYPE: DNA
<213> ORGANISM: Homo sapien

<400> SEQUENCE: 124 accttttcccc aaggccaatg tcctgtgtgc taactggccg gctgcaggac agctgcaatt   60
caatgtgctg ggtcatatgg agggaggag actctaaaat agccaatttt attctcttgg    120
ttaagatttg t                                                         131

<210> SEQ ID NO 125
<211> LENGTH: 432
<212> TYPE: DNA
<213> ORGANISM: Homo sapien

<400> SEQUENCE: 125
actttatcta ctggctatga aatagatggt ggaaaattgc gttaccaact ataccactgg    60
cttgaaaaag aggtgatagc tcttcagagg acttgtgact tttgctcaga tgctgaagaa   120
ctacagtctg catttggcag aaatgaagat gaatttggat taaatgagga tgctgaagat   180
ttgcctcacc aaacaaaagt gaaacaactg agagaaaatt tcaggaaaaa agacagtgg    240 ctcttgaagt atcagtcact tttgagaatg tttcttagtt actgcatact tcatggatcc   300
catggtgggg gtcttgcatc tgtaagaatg gaattgattt tgcttttgca agaatctcag   360
caggaaacat cagaaccact attttctagc cctctgtcag agcaaacctc agtgcctctc   420 ctcttttgctt gt                                                       432

<210> SEQ ID NO 126
<211> LENGTH: 112
<212> TYPE: DNA
<213> ORGANISM: Homo sapien

<400> SEQUENCE: 126
acacaacttg aatagtaaaa tagaaactga gctgaaattt ctaattcact ttctaaccat    60
agtaagaatg atatttcccc ccagggatca ccaaatattt ataaaaattt gt            112

<210> SEQ ID NO 127
<211> LENGTH: 54
<212> TYPE: DNA
<213> ORGANISM: Homo sapien

<400> SEQUENCE: 127

| accacgaaac cacaaacaag atggaagcat caatccactt gccaagcaca gcag | 54 |

<210> SEQ ID NO 128
<211> LENGTH: 323
<212> TYPE: DNA
<213> ORGANISM: Homo sapien

<400> SEQUENCE: 128

| acctcattag taattgtttt gttgtttcat ttttttctaa tgtctcccct ctaccagctc | 60 |
| acctgagata acagaatgaa aatggaagga cagccagatt tctcctttgc tctctgctca | 120 |
| ttctctctga agtctaggtt acccattttg gggacccatt ataggcaata aacacagttc | 180 |
| ccaaagcatt tggacagttt cttgttgtgt tttagaatgg ttttccttt tcttagcctt | 240 |
| ttcctgcaaa aggctcactc agtcccttgc ttgctcagtg gactgggctc cccagggcct | 300 |
| aggctgcctt cttttccatg tcc | 323 |

<210> SEQ ID NO 129
<211> LENGTH: 192
<212> TYPE: DNA
<213> ORGANISM: Homo sapien
<220> FEATURE:
<221> NAME/KEY: misc_feature
<222> LOCATION: (1)...(192)
<223> OTHER INFORMATION: n = A,T,C or G

<400> SEQUENCE: 129

| acatacatgt gtgtatattt ttaaatatca cttttgtatc actctgactt tttagcatac | 60 |
| tgaaaacaca ctaacataat ttntgtgaac catgatcaga tacaacccaa atcattcatc | 120 |
| tagcacattc atctgtgata naaagatagg tgagtttcat ttccttcacg ttggccaatg | 180 |
| gataaacaaa gt | 192 |

<210> SEQ ID NO 130
<211> LENGTH: 362
<212> TYPE: DNA
<213> ORGANISM: Homo sapien
<220> FEATURE:
<221> NAME/KEY: misc_feature
<222> LOCATION: (1)...(362)
<223> OTHER INFORMATION: n = A,T,C or G

<400> SEQUENCE: 130

| cccttttta tggaatgagt agactgtatg tttgaanatt tanccacaac ctctttgaca | 60 |
| tataatgacg caacaaaaag gtgctgttta gtcctatggt tcagtttatg cccctgacaa | 120 |
| gtttccattg tgttttgccg atcttctggc taatcgtggt atcctccatg ttattagtaa | 180 |
| ttctgtattc catttttgtta acgcctggta gatgtaacct gctangaggc taactttata | 240 |
| cttatttaaa agctcttatt ttgtggtcat taaaatggca atttatgtgc agcactttat | 300 |
| tgcagcagga agcacgtgtg ggttggttgt aaagctcttt gctaatctta aaaagtaatg | 360 |
| gg | 362 |

<210> SEQ ID NO 131
<211> LENGTH: 332
<212> TYPE: DNA
<213> ORGANISM: Homo sapien
<220> FEATURE:
<221> NAME/KEY: misc_feature
<222> LOCATION: (1)...(332)
<223> OTHER INFORMATION: n = A,T,C or G

<400> SEQUENCE: 131

```
cttttttgaaa gatcgtgtcc actcctgtgg acatcttgtt ttaatggagt ttcccatgca      60
gtangactgg tatggttgca gctgtccaga taaaaacatt tgaagagctc caaaatgaga     120
gttctcccag gttcgccctg ctgctccaag tctcagcagc agcctctttt aggaggcatc     180
ttctgaacta gattaaggca gcttgtaaat ctgatgtgat ttggtttatt atccaactaa     240
cttccatctg ttatcactgg agaaagccca gactccccan gacnggtacg gattgtgggc     300
atanaaggat tgggtgaagc tggcgttgtg gt                                   332
```

<210> SEQ ID NO 132
<211> LENGTH: 322
<212> TYPE: DNA
<213> ORGANISM: Homo sapien
<220> FEATURE:
<221> NAME/KEY: misc_feature
<222> LOCATION: (1)...(322)
<223> OTHER INFORMATION: n = A,T,C or G

<400> SEQUENCE: 132

```
acttttgcca ttttgtatat ataaacaatc ttgggacatt ctcctgaaaa ctaggtgtcc      60
agtggctaag agaactcgat ttcaagcaat tctgaaagga aaaccagcat gacacagaat     120
ctcaaattcc caaacagggg ctctgtggga aaaatgaggg aggacctttg tatctcgggt     180
tttagcaagt taaatgaan atgacaggaa aggcttattt atcaacaaag agaagagttg     240
ggatgcttct aaaaaaaact ttggtagaga aaataggaat gctnaatcct agggaagcct     300
gtaacaatct acaattggtc ca                                              322
```

<210> SEQ ID NO 133
<211> LENGTH: 278
<212> TYPE: DNA
<213> ORGANISM: Homo sapien
<220> FEATURE:
<221> NAME/KEY: misc_feature
<222> LOCATION: (1)...(278)
<223> OTHER INFORMATION: n = A,T,C or G

<400> SEQUENCE: 133

```
acaagccttc acaagtttaa ctaaattggg attaatcttt ctgtanttat ctgcataatt      60
cttgtttttc tttccatctg gctcctgggt tgacaatttg tggaaacaac tctattgcta     120
ctatttaaaa aaaatcacaa atctttccct ttaagctatg ttnaattcaa actattcctg     180
ctattcctgt tttgtcaaag aaattatatt tttcaaaata tgtntatttg tttgatgggt     240
cccacgaaac actaataaaa accacagaga ccagcctg                             278
```

<210> SEQ ID NO 134
<211> LENGTH: 121
<212> TYPE: DNA
<213> ORGANISM: Homo sapien
<220> FEATURE:
<221> NAME/KEY: misc_feature
<222> LOCATION: (1)...(121)
<223> OTHER INFORMATION: n = A,T,C or G

```
<400> SEQUENCE: 134
gtttanaaaa cttgtttagc tccatagagg aaagaatgtt aaactttgta ttttaaaaca        60
tgattctctg aggttaaact tggttttcaa atgttatttt tacttgtatt ttgcttttgg       120
t                                                                      121

<210> SEQ ID NO 135
<211> LENGTH: 350
<212> TYPE: DNA
<213> ORGANISM: Homo sapien
<220> FEATURE:
<221> NAME/KEY: misc_feature
<222> LOCATION: (1)...(350)
<223> OTHER INFORMATION: n = A,T,C or G

<400> SEQUENCE: 135
acttanaacc atgcctagca catcagaatc cctcaaagaa catcagtata atcctatacc        60
atancaagtg gtgactggtt aagcgtgcga caaaggtcag ctggcacatt acttgtgtgc       120
aaacttgata cttttgttct aagtaggaac tagtatacag tncctaggan tggtactcca       180
gggtgccccc caactcctgc agccgctcct ctgtgccagn ccctgnaagg aactttcgct       240
ccacctcaat caagccctgg gccatgctac ctgcaattgg ctgaacaaac gtttgctgag       300
ttcccaagga tgcaaagcct ggtgctcaac tcctggggcg tcaactcagt                 350

<210> SEQ ID NO 136
<211> LENGTH: 399
<212> TYPE: DNA
<213> ORGANISM: Homo sapien
<220> FEATURE:
<221> NAME/KEY: misc_feature
<222> LOCATION: (1)...(399)
<223> OTHER INFORMATION: n = A,T,C or G

<400> SEQUENCE: 136
tgtaccgtga agacgacaga agttgcatgg cagggacagg gcagggccga ggccagggtt        60
gctgtgattg tatccgaata ntcctcgtga gaaaagataa tgagatgacg tgagcagcct       120
gcagacttgt gtctgccttc aanaagccag acaggaaggc cctgcctgcc ttggctctga       180
cctggcggcc agccagccag ccacaggtgg gcttcttcct tttgtggtga caacnccaag       240
aaaactgcag aggcccaggg tcaggtgtna gtgggtangt gaccataaaa caccaggtgc       300
tcccaggaac ccgggcaaag gccatcccca cctacagcca gcatgcccac tggcgtgatg       360
ggtgcagang gatgaagcag ccagntgttc tgctgtggt                             399

<210> SEQ ID NO 137
<211> LENGTH: 165
<212> TYPE: DNA
<213> ORGANISM: Homo sapien
<220> FEATURE:
<221> NAME/KEY: misc_feature
<222> LOCATION: (1)...(165)
<223> OTHER INFORMATION: n = A,T,C or G

<400> SEQUENCE: 137
actggtgtgg tnggggtga tgctggtggt anaagttgan gtgacttcan gatggtgtgt         60
ggaggaagtg tgtgaacgta gggatgtaga ngttttggcc gtgctaaatg agcttcggga       120
ttggctggtc ccactggtgg tcactgtcat tggtggggtt cctgt                      165
```

```
<210> SEQ ID NO 138
<211> LENGTH: 338
<212> TYPE: DNA
<213> ORGANISM: Homo sapien
<220> FEATURE:
<221> NAME/KEY: misc_feature
<222> LOCATION: (1)...(338)
<223> OTHER INFORMATION: n = A,T,C or G

<400> SEQUENCE: 138
actcactgga atgccacatt cacaacagaa tcagaggtct gtgaaaacat taatggctcc      60
ttaacttctc cagtaagaat cagggacttg aaatggaaac gttaacagcc acatgcccaa     120
tgctgggcag tctcccatgc cttccacagt gaaagggctt gagaaaaatc acatccaatg    180
tcatgtgttt ccagccacac caaaaggtgc ttggggtgga gggctggggg catananggt    240
cangcctcag gaagcctcaa gttccattca gctttgccac tgtacattcc ccatntttaa    300
aaaaactgat gccttttttt ttttttttg taaaattc                              338

<210> SEQ ID NO 139
<211> LENGTH: 382
<212> TYPE: DNA
<213> ORGANISM: Homo sapien

<400> SEQUENCE: 139
gggaatcttg gttttggca tctggtttgc ctatagccga ggccactttg acagaacaaa       60
gaaagggact tcgagtaaga aggtgattta cagccagcct agtgcccgaa gtgaaggaga    120
attcaaacag acctcgtcat tcctggtgtg agcctggtcg gctcaccgcc tatcatctgc    180
atttgcctta ctcaggtgct accggactct ggccctgat gtctgtagtt tcacaggatg    240
ccttatttgt cttctacacc ccacagggcc cctacttct tcggatgtgt ttttaataat     300
gtcagctatg tgccccatcc tccttcatgc cctccctccc tttcctacca ctgctgagtg    360
gcctggaact tgtttaaagt gt                                              382

<210> SEQ ID NO 140
<211> LENGTH: 200
<212> TYPE: DNA
<213> ORGANISM: Homo sapien
<220> FEATURE:
<221> NAME/KEY: misc_feature
<222> LOCATION: (1)...(200)
<223> OTHER INFORMATION: n = A,T,C or G

<400> SEQUENCE: 140 accaaancttt ctttctgttg tgttngattt tactataggg gtttngcttn ttctaaanat    60
acttttcatt taacancttt tgttaagtgt caggctgcac tttgctccat anaattattg    120
ttttcacatt tcaacttgta tgtgtttgtc tcttanagca ttggtgaaat cacatatttt    180
atattcagca taaaggagaa                                                 200

<210> SEQ ID NO 141
<211> LENGTH: 335
<212> TYPE: DNA
<213> ORGANISM: Homo sapien
<220> FEATURE:
<221> NAME/KEY: misc_feature
<222> LOCATION: (1)...(335)
<223> OTHER INFORMATION: n = A,T,C or G
```

<400> SEQUENCE: 141

```
actttatttt caaaacactc atatgttgca aaaaacacat agaaaaataa agtttggtgg      60
gggtgctgac taaacttcaa gtcacagact tttatgtgac agattggagc agggtttgtt    120
atgcatgtag agaacccaaa ctaatttatt aaacaggata gaaacaggct gtctgggtga    180
aatggttctg agaaccatcc aattcacctg tcagatgctg atanactagc tcttcagatg    240
tttttctacc agttcagaga tnggttaatg actanttcca atggggaaaa agcaagatgg    300
attcacaaac caagtaattt aaacaaaga cactt                                335
```

<210> SEQ ID NO 142
<211> LENGTH: 459
<212> TYPE: DNA
<213> ORGANISM: Homo sapien
<220> FEATURE:
<221> NAME/KEY: misc_feature
<222> LOCATION: (1)...(459)
<223> OTHER INFORMATION: n = A,T,C or G

<400> SEQUENCE: 142

```
accaggttaa tattgccaca tatatccttt ccaattgcgg gctaaacaga cgtgtattta      60
gggttgttta aagacaaccc agcttaatat caagagaaat tgtgaccttt catggagtat    120
ctgatggaga aaacactgag ttttgacaaa tcttatttta ttcagatagc agtctgatca    180
cacatggtcc aacaacactc aaataataaa tcaaatatna tcagatgtta aagattggtc    240
ttcaaacatc atagccaatg atgccccgct tgcctataat ctctccgaca taaaaccaca    300
tcaacacctc agtggccacc aaaccattca gcacagcttc cttaactgtg agctgtttga    360
agctaccagt ctgagcacta ttgactatnt ttttcangct ctgaatagct ctagggatct    420
cagcangggt gggaggaacc agctcaacct tggcgtant                           459
```

<210> SEQ ID NO 143
<211> LENGTH: 140
<212> TYPE: DNA
<213> ORGANISM: Homo sapien

<400> SEQUENCE: 143

```
acatttcctt ccaccaagtc aggactcctg gcttctgtgg gagttcttat cacctgaggg      60
aaatccaaac agtctctcct agaaaggaat agtgtcacca accccaccca tctccctgag    120
accatccgac ttccctgtgt                                                140
```

<210> SEQ ID NO 144
<211> LENGTH: 164
<212> TYPE: DNA
<213> ORGANISM: Homo sapien
<220> FEATURE:
<221> NAME/KEY: misc_feature
<222> LOCATION: (1)...(164)
<223> OTHER INFORMATION: n = A,T,C or G

<400> SEQUENCE: 144

```
acttcagtaa caacatacaa taacaacatt aagtgtatat tgccatcttt gtcattttct      60
atctatacca ctctcccttc tgaaaacaan aatcactanc caatcactta tacaaatttg    120
aggcaattaa tccatatttg ttttcaataa ggaaaaaaag atgt                      164
```

<210> SEQ ID NO 145
<211> LENGTH: 303
<212> TYPE: DNA
<213> ORGANISM: Homo sapien

```
<220> FEATURE:
<221> NAME/KEY: misc_feature
<222> LOCATION: (1)...(303)
<223> OTHER INFORMATION: n = A,T,C or G

<400> SEQUENCE: 145
acgtagacca tccaactttg tatttgtaat ggcaaacatc cagnagcaat tcctaaacaa      60
actggagggt atttataccc aattatccca ttcattaaca tgccctcctc ctcaggctat     120
gcaggacagc tatcataagt cggcccaggc atccagatac taccatttgt ataaacttca     180
gtaggggagt ccatccaagt gacaggtcta atcaaaggag gaaatggaac ataagcccag     240
tagtaaaatn ttgcttagct gaaacagcca caaaagactt accgccgtgg tgattaccat     300
caa                                                                   303

<210> SEQ ID NO 146
<211> LENGTH: 327
<212> TYPE: DNA
<213> ORGANISM: Homo sapien
<220> FEATURE:
<221> NAME/KEY: misc_feature
<222> LOCATION: (1)...(327)
<223> OTHER INFORMATION: n = A,T,C or G

<400> SEQUENCE: 146
actgcagctc aattagaagt ggtctctgac tttcatcanc ttctccctgg gctccatgac      60
actggcctgg agtgactcat tgctctggtt ggttgagaga gctcctttgc caacaggcct    120
ccaagtcagg gctgggattt gtttcctttc cacattctag caacaatatg ctggccactt    180
cctgaacagg gagggtggga ggagccagca tggaacaagc tgccactttc taaagtagcc    240
agacttgccc ctgggcctgt cacacctact gatgacccttc tgtgcctgca ggatggaatg    300 tagggggtgag ctgtgtgact ctatggt                                       327

<210> SEQ ID NO 147
<211> LENGTH: 173
<212> TYPE: DNA
<213> ORGANISM: Homo sapien
<220> FEATURE:
<221> NAME/KEY: misc_feature
<222> LOCATION: (1)...(173)
<223> OTHER INFORMATION: n = A,T,C or G

<400> SEQUENCE: 147
acattgtttt tttgagataa agcattgana gagctctcct taacgtgaca caatggaagg      60
actggaacac atacccacat ctttgttctg agggataatt ttctgataaa gtcttgctgt    120
atattcaagc acatatgtta tatattattc agttccatgt ttatagccta gtt           173

<210> SEQ ID NO 148
<211> LENGTH: 477
<212> TYPE: DNA
<213> ORGANISM: Homo sapien
<220> FEATURE:
<221> NAME/KEY: misc_feature
<222> LOCATION: (1)...(477)
<223> OTHER INFORMATION: n = A,T,C or G

<400> SEQUENCE: 148
acaaccactt tatctcatcg aattttttaac ccaaactcac tcactgtgcc tttctatcct     60
atgggatata ttatttgatg ctccatttca tcacacatat atgaataata cactcatact    120
gccctactac ctgctgcaat aatcacattc ccttcctgtc ctgaccctga agccattggg    180
```

```
gtggtcctag tggccatcag tccangcctg caccttgagc ccttgagctc cattgctcac      240 nccanccac ctcaccgacc ccatcctctt acacagctac ctccttgctc tctaaccca        300 tagattatnt ccaaattcag tcaattaagt tactattaac actctacccg acatgtccag      360
caccactggt aagccttctc cagccaacac acacacacac acacncacac acacacatat      420
ccaggcacag gctacctcat cttcacaatc acccctttaa ttaccatgct atggtgg         477
```

<210> SEQ ID NO 149
<211> LENGTH: 207
<212> TYPE: DNA
<213> ORGANISM: Homo sapien

<400> SEQUENCE: 149

```
acagttgtat tataatatca agaaataaac ttgcaatgag agcatttaag agggaagaac       60
taacgtattt tagagagcca aggaaggttt ctgtggggag tgggatgtaa ggtggggcct      120
gatgataaat aagagtcagc caggtaagtg ggtggtgtgg tatgggcaca gtgaagaaca      180
tttcaggcag agggaacagc agtgaaa                                         207
```

<210> SEQ ID NO 150
<211> LENGTH: 111
<212> TYPE: DNA
<213> ORGANISM: Homo sapien
<220> FEATURE:
<221> NAME/KEY: misc_feature
<222> LOCATION: (1)...(111)
<223> OTHER INFORMATION: n = A,T,C or G

<400> SEQUENCE: 150

```
accttgattt cattgctgct ctgatggaaa cccaactatc taatttagct aaaacatggg       60
cacttaaatg tggtcagtgt ttggacttgt taactantgg catctttggg t              111
```

<210> SEQ ID NO 151
<211> LENGTH: 196
<212> TYPE: DNA
<213> ORGANISM: Homo sapien

<400> SEQUENCE: 151

```
agcgcggcag gtcatattga acattccaga tacctatcat tactcgatgc tgttgataac       60
agcaagatgg ctttgaactc agggtcacca ccagctattg gaccttacta tgaaaaccat      120
ggataccaac cggaaaaccc ctatcccgca cagcccactg tggtccccac tgtctacgag      180
gtgcatccgg ctcagt                                                     196
```

<210> SEQ ID NO 152
<211> LENGTH: 132
<212> TYPE: DNA
<213> ORGANISM: Homo sapien

<400> SEQUENCE: 152

```
acagcacttt cacatgtaag aagggagaaa ttcctaaatg taggagaaag ataacagaac       60
cttccccttt tcatctagtg gtggaaacct gatgctttat gttgacagga atagaaccag      120
gagggagttt gt                                                         132
```

<210> SEQ ID NO 153
<211> LENGTH: 285
<212> TYPE: DNA
<213> ORGANISM: Homo sapien

```
<220> FEATURE:
<221> NAME/KEY: misc_feature
<222> LOCATION: (1)...(285)
<223> OTHER INFORMATION: n = A,T,C or G

<400> SEQUENCE: 153
acaanaccca nganaggcca ctggccgtgg tgtcatggcc tccaaacatg aaagtgtcag      60
cttctgctct tatgtcctca tctgacaact ctttaccatt tttatcctcg ctcagcagga     120
gcacatcaat aaagtccaaa gtcttggact tggccttggc ttggaggaag tcatcaacac     180
cctggctagt gagggtgcgg cgccgctcct ggatgacggc atctgtgaag tcgtgcacca     240
gtctgcaggc cctgtggaag cgccgtccac acggagtnag gaatt                     285

<210> SEQ ID NO 154
<211> LENGTH: 333
<212> TYPE: DNA
<213> ORGANISM: Homo sapien

<400> SEQUENCE: 154
accacagtcc tgttgggcca gggcttcatg acccttctg tgaaaagcca tattatcacc       60
accccaaatt tttccttaaa tatctttaac tgaagggtc agcctcttga ctgcaaagac      120
cctaagccgg ttacacagct aactcccact ggccctgatt tgtgaaattg ctgctgcctg     180
attggcacag gagtcgaagg tgttcagctc ccctcctccg tggaacgaga ctctgatttg     240
agtttcacaa attctcgggc cacctcgtca ttgctcctct gaaataaaat ccggagaatg     300
gtcaggcctg tctcatccat atggatcttc cgg                                 333

<210> SEQ ID NO 155
<211> LENGTH: 308
<212> TYPE: DNA
<213> ORGANISM: Homo sapien
<220> FEATURE:
<221> NAME/KEY: misc_feature
<222> LOCATION: (1)...(308)
<223> OTHER INFORMATION: n = A,T,C or G

<400> SEQUENCE: 155
actggaaata ataaaaccca catcacagtg ttgtgtcaaa gatcatcagg gcatggatgg       60
gaaagtgctt tgggaactgt aaagtgccta acacatgatc gatgattttt gttataatat     120
ttgaatcacg gtgcatacaa actctcctgc ctgctcctcc tgggcccag ccccagcccc      180 atcacagctc actgctctgt tcatccaggc ccagcatgta gtggctgatt cttcttggct     240
gcttttagcc tccanaagtt tctctgaagc caaccaaacc tctangtgta aggcatgctg     300
gccctggt                                                             308

<210> SEQ ID NO 156
<211> LENGTH: 295
<212> TYPE: DNA
<213> ORGANISM: Homo sapien

<400> SEQUENCE: 156
accttgctcg gtgcttggaa catattagga actcaaaata tgagatgata acagtgccta      60
ttattgatta ctgagagaac tgttagacat ttagttgaag attttctaca caggaactga    120
gaataggaga ttatgtttgg ccctcatatt ctctcctatc ctccttgcct cattctatgt    180
ctaatatatt ctcaatcaaa taaggttagc ataatcagga atcgaccaa ataccaatat     240 aaaaccagat gtctatcctt aagattttca aatagaaaac aaattaacag actat          295
```

<210> SEQ ID NO 157
<211> LENGTH: 126
<212> TYPE: DNA
<213> ORGANISM: Homo sapien

<400> SEQUENCE: 157

| | | | | | |
|---|---|---|---|---|---|
| acaagtttaa | atagtgctgt | cactgtgcat | gtgctgaaat | gtgaaatcca | ccacatttct | 60 |
| gaagagcaaa | acaaattctg | tcatgtaatc | tctatcttgg | gtcgtgggta | tatctgtccc | 120 |
| cttagt | | | | | | 126 |

<210> SEQ ID NO 158
<211> LENGTH: 442
<212> TYPE: DNA
<213> ORGANISM: Homo sapien
<220> FEATURE:
<221> NAME/KEY: misc_feature
<222> LOCATION: (1)...(442)
<223> OTHER INFORMATION: n = A,T,C or G

<400> SEQUENCE: 158

| | | | | | |
|---|---|---|---|---|---|
| acccactggt | cttggaaaca | cccatcctta | atacgatgat | ttttctgtcg | tgtgaaaatg | 60 |
| aanccagcag | gctgccccta | gtcagtcctt | ccttccagag | aaaaagagat | ttgagaaagt | 120 |
| gcctgggtaa | ttcaccatta | atttcctccc | ccaaactctc | tgagtcttcc | cttaatattt | 180 |
| ctggtggttc | tgaccaaagc | aggtcatggt | ttgttgagca | tttgggatcc | cagtgaagta | 240 |
| natgtttgta | gccttgcata | cttagccctt | cccacgcaca | aacggagtgg | cagagtggtg | 300 |
| ccaaccctgt | tttcccagtc | cacgtagaca | gattcacagt | gcggaattct | ggaagctgga | 360 |
| nacagacggg | ctctttgcag | agccgggact | ctgaganggag | catgagggcc | tctgcctctg | 420 |
| tgttcattct | ctgatgtcct | gt | | | | 442 |

<210> SEQ ID NO 159
<211> LENGTH: 498
<212> TYPE: DNA
<213> ORGANISM: Homo sapien
<220> FEATURE:
<221> NAME/KEY: misc_feature
<222> LOCATION: (1)...(498)
<223> OTHER INFORMATION: n = A,T,C or G

<400> SEQUENCE: 159

| | | | | | |
|---|---|---|---|---|---|
| acttccaggt | aacgttgttg | tttccgttga | gcctgaactg | atgggtgacg | ttgtaggttc | 60 |
| tccaacaaga | actgaggttg | cagagcgggt | agggaagagt | gctgttccag | ttgcacctgg | 120 |
| gctgctgtgg | actgttgttg | attcctcact | acggcccaag | gttgtggaac | tggcanaaag | 180 |
| gtgtgttgtt | gganttgagc | tcgggcggct | gtggtaggtt | gtgggctctt | caacaggggc | 240 |
| tgctgtggtg | ccgggangtg | aangtgttgt | gtcacttgag | cttggccagc | tctgaaaagt | 300 |
| antanattct | tcctgaaggc | cagcgcttgt | ggagctggca | ngggtcantg | ttgtgtgtaa | 360 |
| cgaaccagtg | ctgctgtggg | tgggtgtana | tcctccacaa | agcctgaagt | tatggtgtcn | 420 |
| tcaggtaana | atgtggtttc | agtgtccctg | ggcngctgtg | gaaggttgta | nattgtcacc | 480 |
| aagggaataa | gctgtggt | | | | | 498 |

<210> SEQ ID NO 160
<211> LENGTH: 380
<212> TYPE: DNA
<213> ORGANISM: Homo sapien

```
<220> FEATURE:
<221> NAME/KEY: misc_feature
<222> LOCATION: (1)...(380)
<223> OTHER INFORMATION: n = A,T,C or G

<400> SEQUENCE: 160
acctgcatcc agcttccctg ccaaactcac aaggagacat caacctctag acagggaaac    60
agcttcagga tacttccagg agacagagcc accagcagca aaacaaatat tcccatgcct   120
ggagcatggc atagaggaag ctganaaatg tggggtctga ggaagccatt tgagtctggc   180
cactagacat ctcatcagcc acttgtgtga agagatgccc catgacccca gatgcctctc   240
ccacccttac ctccatctca cacacttgag ctttccactc tgtataattc taacatcctg   300
gagaaaaatg gcagtttgac cgaacctgtt cacaacggta gaggctgatt tctaacgaaa   360
cttgtagaat gaagcctgga                                              380

<210> SEQ ID NO 161
<211> LENGTH: 114
<212> TYPE: DNA
<213> ORGANISM: Homo sapien

<400> SEQUENCE: 161
actccacatc ccctctgagc aggcggttgt cgttcaaggt gtatttggcc ttgcctgtca    60
cactgtccac tggccccta tccacttggt gcttaatccc tcgaaagagc atgt          114

<210> SEQ ID NO 162
<211> LENGTH: 177
<212> TYPE: DNA
<213> ORGANISM: Homo sapien

<400> SEQUENCE: 162
actttctgaa tcgaatcaaa tgatacttag tgtagttta atatcctcat atatatcaaa    60
gttttactac tctgataatt ttgtaaacca ggtaaccaga acatccagtc atacagcttt   120
tggtgatata taacttggca ataacccagt ctggtgatac ataaaactac tcactgt      177

<210> SEQ ID NO 163
<211> LENGTH: 137
<212> TYPE: DNA
<213> ORGANISM: Homo sapien
<220> FEATURE:
<221> NAME/KEY: misc_feature
<222> LOCATION: (1)...(137)
<223> OTHER INFORMATION: n = A,T,C or G

<400> SEQUENCE: 163
catttataca gacaggcgtg aagacattca cgacaaaaac gcgaaattct atcccgtgac    60
canagaaggc agctacggct actcctacat cctggcgtgg gtggccttcg cctgcacctt   120
catcagcggc atgatgt                                                  137

<210> SEQ ID NO 164
<211> LENGTH: 469
<212> TYPE: DNA
<213> ORGANISM: Homo sapien
<220> FEATURE:
<221> NAME/KEY: misc_feature
<222> LOCATION: (1)...(469)
<223> OTHER INFORMATION: n = A,T,C or G
```

<400> SEQUENCE: 164

| cttatcacaa tgaatgttct cctgggcagc gttgtgatct ttgccacctt cgtgacttta | 60 |
| tgcaatgcat catgctattt catacctaat gagggagttc caggagattc aaccaggaaa | 120 |
| tgcatggatc tcaaaggaaa caaacaccca ataaactcgg agtggcagac tgacaactgt | 180 |
| gagacatgca cttgctacga aacagaaatt tcatgttgca cccttgtttc tacacctgtg | 240 |
| ggttatgaca aagacaactg ccaaagaatc ttcaagaagg aggactgcaa gtatatcgtg | 300 |
| gtggagaaga aggacccaaa aaagacctgt tctgtcagtg aatggataat ctaatgtgct | 360 |
| tctagtaggc acagggctcc caggccaggc ctcattctcc tctggcctct aatagtcaat | 420 |
| gattgtgtag ccatgcctat cagtaaaaag atntttgagc aaacacttt | 469 |

<210> SEQ ID NO 165
<211> LENGTH: 195
<212> TYPE: DNA
<213> ORGANISM: Homo sapien
<220> FEATURE:
<221> NAME/KEY: misc_feature
<222> LOCATION: (1)...(195)
<223> OTHER INFORMATION: n = A,T,C or G

<400> SEQUENCE: 165

| acagtttttt atanatatcg acattgccgg cacttgtgtt cagtttcata aagctggtgg | 60 |
| atccgctgtc atccactatt ccttggctag agtaaaaatt attcttatag cccatgtccc | 120 |
| tgcaggccgc ccgcccgtag ttctcgttcc agtcgtcttg gcacacaggg tgccaggact | 180 |
| tcctctgaga tgagt | 195 |

<210> SEQ ID NO 166
<211> LENGTH: 383
<212> TYPE: DNA
<213> ORGANISM: Homo sapien
<220> FEATURE:
<221> NAME/KEY: misc_feature
<222> LOCATION: (1)...(383)
<223> OTHER INFORMATION: n = A,T,C or G

<400> SEQUENCE: 166

| acatcttagt agtgtggcac atcaggggc catcagggtc acagtcactc atagcctcgc | 60 |
| cgaggtcgga gtccacacca ccggtgtagg tgtgctcaat cttgggcttg gcgcccacct | 120 |
| ttggagaagg gatatgctgc acacacatgt ccacaaagcc tgtgaactcg ccaaagaatt | 180 |
| tttgcagacc agcctgagca aggggcggat gttcagcttc agctcctcct tcgtcaggtg | 240 |
| gatgccaacc tcgtctangg tccgtgggaa gctggtgtcc acntcaccta caacctgggc | 300 |
| gangatctta taaagaggct ccnagataaa ctccacgaaa cttctctggg agctgctagt | 360 |
| nggggccttt ttggtgaact ttc | 383 |

<210> SEQ ID NO 167
<211> LENGTH: 247
<212> TYPE: DNA
<213> ORGANISM: Homo sapien
<220> FEATURE:
<221> NAME/KEY: misc_feature
<222> LOCATION: (1)...(247)
<223> OTHER INFORMATION: n = A,T,C or G

<400> SEQUENCE: 167

| acagagccag accttggcca taaatgaanc agagattaag actaaacccc aagtcganat | 60 |
| tggagcagaa actggagcaa gaagtgggcc tggggctgaa gtagagacca aggccactgc | 120 |

| tatanccata cacagagcca actctcaggc caaggcnatg gttggggcag anccagagac | 180 |
| tcaatctgan tccaaagtgg tggctggaac actggtcatg acanaggcag tgactctgac | 240 |
| tgangtc | 247 |

<210> SEQ ID NO 168
<211> LENGTH: 273
<212> TYPE: DNA
<213> ORGANISM: Homo sapien
<220> FEATURE:
<221> NAME/KEY: misc_feature
<222> LOCATION: (1)...(273)
<223> OTHER INFORMATION: n = A,T,C or G

<400> SEQUENCE: 168

| acttctaagt tttctagaag tggaaggatt gtantcatcc tgaaaatggg tttacttcaa | 60 |
| aatccctcan ccttgttctt cacnactgtc tatactgana gtgtcatgtt tccacaaagg | 120 |
| gctgacacct gagcctgnat tttcactcat ccctgagaag ccctttccag tagggtgggc | 180 |
| aattcccaac ttccttgcca caagcttccc aggctttctc ccctggaaaa ctccagcttg | 240 |
| agtcccagat acactcatgg gctgccctgg gca | 273 |

<210> SEQ ID NO 169
<211> LENGTH: 431
<212> TYPE: DNA
<213> ORGANISM: Homo sapien
<220> FEATURE:
<221> NAME/KEY: misc_feature
<222> LOCATION: (1)...(431)
<223> OTHER INFORMATION: n = A,T,C or G

<400> SEQUENCE: 169

| acagccttgg cttccccaaa ctccacagtc tcagtgcaga aagatcatct tccagcagtc | 60 |
| agctcagacc agggtcaaag gatgtgacat caacagtttc tggtttcaga acaggttcta | 120 |
| ctactgtcaa atgaccccc atacttcctc aaaggctgtg gtaagttttg cacaggtgag | 180 |
| ggcagcagaa aggggtant tactgatgga caccatcttc tctgtatact ccacactgac | 240 |
| cttgccatgg gcaaaggccc ctaccacaaa acaatagga tcactgctgg gcaccagctc | 300 |
| acgcacatca ctgacaaccg ggatggaaaa agaantgcca actttcatac atccaactgg | 360 |
| aaagtgatct gatactggat tcttaattac cttcaaaagc ttctgggggc catcagctgc | 420 |
| tcgaacactg a | 431 |

<210> SEQ ID NO 170
<211> LENGTH: 266
<212> TYPE: DNA
<213> ORGANISM: Homo sapien
<220> FEATURE:
<221> NAME/KEY: misc_feature
<222> LOCATION: (1)...(266)
<223> OTHER INFORMATION: n = A,T,C or G

<400> SEQUENCE: 170

| acctgtgggc tgggctgtta tgcctgtgcc ggctgctgaa agggagttca gaggtggagc | 60 |
| tcaaggagct ctgcaggcat tttgccaanc ctctccanag canagggagc aacctacact | 120 |
| ccccgctaga aagacaccag attggagtcc tgggaggggg agttgggtg ggcatttgat | 180 |
| gtatacttgt cacctgaatg aangagccag agaggaanga gacgaanatg anattggcct | 240 |
| tcaaagctag gggtctggca ggtgga | 266 |

```
<210> SEQ ID NO 171
<211> LENGTH: 1248
<212> TYPE: DNA
<213> ORGANISM: Homo sapien
<220> FEATURE:
<221> NAME/KEY: misc_feature
<222> LOCATION: (1)...(1248)
<223> OTHER INFORMATION: n = A,T,C or G

<400> SEQUENCE: 171
ggcagccaaa tcataaacgg cgaggactgc agcccgcact cgcagccctg caggcggca        60
ctggtcatgg aaaacgaatt gttctgctcg ggcgtcctgg tgcatccgca gtgggtgctg      120
tcagccgcac actgtttcca gaagtgagtg cagagctcct acaccatcgg gctgggcctg      180
cacagtcttg aggccgacca agagccaggg agccagatgg tggaggccag cctctccgta      240
cggcacccag agtacaacag accccttgctc gctaacgacc tcatgctcat caagttggac     300
gaatccgtgt ccgagtctga caccatccgg agcatcagca ttgcttcgca gtgccctacc     360
gcggggaact cttgcctcgt ttctggctgg ggtctgctgg cgaacggcag aatgcctacc     420
gtgctgcagt gcgtgaacgt gtcggtggtg tctgaggagg tctgcagtaa gctctatgac     480
ccgctgtacc accccagcat gttctgcgcc ggcggagggc aagaccagaa ggactcctgc     540
aacggtgact ctgggggggcc cctgatctgc aacgggtact gcagggcct tgtgtctttc     600
ggaaaagccc cgtgtggcca agttggcgtg ccaggtgtct acaccaacct ctgcaaattc     660
actgagtgga tagagaaaac cgtccaggcc agttaactct ggggactggg aacccatgaa     720
attgaccccc aaatacatcc tgcggaagga attcaggaat atctgttccc agcccctcct     780
ccctcaggcc caggagtcca ggcccccagc ccctcctccc tcaaaccaag ggtacagatc     840
cccagccccc cctccctcag acccaggagt ccagaccccc cagcccctcc tccctcagac     900
ccaggagtcc agcccctcct ccctcagacc caggagtcca gaccccccag cccctcctcc     960
ctcagaccca ggggtccagg ccccccaaccc ctcctccctc agactcagag gtccaagccc    1020
ccaacccntc attccccaga cccagaggtc caggtcccag cccctcntcc ctcagaccca    1080
gcggtccaat gccacctaga ctntccctgt acacagtgcc ccttgtggc acgttgaccc    1140
aaccttacca gttggttttt cattttttngt ccctttcccc tagatccaga aataaagttt    1200
aagagaagng caaaaaaaaa aaaaaaaaa aaaaaaaaaa aaaaaaaa                   1248

<210> SEQ ID NO 172
<211> LENGTH: 159
<212> TYPE: PRT
<213> ORGANISM: Homo sapien
<220> FEATURE:
<221> NAME/KEY: VARIANT
<222> LOCATION: (1)...(159)
<223> OTHER INFORMATION: Xaa = Any Amino Acid

<400> SEQUENCE: 172

Met Val Glu Ala Ser Leu Ser Val Arg His Pro Glu Tyr Asn Arg Pro
1               5                   10                  15

Leu Leu Ala Asn Asp Leu Met Leu Ile Lys Leu Asp Glu Ser Val Ser
            20                  25                  30

Glu Ser Asp Thr Ile Arg Ser Ile Ser Ile Ala Ser Gln Cys Pro Thr
        35                  40                  45

Ala Gly Asn Ser Cys Leu Val Ser Gly Trp Gly Leu Leu Ala Asn Gly
    50                  55                  60

Arg Met Pro Thr Val Leu Gln Cys Val Asn Val Ser Val Val Ser Glu
65                  70                  75                  80
```

```
Glu Val Cys Ser Lys Leu Tyr Asp Pro Leu Tyr His Pro Ser Met Phe
                85                  90                  95

Cys Ala Gly Gly Gln Xaa Gln Xaa Asp Ser Cys Asn Gly Asp Ser
            100                 105                 110

Gly Gly Pro Leu Ile Cys Asn Gly Tyr Leu Gln Gly Leu Val Ser Phe
            115                 120                 125

Gly Lys Ala Pro Cys Gly Gln Val Gly Val Pro Gly Val Tyr Thr Asn
        130                 135                 140

Leu Cys Lys Phe Thr Glu Trp Ile Glu Lys Thr Val Gln Ala Ser
145                 150                 155

<210> SEQ ID NO 173
<211> LENGTH: 1265
<212> TYPE: DNA
<213> ORGANISM: Homo sapien
<220> FEATURE:
<221> NAME/KEY: misc_feature
<222> LOCATION: (1)...(1265)
<223> OTHER INFORMATION: n = A,T,C or G

<400> SEQUENCE: 173
ggcagcccgc actcgcagcc ctggcaggcg gcactggtca tggaaaacga attgttctgc      60
tcgggcgtcc tggtgcatcc gcagtgggtg ctgtcagccg cacactgttt ccagaactcc     120
tacaccatcg ggctgggcct gcacagtctt gaggccgacc aagagccagg agccagatg     180 gtggaggcca gcctctccgt acggcaccca gagtacaaca gacccttgct cgctaacgac     240
ctcatgctca tcaagttgga cgaatccgtg tccgagtctg acaccatccg gagcatcagc     300
attgcttcgc agtgccctac cgcggggaac tcttgcctcg tttctggctg gggtctgctg     360
gcgaacggtg agctcacggg tgtgtgtctg ccctcttcaa ggaggtcctc tgcccagtcg     420 cggggggctga cccagagctc tgcgtcccag gcagaatgcc taccgtgctg cagtgcgtga     480
acgtgtcggt ggtgtctgag gaggtctgca gtaagctcta tgacccgctg taccacccca     540
gcatgttctg cgccggcgga gggcaagacc agaaggactc ctgcaacggt gactctgggg     600
ggcccctgat ctgcaacggg tacttgcagg gccttgtgtc tttcggaaaa gccccgtgtg     660
gccaagttgg cgtgccaggt gtctacacca acctctgcaa attcactgag tggatagaga     720
aaaccgtcca ggccagttaa ctctggggac tgggaaccca tgaaattgac ccccaaatac     780
atcctgcgga aggaattcag gaatatctgt tcccagcccc cctccctca ggcccaggag     840 tccaggcccc cagcccctcc tccctcaaac caagggtaca gatccccagc cctcctccc     900 tcagacccag gagtccagac cccccagccc ctcctccctc agaccaggga gtccagcccc     960
tcctccntca gacccaggag tccagacccc ccagcccctc ctccctcaga cccagggggtt    1020 gaggccccca cccctcctc cttcagagtc agaggtccaa gccccaaccc ctcgttccc      1080 cagacccaga ggtnnaggtc ccagcccctc ttccntcaga cccagnggtc caatgccacc    1140
tagatttccc ctgnacacag tgccccttg tggnagttg acccaacctt accagttggt      1200 tttttcatttt tngtcccttt cccctagatc cagaaataaa gtttaagaga ngngcaaaaa     1260
aaaaa                                                                  1265

<210> SEQ ID NO 174
<211> LENGTH: 1459
<212> TYPE: DNA
<213> ORGANISM: Homo sapien
```

<220> FEATURE:
<221> NAME/KEY: misc_feature
<222> LOCATION: (1)...(1459)
<223> OTHER INFORMATION: n = A,T,C or G

<400> SEQUENCE: 174

| | |
|---|---|
| ggtcagccgc acactgtttc agaagtgag tgcagagctc ctacaccatc gggctgggcc | 60 |
| tgcacagtct tgaggccgac caagagccag ggagccagat ggtggaggcc agcctctccg | 120 |
| tacggcaccc agagtacaac agaccttgc tcgctaacga cctcatgctc atcaagttgg | 180 |
| acgaatccgt gtccgagtct gacaccatcc ggagcatcag cattgcttcg cagtgccta | 240 |
| ccgcggggaa ctcttgcctc gtttctggct ggggtctgct ggcgaacggt gagctcacgg | 300 |
| gtgtgtgtct gccctcttca aggaggtcct ctgcccagtc gcggggggctg acccagagct | 360 |
| ctgcgtccca ggcagaatgc ctaccgtgct gcagtgcgtg aacgtgtcgg tggtgtctga | 420 |
| ngaggtctgc antaagctct atgacccgct gtaccacccc ancatgttct gcgccggcgg | 480 |
| agggcaagac cagaaggact cctgcaacgt gagagagggg aaagggggagg gcaggcgact | 540 |
| cagggaaggg tggagaaggg ggagacagag acacacaggg ccgcatggcg agatgcagag | 600 |
| atggagagac acagggag acagtgacaa ctagagagag aaactgagag aaacagagaa | 660 |
| ataaacacag gaataaagag aagcaaagga agagagaaac agaaacagac atggggaggc | 720 |
| agaaacacac acacatagaa atgcagttga ccttccaaca gcatgggggcc tgagggcggt | 780 |
| gacctccacc caatagaaaa tcctcttata acttttgact ccccaaaaac ctgactagaa | 840 |
| atagcctact gttgacgggg agccttacca ataacataaa tagtcgattt atgcatacgt | 900 |
| tttatgcatt catgatatac ctttgttgga attttttgat atttctaagc tacacagttc | 960 |
| gtctgtgaat ttttttaaat tgttgcaact ctcctaaaat ttttctgatg tgtttattga | 1020 |
| aaaaatccaa gtataagtgg acttgtgcat tcaaaccagg gttgttcaag ggtcaactgt | 1080 |
| gtacccagag ggaaacagtg acacagattc atagaggtga aacacgaaga gaaacaggaa | 1140 |
| aaatcaagac tctacaaaga ggctgggcag ggtggctcat gcctgtaatc ccagcacttt | 1200 |
| gggaggcgag gcaggcagat cacttgaggt aaggagttca agaccagcct ggccaaaatg | 1260 |
| gtgaaatcct gtctgtacta aaaatacaaa agttagctgg atatggtggc aggcgcctgt | 1320 |
| aatcccagct acttgggagg ctgaggcagg agaattgctt gaatatggga ggcagaggtt | 1380 |
| gaagtgagtt gagatcacac cactatactc cagctggggc aacagagtaa gactctgtct | 1440 |
| caaaaaaaaa aaaaaaaa | 1459 |

<210> SEQ ID NO 175
<211> LENGTH: 1167
<212> TYPE: DNA
<213> ORGANISM: Homo sapien
<220> FEATURE:
<221> NAME/KEY: misc_feature
<222> LOCATION: (1)...(1167)
<223> OTHER INFORMATION: n = A,T,C or G

<400> SEQUENCE: 175

| | |
|---|---|
| gcgcagccct ggcaggcggc actggtcatg gaaaacgaat tgttctgctc gggcgtcctg | 60 |
| gtgcatccgc agtgggtgct gtcagccgca cactgttttcc agaactccta caccatcggg | 120 |
| ctgggcctgc acagtcttga ggccgaccaa gagccaggga ccagatggt ggaggccagc | 180 |
| ctctccgtac ggcacccaga gtacaacaga ctccttgctcg ctaacgacct catgctcatc | 240 |
| aagttggacg aatccgtgtc cgagtctgac accatccgga gcatcagcat tgcttcgcag | 300 |

```
tgccctaccg cggggaactc ttgcctcgtn tctggctggg gtctgctggc gaacggcaga    360
atgcctaccg tgctgcactg cgtgaacgtg tcggtggtgt ctgaggangt ctgcagtaag    420
ctctatgacc cgctgtacca ccccagcatg ttctgcgccg gcggagggca agaccagaag    480
gactcctgca acggtgactc tgggggggccc ctgatctgca acgggtactt gcagggcctt    540
gtgtctttcg gaaaagcccc gtgtggccaa cttggcgtgc caggtgtcta caccaacctc    600
tgcaaattca ctgagtggat agagaaaacc gtccagncca gttaactctg gggactggga    660
acccatgaaa ttgaccccca aatacatcct gcggaangaa ttcaggaata tctgttccca    720
gcccctcctc cctcaggccc aggagtccag gcccccagcc cctcctccct caaaccaagg    780
gtacagatcc ccagcccctc ctccctcaga cccaggagtc cagacccccc agccctctcnt    840 ccntcagacc caggagtcca gcccctcctc cntcagacgc aggagtccag acccccagc    900 ccntcntccg tcagacccag gggtgcaggc ccccaacccc tcntcntca gagtcagagg    960 tccaagcccc caaccctcg ttccccagac ccagaggtnc aggtcccagc ccctcctccc    1020
tcagacccag cggtccaatg ccacctagan tntccctgta cacagtgccc ccttgtggca    1080
ngttgaccca accttaccag ttggttttc atttttgtc cctttcccct agatccagaa    1140
ataaagtnta agagaagcgc aaaaaaa                                        1167
```

<210> SEQ ID NO 176
<211> LENGTH: 205
<212> TYPE: PRT
<213> ORGANISM: Homo sapien
<220> FEATURE:
<221> NAME/KEY: VARIANT
<222> LOCATION: (1)...(205)
<223> OTHER INFORMATION: Xaa = Any Amino Acid

<400> SEQUENCE: 176

```
Met Glu Asn Glu Leu Phe Cys Ser Gly Val Leu Val His Pro Gln Trp
 1               5                  10                  15

Val Leu Ser Ala Ala His Cys Phe Gln Asn Ser Tyr Thr Ile Gly Leu
            20                  25                  30

Gly Leu His Ser Leu Glu Ala Asp Gln Glu Pro Gly Ser Gln Met Val
        35                  40                  45

Glu Ala Ser Leu Ser Val Arg His Pro Glu Tyr Asn Arg Leu Leu Leu
    50                  55                  60

Ala Asn Asp Leu Met Leu Ile Lys Leu Asp Glu Ser Val Ser Glu Ser
65                  70                  75                  80

Asp Thr Ile Arg Ser Ile Ser Ile Ala Ser Gln Cys Pro Thr Ala Gly
                85                  90                  95

Asn Ser Cys Leu Val Ser Gly Trp Gly Leu Leu Ala Asn Gly Arg Met
            100                 105                 110

Pro Thr Val Leu His Cys Val Asn Val Ser Val Ser Glu Xaa Val
        115                 120                 125

Cys Ser Lys Leu Tyr Asp Pro Leu Tyr His Pro Ser Met Phe Cys Ala
    130                 135                 140

Gly Gly Gly Gln Asp Gln Lys Asp Ser Cys Asn Gly Asp Ser Gly Gly
145                 150                 155                 160

Pro Leu Ile Cys Asn Gly Tyr Leu Gln Gly Leu Val Ser Phe Gly Lys
                165                 170                 175
```

```
Ala Pro Cys Gly Gln Leu Gly Val Pro Gly Val Tyr Thr Asn Leu Cys
            180                 185                 190

Lys Phe Thr Glu Trp Ile Glu Lys Thr Val Gln Xaa Ser
            195                 200                 205

<210> SEQ ID NO 177
<211> LENGTH: 1119
<212> TYPE: DNA
<213> ORGANISM: Homo sapien

<400> SEQUENCE: 177
gcgcactcgc agccctggca ggcggcactg gtcatggaaa acgaattgtt ctgctcgggc      60
gtcctggtgc atccgcagtg ggtgctgtca gccgcacact gtttccagaa ctcctacacc     120
atcgggctgg gcctgcacag tcttgaggcc gaccaagagc cagggagcca gatggtggag     180
gccagcctct ccgtacggca cccagagtac aacagaccct tgctcgctaa cgacctcatg     240
ctcatcaagt tggacgaatc cgtgtccgag tctgacacca tccggagcat cagcattgct     300
tcgcagtgcc ctaccgcggg gaactcttgc ctcgtttctg gctggggtct gctggcgaac     360
gatgctgtga ttgccatcca gtcccagact gtgggaggct gggagtgtga aagctttcc      420 caaccctggc agggttgtac catttcggca acttccagtg caaggacgtc ctgctgcatc     480
ctcactgggt gctcactact gctcactgca tcacccggaa cactgtgatc aactagccag     540
caccatagtt ctccgaagtc agactatcat gattactgtg ttgactgtgc tgtctattgt     600
actaaccatg ccgatgttta ggtgaaatta gcgtcacttg gcctcaacca tcttggtatc     660
cagttatcct cactgaattg agatttcctg cttcagtgtc agccattccc acataatttc     720
tgacctacag aggtgaggga tcatatagct cttcaaggat gctggtactc ccctcacaaa     780
ttcatttctc ctgttgtagt gaaaggtgcg ccctctggag cctcccaggg tgggtgtgca     840
ggtcacaatg atgaatgtat gatcgtgttc ccattaccca aagcctttaa atccctcatg     900
ctcagtacac cagggcaggt ctagcatttc ttcatttagt gtatgctgtc cattcatgca     960
accacctcag gactcctgga ttctctgcct agttgagctc ctgcatgctg cctccttggg    1020
gaggtgaggg agagggccca tggttcaatg ggatctgtgc agttgtaaca cattaggtgc    1080
ttaataaaca gaagctgtga tgttaaaaaa aaaaaaaaa                           1119

<210> SEQ ID NO 178
<211> LENGTH: 164
<212> TYPE: PRT
<213> ORGANISM: Homo sapien
<220> FEATURE:
<221> NAME/KEY: VARIANT
<222> LOCATION: (1)...(164)
<223> OTHER INFORMATION: Xaa = Any Amino Acid

<400> SEQUENCE: 178

Met Glu Asn Glu Leu Phe Cys Ser Gly Val Leu Val His Pro Gln Trp
  1               5                  10                  15

Val Leu Ser Ala Ala His Cys Phe Gln Asn Ser Tyr Thr Ile Gly Leu
             20                  25                  30

Gly Leu His Ser Leu Glu Ala Asp Gln Glu Pro Gly Ser Gln Met Val
         35                  40                  45

Glu Ala Ser Leu Ser Val Arg His Pro Glu Tyr Asn Arg Pro Leu Leu
     50                  55                  60

Ala Asn Asp Leu Met Leu Ile Lys Leu Asp Glu Ser Val Ser Glu Ser
 65                  70                  75                  80
```

-continued

```
Asp Thr Ile Arg Ser Ile Ser Ile Ala Ser Gln Cys Pro Thr Ala Gly
                85                  90                  95

Asn Ser Cys Leu Val Ser Gly Trp Gly Leu Leu Ala Asn Asp Ala Val
            100                 105                 110

Ile Ala Ile Gln Ser Xaa Thr Val Gly Gly Trp Glu Cys Glu Lys Leu
        115                 120                 125

Ser Gln Pro Trp Gln Gly Cys Thr Ile Ser Ala Thr Ser Ala Arg
    130                 135                 140

Thr Ser Cys Cys Ile Leu Thr Gly Cys Ser Leu Leu Thr Ala Ser
145                 150                 155                 160

Pro Gly Thr Leu
```

<210> SEQ ID NO 179
<211> LENGTH: 250
<212> TYPE: DNA
<213> ORGANISM: Homo sapien

<400> SEQUENCE: 179

| | | | | | |
|---|---|---|---|---|---|
| ctggagtgcc | ttggtgtttc | aagcccctgc | aggaagcaga | atgcaccttc | tgaggcacct | 60 |
| ccagctgccc | ccggccgggg | gatgcgaggc | tcggagcacc | cttgcccggc | tgtgattgct | 120 |
| gccaggcact | gttcatctca | gcttttctgt | ccctttgctc | ccggcaagcg | cttctgctga | 180 |
| aagttcatat | ctggagcctg | atgtcttaac | gaataaaggt | cccatgctcc | acccgaaaaa | 240 |
| aaaaaaaaaa | | | | | | 250 |

<210> SEQ ID NO 180
<211> LENGTH: 202
<212> TYPE: DNA
<213> ORGANISM: Homo sapien

<400> SEQUENCE: 180

| | | | | | |
|---|---|---|---|---|---|
| actagtccag | tgtggtggaa | ttccattgtg | ttgggcccaa | cacaatggct | acctttaaca | 60 |
| tcacccagac | cccgcccctg | cccgtgcccc | acgctgctgc | taacgacagt | atgatgctta | 120 |
| ctctgctact | cggaaactat | ttttatgtaa | ttaatgtatg | ctttcttgtt | tataaatgcc | 180 |
| tgatttaaaa | aaaaaaaaaa | aa | | | | 202 |

<210> SEQ ID NO 181
<211> LENGTH: 558
<212> TYPE: DNA
<213> ORGANISM: Homo sapien
<220> FEATURE:
<221> NAME/KEY: misc_feature
<222> LOCATION: (1)...(558)
<223> OTHER INFORMATION: n = A,T,C or G

<400> SEQUENCE: 181

| | | | | | |
|---|---|---|---|---|---|
| tccytttgkt | naggtttkkg | agacamccck | agacctwaan | ctgtgtcaca | gacttcyngg | 60 |
| aatgtttagg | cagtgctagt | aatttcytcg | taatgattct | gttattactt | tcctnattct | 120 |
| ttattcctct | ttcttctgaa | gattaatgaa | gttgaaaatt | gaggtggata | aatacaaaaa | 180 |
| ggtagtgtga | tagtataagt | atctaagtgc | agatgaaagt | gtgttatata | tatccattca | 240 |
| aaattatgca | agttagtaat | tactcagggt | taactaaatt | actttaatat | gctgttgaac | 300 |
| ctactctgtt | ccttggctag | aaaaaattat | aaacaggact | ttgttagttt | gggaagccaa | 360 |
| attgataata | ttctatgttc | taaaagttgg | gctatacata | aattattaag | aaatatggaw | 420 |
| ttttattccc | aggaatatgg | kgttcatttt | atgaatatta | cscrggatag | awgtwtgagt | 480 |

| | |
|---|---:|
| aaaaycagtt ttggtwaata ygtwaatatg tcmtaaataa acaakgcttt gacttatttc | 540 |
| caaaaaaaaa aaaaaaaa | 558 |

<210> SEQ ID NO 182
<211> LENGTH: 479
<212> TYPE: DNA
<213> ORGANISM: Homo sapien
<220> FEATURE:
<221> NAME/KEY: misc_feature
<222> LOCATION: (1)...(479)
<223> OTHER INFORMATION: n = A,T,C or G

<400> SEQUENCE: 182

| | |
|---|---:|
| acagggwttk grggatgcta agsccccrga rwtygtttga tccaaccctg gcttwttttc | 60 |
| agagggaaa atgggccta gaagttacag mscatytagy tggtgcgmtg gcaccccctgg | 120 |
| cstcacacag astcccgagt agctgggact acaggcacac agtcactgaa gcaggccctg | 180 |
| ttwgcaattc acgttgccac ctccaactta aacattcttc atatgtgatg tccttagtca | 240 |
| ctaaggttaa actttcccac ccagaaaagg caacttagat aaaatcttag agtactttca | 300 |
| tactmttcta agtcctcttc cagcctcact kkgagtcctm cytgggggtt gataggaant | 360 |
| ntctcttggc tttctcaata aartctctat ycatctcatg tttaatttgg tacgcatara | 420 |
| awtgstgara aaattaaaat gttctggtty mactttaaaa araaaaaaaa aaaaaaaaa | 479 |

<210> SEQ ID NO 183
<211> LENGTH: 384
<212> TYPE: DNA
<213> ORGANISM: Homo sapien

<400> SEQUENCE: 183

| | |
|---|---:|
| aggcgggagc agaagctaaa gccaaagccc aagaagagtg gcagtgccag cactggtgcc | 60 |
| agtaccagta ccaataacag tgccagtgcc agtgccagca ccagtggtgg cttcagtgct | 120 |
| ggtgccagcc tgaccgccac tctcacattt gggctcttcg ctggccttgg tggagctggt | 180 |
| gccagcacca gtggcagctc tggtgcctgt ggtttctcct acaagtgaga ttttagatat | 240 |
| tgttaatcct gccagtcttt ctcttcaagc cagggtgcat cctcagaaac ctactcaaca | 300 |
| cagcactcta ggcagccact atcaatcaat tgaagttgac actctgcatt aratctatt | 360 |
| gccatttcaa aaaaaaaaaa aaaa | 384 |

<210> SEQ ID NO 184
<211> LENGTH: 496
<212> TYPE: DNA
<213> ORGANISM: Homo sapien
<220> FEATURE:
<221> NAME/KEY: misc_feature
<222> LOCATION: (1)...(496)
<223> OTHER INFORMATION: n = A,T,C or G

<400> SEQUENCE: 184

| | |
|---|---:|
| accgaattgg gaccgctggc ttataagcga tcatgtyynt ccrgtatkac ctcaacgagc | 60 |
| agggagatcg agtctatacg ctgaagaaat ttgacccgat gggacaacag acctgctcag | 120 |
| cccatcctgc tcggttctcc ccagatgaca aatactctsg acaccgaatc accatcaaga | 180 |
| aacgcttcaa ggtgctcatg acccagcaac cgcgccctgt cctctgaggg tcccttaaac | 240 |
| tgatgtcttt tctgccacct gttacccctc ggagactccg taaccaaact cttcggactg | 300 |
| tgagccctga tgccttttg ccagccatac tcttttggcat ccagtctctc gtggcgattg | 360 |
| attatgcttg tgtgaggcaa tcatggtggc atcaccccata aagggaacac atttgactt | 420 |

-continued

| | |
|---|---|
| tttttctcat attttaaatt actacmagaw tattwmagaw waaatgawtt gaaaaactst | 480 |
| taaaaaaaaa aaaaaa | 496 |

<210> SEQ ID NO 185
<211> LENGTH: 384
<212> TYPE: DNA
<213> ORGANISM: Homo sapien

<400> SEQUENCE: 185

| | |
|---|---|
| gctggtagcc tatggcgkgg cccacggagg ggctcctgag gccacggrac agtgacttcc | 60 |
| caagtatcyt gcgcsgcgtc ttctaccgtc cctacctgca gatcttcggg cagattcccc | 120 |
| aggaggacat ggacgtggcc ctcatggagc acagcaactg ytcgtcggag cccggcttct | 180 |
| gggcacaccc tcctggggcc caggcgggca cctgcgtctc ccagtatgcc aactggctgg | 240 |
| tggtgctgct cctcgtcatc ttcctgctcg tggccaacat cctgctggtc aacttgctca | 300 |
| ttgccatgtt cagttacaca ttcggcaaag tacagggcaa cagcgatctc tactgggaag | 360 |
| gcgcagcgtt accgcctcat ccgg | 384 |

<210> SEQ ID NO 186
<211> LENGTH: 577
<212> TYPE: DNA
<213> ORGANISM: Homo sapien
<220> FEATURE:
<221> NAME/KEY: misc_feature
<222> LOCATION: (1)...(577)
<223> OTHER INFORMATION: n = A,T,C or G

<400> SEQUENCE: 186

| | |
|---|---|
| gagttagctc ctccacaacc ttgatgaggt cgtctgcagt ggcctctcgc ttcataccgc | 60 |
| tnccatcgtc atactgtagg tttgccacca cytcctggca tcttggggcg gcntaatatt | 120 |
| ccaggaaact ctcaatcaag tcaccgtcga tgaaacctgt gggctggttc tgtcttccgc | 180 |
| tcggtgtgaa aggatctccc agaaggagtg ctcgatcttc cccacacttt tgatgacttt | 240 |
| attgagtcga ttctgcatgt ccagcaggag gttgtaccag ctctctgaca gtgaggtcac | 300 |
| cagccctatc atgccgttga mcgtgccgaa garcaccgag ccttgtgtgg gggkkgaagt | 360 |
| ctcacccaga ttctgcatta ccagagagcc gtggcaaaag acattgacaa actcgcccag | 420 |
| gtggaaaaag amcamctcct ggargtgctn gccgctcctc gtcmgttggt ggcagcgctw | 480 |
| tccttttgac acacaaacaa gttaaaggca ttttcagccc cagaaantt gtcatcatcc | 540 |
| aagatntcgc acagcactna tccagttggg attaaat | 577 |

<210> SEQ ID NO 187
<211> LENGTH: 534
<212> TYPE: DNA
<213> ORGANISM: Homo sapien
<220> FEATURE:
<221> NAME/KEY: misc_feature
<222> LOCATION: (1)...(534)
<223> OTHER INFORMATION: n = A,T,C or G

<400> SEQUENCE: 187

| | |
|---|---|
| aacatcttcc tgtataatgc tgtgtaatat cgatccgatn ttgtctgstg agaatycatw | 60 |
| actkggaaaa gmaacattaa agcctggaca ctggtattaa aattcacaat atgcaacact | 120 |
| ttaaacagtg tgtcaatctg ctcccyynac tttgtcatca ccagtctggg aakaagggta | 180 |
| tgccctattc acacctgtta aaagggcgct aagcattttt gattcaacat ctttttttttt | 240 |
| gacacaagtc cgaaaaaagc aaaagtaaac agttatyaat ttgttagcca attcactttc | 300 |

```
ttcatgggac agagccatyt gatttaaaaa gcaaattgca taatattgag cttygggagc    360
tgatatttga gcggaagagt agcctttcta cttcaccaga cacaactccc tttcatattg    420
ggatgttnac naaagtwatg tctctwacag atgggatgct tttgtggcaa ttctgttctg    480
aggatctccc agtttattta ccacttgcac aagaaggcgt tttcttcctc aggc          534
```

<210> SEQ ID NO 188
<211> LENGTH: 761
<212> TYPE: DNA
<213> ORGANISM: Homo sapien
<220> FEATURE:
<221> NAME/KEY: misc_feature
<222> LOCATION: (1)...(761)
<223> OTHER INFORMATION: n = A,T,C or G

<400> SEQUENCE: 188

```
agaaaccagt atctctnaaa acaacctctc ataccttgtg gacctaattt tgtgtgcgtg     60
tgtgtgtgcg cgcatattat atagacaggc acatcttttt tacttttgta aaagcttatg    120
cctctttggt atctatatct gtgaaagttt aatgatctg ccataatgtc ttggggacct    180
ttgtcttctg tgtaaatggt actagagaaa acacctatnt tatgagtcaa tctagttngt    240
tttattcgac atgaaggaaa tttccagatn acaacactna caaactctcc ctkgackarg    300
ggggacaaag aaaagcaaaa ctgamcataa raaacaatwa cctggtgaga arttgcataa    360
acagaaatwr ggtagtatat tgaarnacag catcattaaa rmgttwtktt wttctcccct   420
gcaaaaaaca tgtacngact tcccgttgag taatgccaag ttgttttttt tatnataaaa    480
cttgcccttc attacatgtt tnaaagtggt gtggtgggcc aaaatattga aatgatggaa    540
ctgactgata aagctgtaca ataagcagt gtgcctaaca agcaacacag taatgttgac    600
atgcttaatt cacaaatgct aatttcatta taaatgtttg ctaaaataca ctttgaacta    660
tttttctgtn ttcccagagc tgagatntta gattttatgt agtataagt gaaaaantac     720
gaaaataata acattgaaga aaaananaaa aaanaaaaaa a                         761
```

<210> SEQ ID NO 189
<211> LENGTH: 482
<212> TYPE: DNA
<213> ORGANISM: Homo sapien
<220> FEATURE:
<221> NAME/KEY: misc_feature
<222> LOCATION: (1)...(482)
<223> OTHER INFORMATION: n = A,T,C or G

<400> SEQUENCE: 189

```
ttttttttt tttgccgatn ctactatttt attgcaggan gtgggggtgt atgcaccgca      60
caccggggct atnagaagca agaaggaagg agggagggca cagccccttg ctgagcaaca    120
aagccgcctg ctgccttctc tgtctgtctc ctggtgcagg cacatgggga gaccttcccc    180
aaggcagggg ccaccagtcc aggggtggga atacaggggg tgggangtgt gcataagaag    240
tgataggcac aggccacccg gtacagaccc ctcggctcct gacaggtnga tttcgaccag    300
gtcattgtgc cctgcccagg cacagcgtan atctggaaaa gacagaatgc tttccttttc    360
aaatttggct ngtcatngaa ngggcantt tccaanttng ctnggtctt ggtacncttg     420
gttcggccca gctccncgtc caaaaantat tcacccnnct ccnaattgct tgcnggnccc    480
cc                                                                     482
```

<210> SEQ ID NO 190
<211> LENGTH: 471
<212> TYPE: DNA
<213> ORGANISM: Homo sapien
<220> FEATURE:
<221> NAME/KEY: misc_feature
<222> LOCATION: (1)...(471)
<223> OTHER INFORMATION: n = A,T,C or G

<400> SEQUENCE: 190
tttttttttt ttttaaaaca gttttcaca acaaaattta ttagaagaat agtggttttg      60
aaaactctcg catccagtga gaactaccat acaccacatt acagctngga atgtnctcca    120
aatgtctggt caaatgatac aatggaacca ttcaatctta cacatgcacg aaagaacaag    180
cgcttttgac atacaatgca caaaaaaaaa agggggggg gaccacatgg attaaaattt    240
taagtactca tcacatacat taagacacag ttctagtcca gtcnaaaatc agaactgcnt    300
tgaaaaattt catgtatgca atccaaccaa agaacttnat tggtgatcat gantnctcta    360
ctacatcnac cttgatcatt gccaggaacn aaaagttnaa ancacncngt acaaaaanaa    420
tctgtaattn anttcaacct ccgtacngaa aaatnttnnt tatacactcc c             471

<210> SEQ ID NO 191
<211> LENGTH: 402
<212> TYPE: DNA
<213> ORGANISM: Homo sapien
<220> FEATURE:
<221> NAME/KEY: misc_feature
<222> LOCATION: (1)...(402)
<223> OTHER INFORMATION: n = A,T,C or G

<400> SEQUENCE: 191
gagggattga aggtctgttc tastgtcggm ctgttcagcc accaactcta acaagttgct      60
gtcttccact cactgtctgt aagcttttta acccagacwg tatcttcata aatagaacaa    120
attcttcacc agtcacatct tctaggacct ttttggattc agttagtata agctcttcca    180
cttcctttgt taagacttca tctggtaaag tcttaagttt tgtagaaagg aattyaattg    240
ctcgttctct aacaatgtcc tctccttgaa gtatttggct gaacaaccca cctaaagtcc    300
ctttgtgcat ccatttaaa tatacttaat agggcattgk tncactaggt taaattctgc    360
aagagtcatc tgtctgcaaa agttgcgtta gtatatctgc ca                       402

<210> SEQ ID NO 192
<211> LENGTH: 601
<212> TYPE: DNA
<213> ORGANISM: Homo sapien
<220> FEATURE:
<221> NAME/KEY: misc_feature
<222> LOCATION: (1)...(601)
<223> OTHER INFORMATION: n = A,T,C or G

<400> SEQUENCE: 192
gagctcggat ccaataatct tgtctgagg gcagcacaca tatncagtgc catggnaact      60
ggtctacccc acatgggagc agcatgccgt agntatataa ggtcattccc tgagtcagac    120
atgcytyttt gaytaccgtg tgccaagtgc tggtgattct yaacacacyt ccatcccgyt    180
cttttgtgga aaaactggca cttktctgga actagcarga catcacttac aaattcaccc    240
acgagacact tgaaaggtgt aacaaagcga ytcttgcatt gcttttgtc cctccggcac    300
cagttgtcaa tactaacccg ctggtttgcc tccatcacat ttgtgatctg tagctctgga    360
tacatctcct gacagtactg aagaacttct tcttttgttt caaaagcarc tcttggtgcc    420

```
tgttggatca ggttcccatt tcccagtcyg aatgttcaca tggcatattt wacttcccac      480
aaaacattgc gatttgaggc tcagcaacag caaatcctgt tccggcattg gctgcaagag      540
cctcgatgta gccggccagc gccaaggcag gcgccgtgag ccccaccagc agcagaagca      600
g                                                                     601
```

<210> SEQ ID NO 193
<211> LENGTH: 608
<212> TYPE: DNA
<213> ORGANISM: Homo sapien
<220> FEATURE:
<221> NAME/KEY: misc_feature
<222> LOCATION: (1)...(608)
<223> OTHER INFORMATION: n = A,T,C or G

<400> SEQUENCE: 193

```
atacagccca natcccacca cgaagatgcg cttgttgact gagaacctga tgcggtcact      60
ggtcccgctg tagccccagc gactctccac ctgctgaaag cggttgatgc tgcactcytt     120
cccaacgcag gcagmagcgg gsccggtcaa tgaactccay tcgtggcttg gggtkgacgg     180
tkaagtgcag gaagaggctg accacctcgc ggtccaccag gatgcccgac tgtgcgggac     240
ctgcagcgaa actcctcgat ggtcatgagc gggaagcgaa tgaggcccag ggccttgccc     300
agaaccttcc gcctgttctc tggcgtcacc tgcagctgct gccgctgaca ctcggcctcg     360
gaccagcgga caaacggcrt tgaacagccg cacctcacgg atgcccagtg tgtcgcgctc     420
caggammgsc accagcgtgt ccaggtcaat gtcggtgaag ccctccgcgg gtratggcgt     480
ctgcagtgtt tttgtcgatg ttctccaggc acaggctggc cagctgcggt tcatcgaaga     540
gtcgcgcctg cgtgagcagc atgaaggcgt tgtcggctcg cagttcttct tcaggaactc     600
cacgcaat                                                             608
```

<210> SEQ ID NO 194
<211> LENGTH: 392
<212> TYPE: DNA
<213> ORGANISM: Homo sapien
<220> FEATURE:
<221> NAME/KEY: misc_feature
<222> LOCATION: (1)...(392)
<223> OTHER INFORMATION: n = A,T,C or G

<400> SEQUENCE: 194

```
gaacggctgg accttgcctc gcattgtgct tgctggcagg gaataccttg gcaagcagyt      60
ccagtccgag cagccccaga ccgctgccgc ccgaagctaa gcctgcctct ggccttcccc     120
tccgcctcaa tgcagaacca gtagtgggag cactgtgttt agagttaaga gtgaacactg     180
tttgatttta cttgggaatt tcctctgtta tatagctttt cccaatgcta atttccaaac     240
aacaacaaca aataacatg tttgcctgtt aagttgtata aaagtaggtg attctgtatt     300
taaagaaaat attactgtta catatactgc ttgcaatttc tgtatttatt gktnctstgg     360
aaataaatat agttattaaa ggttgtcant cc                                   392
```

<210> SEQ ID NO 195
<211> LENGTH: 502
<212> TYPE: DNA
<213> ORGANISM: Homo sapien
<220> FEATURE:
<221> NAME/KEY: misc_feature
<222> LOCATION: (1)...(502)
<223> OTHER INFORMATION: n = A,T,C or G

```
<400> SEQUENCE: 195
ccsttkgagg ggtkaggkyc cagttyccga gtggaagaaa caggccagga gaagtgcgtg     60
ccgagctgag gcagatgttc ccacagtgac ccccagagcc stgggstata gtytctgacc    120
cctcncaagg aaagaccacs ttctggggac atgggctgga gggcaggacc tagaggcacc    180
aagggaaggc cccattccgg ggstgttccc cgaggaggaa gggaagdggc tctgtgtgcc    240
ccccasgagg aagaggccct gagtcctggg atcagacacc ccttcacgtg tatccccaca    300
caaatgcaag ctcaccaagg tcccctctca gtccccttcc stacaccctg amcggccact    360
gscscacacc cacccagagc acgccacccg ccatggggar tgtgctcaag gartcgcngg    420
gcarcgtgga catctngtcc cagaaggggg cagaatctcc aatagangga ctgarcmstt    480
gctnanaaaa aaaaanaaaa aa                                              502

<210> SEQ ID NO 196
<211> LENGTH: 665
<212> TYPE: DNA
<213> ORGANISM: Homo sapien
<220> FEATURE:
<221> NAME/KEY: misc_feature
<222> LOCATION: (1)...(665)
<223> OTHER INFORMATION: n = A,T,C or G

<400> SEQUENCE: 196
ggttacttgg tttcattgcc accacttagt ggatgtcatt tagaaccatt tgtctgctc     60 cctctggaag ccttgcgcag agcggacttt gtaattgttg gagaataact gctgaatttt    120
wagctgtttk gagttgatts gcaccactgc acccacaact tcaatatgaa acyawttga    180 actwatttat tatcttgtga aaagtataac aatgaaaatt tgttcatac tgtattkatc    240 aagtatgatg aaaagcaawa gatatatatt cttttattat gttaaattat gattgccatt    300
attaatcggc aaaatgtgga gtgtatgttc ttttcacagt aatatatgcc ttttgtaact    360
tcacttggtt attttattgt aaatgartta caaaattctt aatttaagar aatggtatgt    420
watatttatt tcattaattt ctttcctkgt ttacgtwaat tttgaaaaga wtgcatgatt    480
tcttgacaga aatcgatctt gatgctgtgg aagtagtttg acccacatcc ctatgagttt    540
ttcttagaat gtataaaggt tgtagcccat cnaacttcaa agaaaaaaat gaccacatac    600
tttgcaatca ggctgaaatg tggcatgctn ttctaattcc aactttataa actagcaaan    660
aagtg                                                                665

<210> SEQ ID NO 197
<211> LENGTH: 492
<212> TYPE: DNA
<213> ORGANISM: Homo sapien
<220> FEATURE:
<221> NAME/KEY: misc_feature
<222> LOCATION: (1)...(492)
<223> OTHER INFORMATION: n = A,T,C or G

<400> SEQUENCE: 197
ttttnttttt ttttttttgc aggaaggatt ccatttattg tggatgcatt ttcacaatat     60
atgtttattg gagcgatcca ttatcagtga aaagtatcaa gtgtttataa nattttagg    120 aaggcagatt cacagaacat gctngtcngc ttgcagtttt acctcgtana gatnacagag    180
aattatagtc naaccagtaa acnaggaatt tacttttcaa aagattaaat ccaaactgaa    240
caaaattcta ccctgaaact tactccatcc aaatattgga ataanagtca gcagtgatac    300
attctcttct gaactttaga ttttctagaa aaatatgtaa tagtgatcag gaagagctct    360
```

| | |
|---|---|
| tgttcaaaag tacaacnaag caatgttccc ttaccatagg ccttaattca aactttgatc | 420 |
| catttcactc ccatcacggg agtcaatgct acctgggaca cttgtatttt gttcatnctg | 480 |
| ancntggctt aa | 492 |

<210> SEQ ID NO 198
<211> LENGTH: 478
<212> TYPE: DNA
<213> ORGANISM: Homo sapien
<220> FEATURE:
<221> NAME/KEY: misc_feature
<222> LOCATION: (1)...(478)
<223> OTHER INFORMATION: n = A,T,C or G

<400> SEQUENCE: 198

| | |
|---|---|
| tttntttgn atttcantct gtannaanta ttttcattat gtttattana aaaatatnaa | 60 |
| tgtntccacn acaaatcatn ttacntnagt aagaggccan ctacattgta caacatacac | 120 |
| tgagtatatt ttgaaaagga caagtttaaa gtanacncat attgccganc atancacatt | 180 |
| tatacatggc ttgattgata tttagcacag canaaactga gtgagttacc agaaanaaat | 240 |
| natatatgtc aatcngattt aagatacaaa acagatccta tggtacatan catcntgtag | 300 |
| gagttgtggc tttatgttta ctgaaagtca atgcagttcc tgtacaaaga gatggccgta | 360 |
| agcattctag tacctctact ccatggttaa gaatcgtaca cttatgttta catatgtnca | 420 |
| gggtaagaat tgtgttaagt naanttatgg agaggtccan gagaaaaatt tgatncaa | 478 |

<210> SEQ ID NO 199
<211> LENGTH: 482
<212> TYPE: DNA
<213> ORGANISM: Homo sapien
<220> FEATURE:
<221> NAME/KEY: misc_feature
<222> LOCATION: (1)...(482)
<223> OTHER INFORMATION: n = A,T,C or G

<400> SEQUENCE: 199

| | |
|---|---|
| agtgacttgt cctccaacaa aaccccttga tcaagtttgt ggcactgaca atcagaccta | 60 |
| tgctagttcc tgtcatctat tcgctactaa atgcagactg gaggggacca aaaagggca | 120 |
| tcaactccag ctggattatt ttggagcctg caaatctatt cctacttgta cggactttga | 180 |
| agtgattcag tttcctctac ggatgagaga ctggctcaag aatatcctca tgcagcttta | 240 |
| tgaagccnac tctgaacacg ctggttatct nagatgagaa ncagaaaat aaagtcnaga | 300 |
| aaatttacct ggangaaaag aggctttngg ctggggacca tcccattgaa ccttctctta | 360 |
| anggacttta agaanaaact accacatgtn tgtngtatcc tggtgccngg ccgtttantg | 420 |
| aacntngacn ncacccttnt ggaatanant cttgacngcn tcctgaactt gctcctctgc | 480 |
| ga | 482 |

<210> SEQ ID NO 200
<211> LENGTH: 270
<212> TYPE: DNA
<213> ORGANISM: Homo sapien
<220> FEATURE:
<221> NAME/KEY: misc_feature
<222> LOCATION: (1)...(270)
<223> OTHER INFORMATION: n = A,T,C or G

<400> SEQUENCE: 200

| | |
|---|---|
| cggccgcaag tgcaactcca gctggggccg tgcggacgaa gattctgcca gcagttggtc | 60 |
| cgactgcgac gacggcggcg gcgacagtcg caggtgcagc gcgggcgcct ggggtcttgc | 120 |

```
aaggctgagc tgacgccgca gaggtcgtgt cacgtcccac gaccttgacg ccgtcgggga      180
cagccggaac agagcccggt gaangcggga ggcctcgggg agcccctcgg gaagggcggc      240
ccgagagata cgcaggtgca ggtggccgcc                                      270
```

<210> SEQ ID NO 201
<211> LENGTH: 419
<212> TYPE: DNA
<213> ORGANISM: Homo sapien
<220> FEATURE:
<221> NAME/KEY: misc_feature
<222> LOCATION: (1)...(419)
<223> OTHER INFORMATION: n = A,T,C or G

<400> SEQUENCE: 201

```
tttttttttt ttttggaatc tactgcgagc acagcaggtc agcaacaagt ttattttgca      60
gctagcaagg taacagggta gggcatggtt acatgttcag gtcaacttcc tttgtcgtgg     120
ttgattggtt tgtctttatg ggggcggggt ggggtagggg aaancgaagc anaantaaca     180
tggagtgggt gcaccctccc tgtagaacct ggttacnaaa gcttggggca gttcacctgg     240
tctgtgaccg tcattttctt gacatcaatg ttattagaag tcaggatatc ttttagagag     300
tccactgtnt ctggagggag attagggttt cttgccaana tccaancaaa atccacntga     360
aaaagttgga tgatncangt acngaatacc ganggcatan ttctcatant cggtggcca      419
```

<210> SEQ ID NO 202
<211> LENGTH: 509
<212> TYPE: DNA
<213> ORGANISM: Homo sapien
<220> FEATURE:
<221> NAME/KEY: misc_feature
<222> LOCATION: (1)...(509)
<223> OTHER INFORMATION: n = A,T,C or G

<400> SEQUENCE: 202

```
tttnttttt ttttttttt tttttttt tttttttt tttttttt ttttttttt              60 tggcacttaa tccatttta tttcaaaatg tctacaaant ttnaatncnc cattatacng     120 gtnatttnc aaaatctaaa nnttattcaa atntnagcca aantccttac ncaaatnnaa     180
tacncncaaa aatcaaaaat atacntntct ttcagcaaac ttngttacat aaattaaaaa     240
aatatatacg gctggtgttt tcaaagtaca attatcttaa cactgcaaac atntttnnaa     300
ggaactaaaa taaaaaaaaa cactnccgca aaggttaaag ggaacaacaa attcnttta     360 caacancnnc nattataaaa atcatatctc aaatcttagg ggaatatata cttcacacng    420
ggatcttaac ttttactnca ctttgtttat tttttttanaa ccattgtntt gggcccaaca    480
caatggnaat nccnccncnc tggactagt                                        509
```

<210> SEQ ID NO 203
<211> LENGTH: 583
<212> TYPE: DNA
<213> ORGANISM: Homo sapien
<220> FEATURE:
<221> NAME/KEY: misc_feature
<222> LOCATION: (1)...(583)
<223> OTHER INFORMATION: n = A,T,C or G

<400> SEQUENCE: 203

```
tttttttttt ttttttttga ccccctctt ataaaaaaca agttaccatt ttatttact        60 tacacatatt tatttaaa ttggtattag atattcaaaa ggcagctttt aaaatcaaac       120
taaatggaaa ctgccttaga tacataattc ttaggaatta gcttaaaatc tgcctaaagt     180
```

```
gaaaatcttc tctagctctt ttgactgtaa attttttgact cttgtaaaac atccaaattc    240 attttttcttg tctttaaaat tatctaatct ttccattttt tccctattcc aagtcaattt    300
gcttctctag cctcatttcc tagctcttat ctactattag taagtggctt ttttcctaaa    360
agggaaaaca ggaagagana atggcacaca aaacaaacat tttatattca tatttctacc    420
tacgttaata aaatagcatt ttgtgaagcc agctcaaaag aaggcttaga tccttttatg    480 tccatttttag tcactaaacg atatcnaaag tgccagaatg caaaaggttt gtgaacattt    540
attcaaaagc taatataaga tatttcacat actcatcttt ctg                      583
```

<210> SEQ ID NO 204
<211> LENGTH: 589
<212> TYPE: DNA
<213> ORGANISM: Homo sapien
<220> FEATURE:
<221> NAME/KEY: misc_feature
<222> LOCATION: (1)...(589)
<223> OTHER INFORMATION: n = A,T,C or G

<400> SEQUENCE: 204

```
ttttttttnt tttttttttt ttttttnctc ttcttttttt ttganaatga ggatcgagtt     60
tttcactctc tagatagggc atgaagaaaa ctcatctttc cagctttaaa ataacaatca    120
aatctcttat gctatatcat attttaagtt aaactaatga gtcactggct tatcttctcc    180
tgaaggaaat ctgttcattc ttctcattca tatagttata tcaagtacta ccttgcatat    240
tgagaggttt ttcttctcta tttacacata tatttccatg tgaatttgta tcaaaccttt    300
attttcatgc aaactagaaa ataatgtntt cttttgcata agagaagaga acaatatnag    360
cattacaaaa ctgctcaaat tgtttgttaa gnttatccat tataattagt tnggcaggag    420
ctaatacaaa tcacatttac ngacnagcaa taataaaact gaagtaccag ttaaatatcc    480
aaaataatta aaggaacatt tttagcctgg gtataattag ctaattcact ttacaagcat    540
ttattnagaa tgaattcaca tgttattatt ccntagccca acacaatgg                589
```

<210> SEQ ID NO 205
<211> LENGTH: 545
<212> TYPE: DNA
<213> ORGANISM: Homo sapien
<220> FEATURE:
<221> NAME/KEY: misc_feature
<222> LOCATION: (1)...(545)
<223> OTHER INFORMATION: n = A,T,C or G

<400> SEQUENCE: 205

```
tttttnttt tttttcagt aataatcaga acaatattta ttttttatatt taaaattcat       60 agaaaagtgc cttacattta ataaaagttt gtttctcaaa gtgatcagag gaattagata    120
tngtcttgaa caccaatatt aatttgagga aaatacacca aaatacatta agtaaattat    180
ttaagatcat agagcttgta agtgaaaaga taaaatttga cctcagaaac tctgagcatt    240
aaaaatccac tattagcaaa taaattacta tggacttctt gctttaattt tgtgatgaat    300
atggggtgtc actggtaaac caacacattc tgaaggatac attacttagt gatagattct    360
tatgtacttt gctanatnac gtggatatga gttgacaagt ttctctttct tcaatctttt    420 aagggggcnga ngaaatgagg aagaaaagaa aaggattacg catactgttc tttctatngg    480
aaggattaga tatgtttcct ttgccaatat taaaaaaata ataatgttta ctactagtga    540
aaccc                                                                 545
```

```
<210> SEQ ID NO 206
<211> LENGTH: 487
<212> TYPE: DNA
<213> ORGANISM: Homo sapien
<220> FEATURE:
<221> NAME/KEY: misc_feature
<222> LOCATION: (1)...(487)
<223> OTHER INFORMATION: n = A,T,C or G

<400> SEQUENCE: 206 ttttttttt  tttttagtc  aagtttctna  ttttattat   aattaaagtc  ttggtcattt    60
catttattag  ctctgcaact  tacatattta  aattaaagaa  acgttnttag  acaactgtna  120
caatttataa  atgtaaggtg  ccattattga  gtanatatat  tcctccaaga  gtggatgtgt  180
cccttctccc  accaactaat  gaancagcaa  cattagtttta  attttattag  tagatnatac  240
actgctgcaa  acgctaattc  tcttctccat  ccccatgtng  atattgtgta  tatgtgtgag  300
ttggtnagaa  tgcatcanca  atctnacaat  caacagcaag  atgaagctag  gcntgggctt  360
tcggtgaaaa  tagactgtgt  ctgtctgaat  caaatgatct  gacctatcct  cggtggcaag  420
aactcttcga  accgcttcct  caaaggcngc  tgccacattt  gtggcntctn  ttgcacttgt  480
ttcaaaa                                                                487

<210> SEQ ID NO 207
<211> LENGTH: 332
<212> TYPE: DNA
<213> ORGANISM: Homo sapien
<220> FEATURE:
<221> NAME/KEY: misc_feature
<222> LOCATION: (1)...(332)
<223> OTHER INFORMATION: n = A,T,C or G

<400> SEQUENCE: 207
tgaattggct  aaaagactgc  atttttanaa  ctagcaactc  ttatttcttt  cctttaaaaa    60
tacatagcat  taaatcccaa  atcctatta   aagacctgac  agcttgagaa  ggtcactact  120
gcatttatag  gaccttctgg  tggttctgct  gttacntttg  aantctgaca  atccttgana  180
atctttgcat  gcagaggagg  taaaaggtat  tggattttca  cagaggaana  acacagcgca  240
gaaatgaagg  ggccaggctt  actgagcttg  tccactggag  ggctcatggg  tgggacatgg  300
aaaagaaggc  agcctaggcc  ctggggagcc  ca                                  332

<210> SEQ ID NO 208
<211> LENGTH: 524
<212> TYPE: DNA
<213> ORGANISM: Homo sapien
<220> FEATURE:
<221> NAME/KEY: misc_feature
<222> LOCATION: (1)...(524)
<223> OTHER INFORMATION: n = A,T,C or G

<400> SEQUENCE: 208
agggcgtggt  gcggagggcg  ttactgtttt  gtctcagtaa  caataaatac  aaaaagactg    60
gttgtgttcc  ggccccatcc  aaccacgaag  ttgatttctc  ttgtgtgcag  agtgactgat  120
tttaaaggac  atggagcttg  tcacaatgtc  acaatgtcac  agtgtgaagg  gcacactcac  180
tcccgcgtga  ttcacattta  gcaaccaaca  atagctcatg  agtccatact  tgtaaatact  240
tttggcagaa  tacttnttga  aacttgcaga  tgataactaa  gatccaagat  atttcccaaa  300
gtaaatagaa  gtgggtcata  atattaatta  cctgttcaca  tcagcttcca  tttacaagtc  360
atgagcccag  acactgacat  caaactaagc  ccacttagac  tcctcaccac  cagtctgtcc  420
```

```
tgtcatcaga caggaggctg tcaccttgac caaattctca ccagtcaatc atctatccaa    480
aaaccattac ctgatccact tccggtaatg caccaccttg gtga                    524
```

<210> SEQ ID NO 209
<211> LENGTH: 159
<212> TYPE: DNA
<213> ORGANISM: Homo sapien

<400> SEQUENCE: 209

```
gggtgaggaa atccagagtt gccatggaga aaattccagt gtcagcattc ttgctccttg     60
tggccctctc ctacactctg gccagagata ccacagtcaa acctggagcc aaaaaggaca    120
caaaggactc tcgacccaaa ctgccccaga ccctctcca                          159
```

<210> SEQ ID NO 210
<211> LENGTH: 256
<212> TYPE: DNA
<213> ORGANISM: Homo sapien
<220> FEATURE:
<221> NAME/KEY: misc_feature
<222> LOCATION: (1)...(256)
<223> OTHER INFORMATION: n = A,T,C or G

<400> SEQUENCE: 210

```
actccctggc agacaaaggc agaggagaga gctctgttag ttctgtgttg ttgaactgcc     60
actgaatttc tttccacttg gactattaca tgccanttga gggactaatg gaaaaacgta    120
tggggagatt ttanccaatt tangtntgta aatgggagga ctggggcagg cgggagagat    180
ttgcagggtg naaatgggan ggctggtttg ttanatgaac agggacatag gaggtaggca    240
ccaggatgct aaatca                                                   256
```

<210> SEQ ID NO 211
<211> LENGTH: 264
<212> TYPE: DNA
<213> ORGANISM: Homo sapien
<220> FEATURE:
<221> NAME/KEY: misc_feature
<222> LOCATION: (1)...(264)
<223> OTHER INFORMATION: n = A,T,C or G

<400> SEQUENCE: 211

```
acattgtttt tttgagataa agcattgaga gagctctcct taacgtgaca caatggaagg     60
actggaacac atacccacat ctttgttctg agggataatt ttctgataaa gtcttgctgt    120
atattcaagc acatatgtta tatattattc agttccatgt ttatagccta gttaaggaga    180
ggggagatac attcngaaag aggactgaaa gaaatactca agtnggaaaa cagaaaaga    240 aaaaaggag caaatgagaa gcct                                           264
```

<210> SEQ ID NO 212
<211> LENGTH: 328
<212> TYPE: DNA
<213> ORGANISM: Homo sapien
<220> FEATURE:
<221> NAME/KEY: misc_feature
<222> LOCATION: (1)...(328)
<223> OTHER INFORMATION: n = A,T,C or G

<400> SEQUENCE: 212

```
acccaaaaat ccaatgctga atatttggct tcattattcc canattcttt gattgtcaaa     60
ggatttaatg ttgtctcagc ttgggcactt cagttaggac ctaaggatgc cagccggcag    120
gtttatatat gcagcaacaa tattcaagcg cgacaacagg ttattgaact gcccgccag     180
```

```
ttnaatttca ttcccattga cttgggatcc ttatcatcag ccagagagat tgaaaattta      240
cccctacnac tctttactct ctgganaggg ccagtggtgg tagctataag cttggccaca      300
tttttttttc ctttattcct tgtcaga                                          328
```

<210> SEQ ID NO 213
<211> LENGTH: 250
<212> TYPE: DNA
<213> ORGANISM: Homo sapien
<220> FEATURE:
<221> NAME/KEY: misc_feature
<222> LOCATION: (1)...(250)
<223> OTHER INFORMATION: n = A,T,C or G

<400> SEQUENCE: 213

```
acttatgagc agagcgacat atccnagtgt agactgaata aaactgaatt ctctccagtt      60
taaagcattg ctcactgaag ggatagaagt gactgccagg agggaaagta agccaaggct     120
cattatgcca aagganatat acatttcaat tctccaaact tcttcctcat tccaagagtt     180
ttcaatattt gcatgaacct gctgataanc catgttaana acaaatatc tctctnacct      240 tctcatcggt                                                            250
```

<210> SEQ ID NO 214
<211> LENGTH: 444
<212> TYPE: DNA
<213> ORGANISM: Homo sapien
<220> FEATURE:
<221> NAME/KEY: misc_feature
<222> LOCATION: (1)...(444)
<223> OTHER INFORMATION: n = A,T,C or G

<400> SEQUENCE: 214

```
acccagaatc caatgctgaa tatttggctt cattattccc agattctttg attgtcaaag      60
gatttaatgt tgtctcagct tgggcacttc agtaggacc taaggatgcc agccggcagg     120
tttatatatg cagcaacaat attcaagcgc gacaacaggt tattgaactt gcccgccagt     180
tgaatttcat tcccattgac ttgggatcct tatcatcagc canagagatt gaaaatttac     240
ccctacgact ctttactctc tggagagggc cagtggtggt agctataagc ttggccacat     300 tttttttttcc tttattcctt tgtcagagat gcgattcatc catatgctan aaaccaacag     360
agtgactttt acaaaattcc tataganatt gtgaataaaa ccttacctat agttgccatt     420
actttgctct ccctaatata cctc                                            444
```

<210> SEQ ID NO 215
<211> LENGTH: 366
<212> TYPE: DNA
<213> ORGANISM: Homo sapien
<220> FEATURE:
<221> NAME/KEY: misc_feature
<222> LOCATION: (1)...(366)
<223> OTHER INFORMATION: n = A,T,C or G

<400> SEQUENCE: 215

```
acttatgagc agagcgacat atccaagtgt anactgaata aaactgaatt ctctccagtt      60
taaagcattg ctcactgaag ggatagaagt gactgccagg agggaaagta agccaaggct     120
cattatgcca aagganatat acatttcaat tctccaaact tcttcctcat tccaagagtt     180
ttcaatattt gcatgaacct gctgataagc catgttgaga acaaatatc tctctgacct      240 tctcatcggt aagcagaggc tgtaggcaac atggaccata gcgaanaaaa aacttagtaa     300
```

```
tccaagctgt tttctacact gtaaccaggt ttccaaccaa ggtggaaatc tcctatactt    360
ggtgcc                                                               366

<210> SEQ ID NO 216
<211> LENGTH: 260
<212> TYPE: DNA
<213> ORGANISM: Homo sapien
<220> FEATURE:
<221> NAME/KEY: misc_feature
<222> LOCATION: (1)...(260)
<223> OTHER INFORMATION: n = A,T,C or G

<400> SEQUENCE: 216
ctgtataaac agaactccac tgcangaggg agggccgggc caggagaatc tccgcttgtc     60
caagacaggg gcctaaggag ggtctccaca ctgctnntaa gggctnttnc attttttat    120 taataaaaag tnnaaaaggc ctcttctcaa cttttttccc ttnggctgga aaatttaaaa   180
atcaaaaatt tcctnaagtt ntcaagctat catatatact ntatcctgaa aaagcaacat   240
aattcttcct tccctccttt                                               260

<210> SEQ ID NO 217
<211> LENGTH: 262
<212> TYPE: DNA
<213> ORGANISM: Homo sapien
<220> FEATURE:
<221> NAME/KEY: misc_feature
<222> LOCATION: (1)...(262)
<223> OTHER INFORMATION: n = A,T,C or G

<400> SEQUENCE: 217
acctacgtgg gtaagtttan aaatgttata atttcaggaa naggaacgca tataattgta    60
tcttgcctat aattttctat tttaataagg aaatagcaaa ttggggtggg gggaatgtag   120
ggcattctac agtttgagca aaatgcaatt aaatgtggaa ggacagcact gaaaaatttt   180
atgaataatc tgtatgatta tatgtctcta gagtagattt ataattagcc acttacccta   240
atatccttca tgcttgtaaa gt                                            262

<210> SEQ ID NO 218
<211> LENGTH: 205
<212> TYPE: DNA
<213> ORGANISM: Homo sapien
<220> FEATURE:
<221> NAME/KEY: misc_feature
<222> LOCATION: (1)...(205)
<223> OTHER INFORMATION: n = A,T,C or G

<400> SEQUENCE: 218
accaaggtgg tgcattaccg gaantggatc aangacacca tcgtggccaa cccctgagca    60
cccctatcaa ctcccttttg tagtaaactt ggaaccttgg aaatgaccag gccaagactc   120
aggcctcccc agttctactg acctttgtcc ttangtntna ngtccagggt tgctaggaaa   180
anaaatcagc agacacaggt gtaaa                                         205

<210> SEQ ID NO 219
<211> LENGTH: 114
<212> TYPE: DNA
<213> ORGANISM: Homo sapien

<400> SEQUENCE: 219
tactgttttg tctcagtaac aataaataca aaaagactgg ttgtgttccg gccccatcca    60
accacgaagt tgatttctct tgtgtgcaga gtgactgatt ttaaaggaca tgga          114
```

<210> SEQ ID NO 220
<211> LENGTH: 93
<212> TYPE: DNA
<213> ORGANISM: Homo sapien

<400> SEQUENCE: 220
actagccagc acaaaaggca gggtagcctg aattgctttc tgctctttac atttctttta     60
aaataagcat ttagtgctca gtccctactg agt                                  93

<210> SEQ ID NO 221
<211> LENGTH: 167
<212> TYPE: DNA
<213> ORGANISM: Homo sapien
<220> FEATURE:
<221> NAME/KEY: misc_feature
<222> LOCATION: (1)...(167)
<223> OTHER INFORMATION: n = A,T,C or G

<400> SEQUENCE: 221
actangtgca ggtgcgcaca aatatttgtc gatattccct tcatcttgga ttccatgagg     60
tcttttgccc agcctgtggc tctactgtag taagtttctg ctgatgagga gccagnatgc    120
cccccactac cttccctgac gctccccana aatcacccaa cctctgt                  167

<210> SEQ ID NO 222
<211> LENGTH: 351
<212> TYPE: DNA
<213> ORGANISM: Homo sapien

<400> SEQUENCE: 222
agggcgtggt gcggagggcg gtactgacct cattagtagg aggatgcatt ctggcacccc     60
gttcttcacc tgtccccaa tccttaaaag gccatactgc ataaagtcaa caacagataa    120
atgtttgctg aattaaagga tggatgaaaa aaattaataa tgaattttg cataatccaa    180 ttttctcttt tatatttcta gaagaagttt ctttgagcct attagatccc gggaatcttt    240
taggtgagca tgattagaga gcttgtaggt tgcttttaca tatatctggc atatttgagt    300
ctcgtatcaa acaatagat tggtaaaggt ggtattattg tattgataag t              351

<210> SEQ ID NO 223
<211> LENGTH: 383
<212> TYPE: DNA
<213> ORGANISM: Homo sapien
<220> FEATURE:
<221> NAME/KEY: misc_feature
<222> LOCATION: (1)...(383)
<223> OTHER INFORMATION: n = A,T,C or G

<400> SEQUENCE: 223
aaaacaaaca aacaaaaaaa acaattcttc attcagaaaa attatcttag ggactgatat     60
tggtaattat ggtcaattta atwrtrttkt ggggcatttc cttacattgt cttgacaaga    120
ttaaaatgtc tgtgccaaaa ttttgtattt tatttggaga cttcttatca aaagtaatgc    180
tgccaaagga agtctaagga attagtagtg ttcccmtcac ttgtttggag tgtgctattc    240
taaaagattt tgatttcctg gaatgacaat tatattttaa ctttggtggg ggaaanagtt    300
ataggaccac agtcttcact tctgatactt gtaaattaat cttttattgc acttgttttg    360
accattaagc tatatgttta aaa                                            383

<210> SEQ ID NO 224
<211> LENGTH: 320
<212> TYPE: DNA
<213> ORGANISM: Homo sapien

<400> SEQUENCE: 224

| | | | | | |
|---|---|---|---|---|---|
| cccctgaagg | cttcttgtta | gaaaatagta | cagttacaac | caataggaac | aacaaaaaga | 60 |
| aaaagtttgt | gacattgtag | tagggagtgt | gtacccctta | ctccccatca | aaaaaaaat | 120 |
| ggatacatgg | ttaaaggata | raagggcaat | attttatcat | atgttctaaa | agagaaggaa | 180 |
| gagaaaatac | tactttctcr | aaatggaagc | ccttaaaggt | gctttgatac | tgaaggacac | 240 |
| aaatgtggcc | gtccatcctc | ctttaragtt | gcatgacttg | gacacggtaa | ctgttgcagt | 300 |
| tttaractcm | gcattgtgac | | | | | 320 |

<210> SEQ ID NO 225
<211> LENGTH: 1214
<212> TYPE: DNA
<213> ORGANISM: Homo sapien

<400> SEQUENCE: 225

| | | | | | |
|---|---|---|---|---|---|
| gaggactgca | gcccgcactc | gcagccctgg | caggcggcac | tggtcatgga | aaacgaattg | 60 |
| ttctgctcgg | gcgtcctggt | gcatccgcag | tgggtgctgt | cagccgcaca | ctgtttccag | 120 |
| aactcctaca | ccatcgggct | gggcctgcac | agtcttgagg | ccgaccaaga | gccagggagc | 180 |
| cagatggtgg | aggccagcct | ctccgtacgg | cacccagagt | acaacagacc | cttgctcgct | 240 |
| aacgacctca | tgctcatcaa | gttggacgaa | tccgtgtccg | agtctgacac | catccggagc | 300 |
| atcagcattg | cttcgcagtg | ccctaccgcg | gggaactctt | gcctcgtttc | tggctggggt | 360 |
| ctgctggcga | acgcagaat | gcctaccgtg | ctgcagtgcg | tgaacgtgtc | ggtggtgtct | 420 |
| gaggaggtct | gcagtaagct | ctatgacccg | ctgtaccacc | ccagcatgtt | ctgcgccggc | 480 |
| ggagggcaag | accagaagga | ctcctgcaac | ggtgactctg | gggggcccct | gatctgcaac | 540 |
| gggtacttgc | agggccttgt | gtctttcgga | aaagcccgt | gtggccaagt | tggcgtgcca | 600 |
| ggtgtctaca | ccaacctctg | caaattcact | gagtggatag | agaaaaccgt | ccaggccagt | 660 |
| taactctggg | gactgggaac | ccatgaaatt | gaccccaaa | tacatcctgc | ggaaggaatt | 720 |
| caggaatatc | tgttcccagc | ccctcctccc | tcaggcccag | gagtccaggc | ccccagcccc | 780 |
| tcctccctca | aaccaagggt | acagatcccc | agccctcct | ccctcagacc | caggagtcca | 840 |
| gacccccag | cccctcctcc | ctcagaccca | ggagtccagc | ccctcctccc | tcagacccag | 900 |
| gagtccagac | ccccagccc | ctcctccctc | agacccaggg | gtccaggccc | ccaacccctc | 960 |
| ctccctcaga | ctcagaggtc | caagccccca | accctccctt | cccagaccc | agaggtccag | 1020 |
| gtcccagccc | ctcctccctc | agacccagcg | gtccaatgcc | acctagactc | tccctgtaca | 1080 |
| cagtgccccc | ttgtggcacg | ttgacccaac | cttaccagtt | ggttttcat | tttttgtccc | 1140 |
| tttccctag | atccagaaat | aaagtctaag | agaagcgcaa | aaaaaaaaa | aaaaaaaaa | 1200 |
| aaaaaaaaaa | aaaa | | | | | 1214 |

<210> SEQ ID NO 226
<211> LENGTH: 119
<212> TYPE: DNA
<213> ORGANISM: Homo sapien

<400> SEQUENCE: 226

| | | | | | |
|---|---|---|---|---|---|
| acccagtatg | tgcagggaga | cggaaccccca | tgtgacagcc | cactccacca | gggttcccaa | 60 |
| agaacctggc | ccagtcataa | tcattcatcc | tgacagtggc | aataatcacg | ataaccagt | 119 |

<210> SEQ ID NO 227
<211> LENGTH: 818
<212> TYPE: DNA
<213> ORGANISM: Homo sapien

<400> SEQUENCE: 227

| | | | | | |
|---|---|---|---|---|---|
| acaattcata | gggacgacca | atgaggacag | ggaatgaacc | cggctctccc | ccagccctga | 60 |
| tttttgctac | atatggggtc | ccttttcatt | ctttgcaaaa | acactgggtt | ttctgagaac | 120 |
| acggacggtt | cttagcacaa | tttgtgaaat | ctgtgtaraa | ccgggctttg | caggggagat | 180 |
| aattttcctc | ctctggagga | aaggtggtga | ttgacaggca | gggagacagt | gacaaggcta | 240 |
| gagaaagcca | cgctcggcct | tctctgaacc | aggatgaac | ggcagacccc | tgaaaacgaa | 300 |
| gcttgtcccc | ttccaatcag | ccacttctga | gaacccccat | ctaacttcct | actggaaaag | 360 |
| agggcctcct | caggagcagt | ccaagagttt | tcaaagataa | cgtgacaact | accatctaga | 420 |
| ggaaagggtg | caccctcagc | agagaagccg | agagcttaac | tctggtcgtt | tccagagaca | 480 |
| acctgctggc | tgtcttggga | tgcgcccagc | ctttgagagg | ccactacccc | atgaacttct | 540 |
| gccatccact | ggacatgaag | ctgaggacac | tgggcttcaa | cactgagttg | tcatgagagg | 600 |
| gacaggctct | gccctcaagc | cggctgaggg | cagcaaccac | tctcctcccc | tttctcacgc | 660 |
| aaagccattc | ccacaaatcc | agaccatacc | atgaagcaac | gagacccaaa | cagtttggct | 720 |
| caagaggata | tgaggactgt | ctcagcctgg | ctttgggctg | acaccatgca | cacacacaag | 780 |
| gtccacttct | aggttttcag | cctagatggg | agtcgtgt | | | 818 |

<210> SEQ ID NO 228
<211> LENGTH: 744
<212> TYPE: DNA
<213> ORGANISM: Homo sapien

<400> SEQUENCE: 228

| | | | | | |
|---|---|---|---|---|---|
| actggagaca | ctgttgaact | tgatcaagac | ccagaccacc | ccaggtctcc | ttcgtgggat | 60 |
| gtcatgacgt | ttgacatacc | tttggaacga | gcctcctcct | tggaagatgg | aagaccgtgt | 120 |
| tcgtggccga | cctggcctct | cctggcctgt | ttcttaagat | gcggagtcac | atttcaatgg | 180 |
| taggaaaagt | ggcttcgtaa | aatagaagag | cagtcactgt | ggaactacca | aatggcgaga | 240 |
| tgctcggtgc | acattgggt | gctttgggat | aaaagattta | tgagccaact | attctctggc | 300 |
| accagattct | aggccagttt | gttccactga | agcttttccc | acagcagtcc | acctctgcag | 360 |
| gctggcagct | gaatggcttg | ccggtggctc | tgtggcaaga | tcacactgag | atcgatgggt | 420 |
| gagaaggcta | ggatgcttgt | ctagtgttct | tagctgtcac | gttggctcct | tccaggttgg | 480 |
| ccagacggtg | ttggccactc | ccttctaaaa | cacaggcgcc | ctcctggtga | cagtgacccg | 540 |
| ccgtggtatg | ccttggccca | ttccagcagt | cccagttatg | catttcaagt | ttggggtttg | 600 |
| ttcttttcgt | taatgttcct | ctgtgttgtc | agctgtcttc | atttcctggg | ctaagcagca | 660 |
| ttgggagatg | tggaccagag | atccactcct | taagaaccag | tggcgaaaga | cactttcttt | 720 |
| cttcactctg | aagtagctgg | tggt | | | | 744 |

COMPOUNDS FOR IMMUNODIAGNOSIS OF PROSTATE CANCER AND METHODS FOR THEIR USE

REFERENCE TO RELATED APPLICATIONS

This application is a continuation-in-part of U.S. patent application Ser. No. 09/030,606, filed Feb. 25, 1998, now U.S. Pat. No. 6,887,660, which is a continuation-in-part of U.S. patent application Ser. No. 09/020,747, filed Feb. 9, 1998, now abandoned, which is a continuation-in-part of U.S. patent application Ser. No. 08/904,809, filed Aug. 1, 1997, now abandoned, which is a continuation-in-part of U.S. patent application Ser. No. 08/806,596, filed Feb. 25, 1997, now abandoned.

TECHNICAL FIELD

The present invention relates generally to the treatment and monitoring of prostate cancer. The invention is more particularly related to polypeptides comprising at least a portion of a prostate protein. Such polypeptides may be used for the production of compounds, such as antibodies, useful for diagnosing and monitoring the progression of prostate cancer, and possibly other tumor types, in a patient.

BACKGROUND OF THE INVENTION

Prostate cancer is the most common form of cancer among males, with an estimated incidence of 30% in men over the age of 50. Overwhelming clinical evidence shows that human prostate cancer has the propensity to metastasize to bone, and the disease appears to progress inevitably from androgen dependent to androgen refractory status, leading to increased patient mortality. This prevalent disease is currently the second leading cause of cancer death among men in the U.S.

In spite of considerable research into diagnosis and therapy of the disease, prostate cancer remains difficult to detect and to treat. Commonly, treatment is based on surgery and/or radiation therapy, but these methods are ineffective in a significant percentage of cases. Two previously identified prostate specific proteins—prostate specific antigen (PSA) and prostatic acid phosphatase (PAP)— have limited diagnostic and therapeutic potential. For example, PSA levels do not always correlate well with the presence of prostate cancer, being positive in a percentage of non-prostate cancer cases, including benign prostatic hyperplasia (BPH). Furthermore, PSA measurements correlate with prostate volume, and do not indicate the level of metastasis.

Accordingly, there remains a need in the art for improved and diagnostic methods for prostate cancer.

SUMMARY OF THE INVENTION

The present invention provides methods for immunodiagnosis of prostate cancer, together with kits for use in such methods. Polypeptides are disclosed which comprise at least an immunogenic portion of a prostate tumor protein or a variant of said protein that differs only in conservative substitutions and/or modifications, wherein the prostate tumor protein comprises an amino acid sequence encoded by a DNA molecule having a sequence selected from the group consisting of nucleotide sequences recited in SEQ ID NOS: 2–3, 5–107, 109–11, 115–171, 173–175, 177, 179–228 and sequences that hybridize to a nucleotide sequence provided in SEQ ID NOS: 2–3, 5–107, 109–11, 115–171, 173–175, 177 or 179–228 under moderately stringent conditions. Such polypeptides may be usefully employed in the diagnosis and monitoring of prostate cancer.

In one specific aspect of the present invention, methods are provided for detecting prostate cancer in a patient, comprising: (a) contacting a biological sample obtained from a patient with a binding agent that is capable of binding to one of the above polypeptides; and (b) detecting in the sample a protein or polypeptide that binds to the binding agent. In preferred embodiments, the binding agent is an antibody, most preferably a monoclonal antibody.

In related aspects, methods are provided for monitoring the progression of prostate cancer in a patient, comprising: (a) contacting a biological sample obtained from a patient with a binding agent that is capable of binding to one of the above polypeptides; (b) determining in the sample an amount of a protein or polypeptide that binds to the binding agent; (c) repeating steps (a) and (b); and comparing the amounts of polypeptide detected in steps (b) and (c).

Within related aspects, the present invention provides antibodies, preferably monoclonal antibodies, that bind to the inventive polypeptides, as well as diagnostic kits comprising such antibodies, and methods of using such antibodies to inhibit the development of prostate cancer.

The present invention further provides methods for detecting prostate cancer comprising: (a) obtaining a biological sample from a patient; (b) contacting the sample with a first and a second oligonucleotide primer in a polymerase chain reaction, at least one of the oligonucleotide primers being specific for a DNA molecule that encodes one of the above polypeptides; and (c) detecting in the sample a DNA sequence that amplifies in the presence of the first and second oligonucleotide primers. In a preferred embodiment, at least one of the oligonucleotide primers comprises at least about 10 contiguous nucleotides of a DNA molecule having a partial sequence selected from the group consisting of SEQ ID NOS: 2–3, 5–107, 109–11, 115–171, 173–175, 177 and 179–228.

In a further aspect, the present invention provides a method for detecting prostate cancer in a patient comprising: (a) obtaining a biological sample from the patient; (b) contacting the sample with an oligonucleotide probe specific for a DNA molecule that encodes one of the above polypeptides; and (c) detecting in the sample a DNA sequence that hybridizes to the oligonucleotide probe. Preferably, the oligonucleotide probe comprises at least about 15 contiguous nucleotides of a DNA molecule having a partial sequence selected from the group consisting of SEQ ID NOS: 2–3, 5–107, 109–11, 115–171, 173–175, 177 and 179–228.

In related aspects, diagnostic kits comprising the above oligonucleotide probes or primers are provided.

These and other aspects of the present invention will become apparent upon reference to the following detailed description and attached drawings. All references disclosed herein are hereby incorporated by reference in their entirety as if each was incorporated individually.

DETAILED DESCRIPTION OF THE INVENTION

As noted above, the present invention is generally directed to compositions and methods for the immunodiagnosis and monitoring of prostate cancer. The inventive compositions are generally polypeptides that comprise at least a portion of a prostate tumor protein. Also included within the present invention are molecules (such as an antibody or fragment thereof) that bind to the inventive polypeptides. Such molecules are referred to herein as "binding agents."

In particular, the subject invention discloses polypeptides comprising at least a portion of a human prostate tumor protein, or a variant thereof such a protein, wherein the prostate tumor protein includes an amino acid sequence encoded by a DNA molecule having a sequence selected from the group consisting of nucleotide sequences recited in SEQ ID Nos: 2–3, 5–107, 109–11, 115–171, 173–175, 177, 179–228, the complements of said nucleotide sequences and variants thereof. As used herein, the term "polypeptide" encompasses amino acid chains of any length, including full length proteins, wherein the amino acid residues are linked by covalent peptide bonds. Thus, a polypeptide comprising a portion of one of the above prostate proteins may consist entirely of the portion, or the portion may be present within a larger polypeptide that contains additional sequences. The additional sequences may be derived from the native protein or may be heterologous, and such sequences may be immunoreactive and/or antigenic.

As used herein, an "immunogenic portion" of a human prostate tumor protein is a portion that is capable of eliciting an immune response in a patient inflicted with prostate cancer and as such binds to antibodies present within sera from a prostate cancer patient. Such immunogenic portions generally comprise at least about 5 amino acid residues, more preferably at least about 10, and most preferably at least about 20 amino acid residues. Immunogenic portions of the proteins described herein may thus be identified in antibody binding assays. Such assays may generally be performed using any of a variety of means known to those of ordinary skill in the art, as described, for example, in Harlow and Lane, *Antibodies: A Laboratory Manual*, Cold Spring Harbor Laboratory, Cold Spring Harbor, N.Y., 1988. For example, a polypeptide may be immobilized on a solid support (as described below) and contacted with patient sera to allow binding of antibodies within the sera to the immobilized polypeptide. Unbound sera may then be removed and bound antibodies detected using, for example, $^{125}$I-labeled Protein A. Alternatively, a polypeptide may be used to generate monoclonal and polyclonal antibodies for use in detection of the polypeptide in blood or other fluids of prostate cancer patients. Methods for preparing and identifying immunogenic portions of antigens of known sequence are well known in the art and include those summarized in Paul, *Fundamental Immunology*, 3$^{rd}$ ed., Raven Press, 1993, pp. 243–247.

The compositions and methods of the present invention also encompass variants of the above polypeptides and DNA molecules. A polypeptide "variant," as used herein, is a polypeptide that differs from the recited polypeptide only in conservative substitutions and/or modifications, such that the therapeutic, antigenic and/or immunogenic properties of the polypeptide are retained. Polypeptide variants preferably exhibit at least about 70%, more preferably at least about 90% and most preferably at least about 95% identity to the identified polypeptides. The identity of polypeptides may be determined by comparing sequences using computer algorithms well known to those of skill in the art, such as Megalign, using default parameters. For prostate tumor polypeptides with immunoreactive properties, variants may, alternatively, be identified by modifying the amino acid sequence of one of the above polypeptides, and evaluating the immunoreactivity of the modified polypeptide. For prostate tumor polypeptides useful for the generation of diagnostic binding agents, a variant may be identified by evaluating a modified polypeptide for the ability to generate antibodies that detect the presence or absence of prostate cancer. Such modified sequences may be prepared and tested using, for example, the representative procedures described herein.

As used herein, a "conservative substitution" is one in which an amino acid is substituted for another amino acid that has similar properties, such that one skilled in the art of peptide chemistry would expect the secondary structure and hydropathic nature of the polypeptide to be substantially unchanged. In general, the following groups of amino acids represent conservative changes: (1) ala, pro, gly, glu, asp, gin, asn, ser, thr; (2) cys, ser, tyr, thr; (3) val, ile, leu, met, ala, phe; (4) lys, arg, his; and (5) phe, tyr, trp, his.

Variants may also, or alternatively, contain other modifications, including the deletion or addition of amino acids that have minimal influence on the antigenic properties, secondary structure and hydropathic nature of the polypeptide. For example, a polypeptide may be conjugated to a signal (or leader) sequence at the N-terminal end of the protein which co-translationally or post-translationally directs transfer of the protein. The polypeptide may also be conjugated to a linker or other sequence for ease of synthesis, purification or identification of the polypeptide (e.g., poly-His), or to enhance binding of the polypeptide to a solid support. For example, a polypeptide may be conjugated to an immunoglobulin Fc region.

A nucleotide "variant" is a sequence that differs from the recited nucleotide sequence in having one or more nucleotide deletions, substitutions or additions. Such modifications may be readily introduced using standard mutagenesis techniques, such as oligonucleotide-directed site-specific mutagenesis as taught, for example, by Adelman et al. (*DNA*, 2:183, 1983). Nucleotide variants may be naturally occurring allelic variants, or non-naturally occurring variants. Variant nucleotide sequences preferably exhibit at least about 70%, more preferably at least about 80% and most preferably at least about 90% identity to the recited sequence. The identity of nucleotide sequences may be determined by comparing sequences using computer algorithms well known to those of skill in the art, such as Megalign, using default parameters. Such variant nucleotide sequences will generally hybridize to the recite nucleotide sequence under moderately stringent conditions. As used herein, "moderately stringent conditions" refers to prewashing in a solution of 6× SSC, 0.2% SDS; hybridizing at 65° C., 6× SSC, 0.2% SDS overnight; followed by two washes of 30 minutes each in 1× SSC, 0.1% SDS at 65° C. and two washes of 30 minutes each in 0.2× SSC, 0.1% SDS at 65° C.

"Polypeptides" as used herein also include combination, or fusion, polypeptides. A "combination polypeptide" is a polypeptide comprising at least one of the above immunogenic portions and one or more additional immunogenic prostate tumor-specific sequences, which are joined via a peptide linkage into a single amino acid chain. The sequences may be joined directly (i.e., with no intervening amino acids) or may be joined by way of a linked sequence (e.g., Gly-Cys-Gly) that does not significantly diminish the immunogenic properties of the component polypeptides.

The prostate tumor proteins of the present invention, and DNA molecules encoding such proteins, may be isolated from prostate tumor tissue using any of a variety of methods well known in the art. DNA sequences corresponding to a gene (of a portion thereof) encoding one of the inventive prostate tumor proteins may be isolated from a prostate tumor cDNA library using a subtraction technique as described in detail below. Examples of such DNA sequences are provided in SEQ ID Nos: 1–107, 109–111, 115–171, 173–175, 177 and 179–228. Partial DNA sequences thus obtained may be used to design oligonucleotide primers for the amplification of full-length DNA sequences in a polymerase chain reaction (PCR), using techniques well known in the art (see, for example, Mullis et al., *Cold Spring Harbor Symp. Quant. Biol.,* 51:263, 1987; Erlich ed., *PCR Technology,* Stockton Press, NY, 1989). Once a DNA sequence encoding a polypeptide is obtained, any of the above modifications may be readily introduced using standard mutagenesis techniques, such as oligonucleotide-directed site-specific mutagenesis as taught, for example, by Adelman et al. (*DNA,.* 2:183, 1983).

The prostate tumor polypeptides disclosed herein may also be generated by synthetic or recombinant means. Synthetic polypeptides having fewer than about 100 amino acids, and generally fewer than about 50 amino acids, may be generated using techniques well known to those of ordinary skill in the art. For example, such polypeptides may be synthesized using any of the commercially available solid-phase techniques, such as the Merrifield solid-phase synthesis method, where amino acids are sequentially added to a growing amino acid chain (see, for example, Merrifield, *J. Am. Chem. Soc.* 85:2149–2146, 1963). Equipment for automated synthesis of polypeptides is commercially available from suppliers such as Perkin Elmer/Applied BioSystems Division (Foster City, Calif.), and may be operated according to the manufacturer's instructions.

Alternatively, any of the above polypeptides may be produced recombinantly by inserting a DNA sequence that encodes the polypeptide into an expression vector and expressing the protein in an appropriate host. Any of a variety of expression vectors known to those of ordinary skill in the art may be employed to express recombinant polypeptides of this invention. Expression may be achieved in any appropriate host cell that has been transformed or transfected with an expression vector containing a DNA molecule that encodes a recombinant polypeptide. Suitable host cells include prokaryotes, yeast and higher eukaryotic cells. Preferably, the host cells employed are *E. coli,* yeast or a mammalian cell line, such as CHO cells. The DNA sequences expressed, in this manner may encode naturally occurring polypeptides, portions of naturally occurring polypeptides, or other variants thereof.

In general, regardless of the method of preparation, the polypeptides disclosed herein are prepared in an isolated, substantially pure form (i.e., the polypeptides are homogenous as determined by amino acid composition and primary sequence analysis). Preferably, the polypeptides are at least about 90% pure, more preferably at least about 95% pure and most preferably at least about 99% pure. In certain embodiments, described in more detail below, the substantially pure polypeptides are incorporated into pharmaceutical compositions or vaccines for use in one or more of the methods disclosed herein.

In a related aspect, the present invention provides fusion proteins comprising a first and a second inventive polypeptide or, alternatively, a polypeptide of the present invention and a known prostate antigen, together with variants of such fusion proteins. The fusion proteins of the present invention may also include a linker peptide between the first and second polypeptides.

A DNA sequence encoding a fusion protein of the present invention is constructed using known recombinant DNA techniques to assemble separate DNA sequences encoding the first and second polypeptides into an appropriate expression vector. The 3' end of a DNA sequence encoding the first polypeptide is ligated, with or without a peptide linker, to the 5' end of a DNA sequence encoding the second polypeptide so that the reading frames of the sequences are in phase to permit mRNA translation of the two DNA sequences into a single fusion protein that retains the biological activity of both the first and the second polypeptides.

A peptide linker sequence may be employed to separate the first and the second polypeptides by a distance sufficient to ensure that each polypeptide folds into its secondary and tertiary structures. Such a peptide linker sequence is incorporated into the fusion protein using standard techniques well known in the art. Suitable peptide linker sequences may be chosen based on the following factors: (1) their ability to adopt a flexible extended conformation; (2) their inability to adopt a secondary structure that could interact with functional epitopes on the first and second polypeptides; and (3) the lack of hydrophobic or charged residues that might react with the polypeptide functional epitopes. Preferred peptide linker sequences contain Gly, Asn and Ser residues. Other near neutral amino acids, such as Thr and Ala may also be used in the linker sequence. Amino acid sequences which may be usefully employed as linkers include those disclosed in Maratea et al., *Gene* 40:39–46, 1985; Murphy et al., *Proc. Natl. Acad. Sci. USA* 83:8258–8262, 1986; U.S. Pat. No. 4,935,233 and U.S. Pat. No. 4,751,180. The linker sequence may be from 1 to about 50 amino acids in length. Peptide sequences are not required when the first and second polypeptides have non-essential N-terminal amino acid regions that can be used to separate the functional domains and prevent steric interference.

The ligated DNA sequences are operably linked to suitable transcriptional or translational regulatory elements. The regulatory elements responsible for expression of DNA are located only 5' to the DNA sequence encoding the first polypeptides. Similarly, stop codons require to end translation and transcription termination signals are only present 3' to the DNA sequence encoding the second polypeptide.

Fusion proteins are also provided that comprise a polypeptide of the present invention together with an unrelated immunogenic protein. Preferably the immunogenic protein is capable of eliciting a recall response. Examples of such proteins include tetanus, tuberculosis and hepatitis proteins (see, for example, Stoute et al. *New Engl. J. Med.,* 336:86–91 (1997)).

Polypeptides and/or fusion proteins of the present invention may be used to generate binding agents, such as antibodies or fragments thereof, that are capable of detecting metastatic human prostate tumors. Binding agents of the present invention may generally be prepared using methods known to those of ordinary skill in the art, including the representative procedures described herein. Binding agents are capable of differentiating between patients with and without prostate cancer, using the representative assays described herein. In other words, antibodies or other binding agents raised against a prostate tumor protein, or a suitable portion thereof, will generate a signal indicating the presence of primary or metastatic prostate cancer in at least about 20% of patients afflicted with the disease, and will generate a negative signal indicating the absence of the disease in at least about 90% of individuals without primary or metastatic prostate cancer. Suitable portions of such prostate tumor proteins are portions that are able to generate a binding agent that indicates the presence of primary or metastatic prostate cancer in substantially all (i.e., at least about 80%, and preferably at least about 90%) of the patients for which prostate cancer would be indicated using the full length protein, and that indicate the absence of prostate cancer in substantially all of those samples that would be negative when tested with full length protein. The representative assays described below, such as the two-antibody sandwich assay, may generally be employed for evaluating the ability of a binding agent to detect metastatic human prostate tumors.

The ability of a polypeptide and/or fusion protein prepared as described herein to generate antibodies capable of detecting primary or metastatic human prostate tumors may generally be evaluated by raising one or more antibodies against the polypeptide (using, for example, a representative method described herein) and determining the ability of such antibodies to detect such tumors in patients. This determination may be made by assaying biological samples from patients with and without primary or metastatic prostate cancer for the presence of a polypeptide that binds to the generated antibodies. Such test assays may be performed, for example, using a representative procedure described below. Polypeptides that generate antibodies capable of detecting at least 20% of primary or metastatic prostate tumors by such procedures are considered to be useful in assays for detecting primary or metastatic human prostate tumors. Polypeptide specific antibodies may be used alone or in combination to improve sensitivity.

Polypeptides and/or fusion proteins capable of detecting primary or metastatic human prostate tumors may be used as markers for diagnosing prostate cancer or for monitoring disease progression in patients. In one embodiment, prostate cancer in a patient may be diagnosed by evaluating a biological sample obtained from the patient for the level of one or more of the above polypeptides, relative to a predetermined cut-off value. As used herein, suitable "biological samples" include blood, sera, urine and/or prostate secretions.

The level of one or more of the above polypeptides may be evaluated using any binding agent specific for the polypeptide(s). A "binding agent," in the context of this invention, is any agent (such as a compound or a cell) that binds to a polypeptide as described above. As used herein, "binding" refers to a noncovalent association between two separate molecules (each of which may be free (i.e., in solution) or present on the surface of a cell or a solid support), such that a "complex" is formed. Such a complex may be free or immobilized (either covalently or noncovalently) on a support material. The ability to bind may generally be evaluated by determining a binding constant for the formation of the complex. The binding constant is the value obtained when the concentration of the complex is divided by the product of the component concentrations. In general, two compounds are said to "bind" in the context of the present invention when the binding constant for complex formation exceeds about $10^3$ L/mol. The binding constant may be determined using methods well known to those of ordinary skill in the art.

Any agent that satisfies the above requirements may be a binding agent. For example, a binding agent may be a ribosome with or without a peptide component, an RNA molecule or a peptide. In a preferred embodiment, the binding partner is an antibody, or a fragment thereof. Such antibodies may be polyclonal, or monoclonal. In addition, the antibodies may be single chain, chimeric, CDR-grafted or humanized. Antibodies may be prepared by the methods described herein and by other methods well known to those of skill in the art.

There are a variety of assay formats known to those of ordinary skill in the art for using a binding partner to detect polypeptide markers in a sample. See, e.g., Harlow and Lane, *Antibodies. A Laboratory Manual*, Cold Spring Harbor Laboratory, 1988. In a preferred embodiment, the assay involves the use of binding partner immobilized on a solid support to bind to and remove the polypeptide from the remainder of the sample. The bound polypeptide may then be detected using a second binding partner that contains a reporter group. Suitable second binding partners include antibodies that bind to the binding partner/polypeptide complex. Alternatively, a competitive assay may be utilized, in which a polypeptide is labeled with a reporter group and allowed to bind to the immobilized binding partner after incubation of the binding partner with the sample. The extent to which components of the sample inhibit the binding of the labeled polypeptide to the binding partner is indicative of the reactivity of the sample with the immobilized binding partner.

The solid support may be any material known to those of ordinary skill in the art to which the antigen may be attached. For example, the solid support may be a test well in a microtiter plate or a nitrocellulose or other suitable membrane. Alternatively, the support may be a bead or disc, such as glass, fiberglass, latex or a plastic material such as polystyrene or polyvinylchloride. The support may also be a magnetic particle or a fiber optic sensor, such as those disclosed, for example, in U.S. Pat. No. 5,359,681. The binding agent may be immobilized on the solid support using a variety of techniques known to those of skill in the art, which are amply described in the patent and scientific literature. In the context of the present invention, the term "immobilization" refers to both noncovalent association, such as adsorption, and covalent attachment (which may be a direct linkage between the antigen and functional groups on the support or may be a linkage by way of a cross-linking agent). Immobilization by adsorption to a well in a microtiter plate or to a membrane is preferred. In such cases, adsorption may be achieved by contacting the binding agent, in a suitable buffer, with the solid support for a suitable amount of time. The contact time varies with temperature, but is typically between about 1 hour and about 1 day. In general, contacting a well of a plastic microtiter plate (such as polystyrene or polyvinylchloride) with an amount of binding agent ranging from about 10 ng to about 10 μg, and preferably about 100 ng to about 1 μg, is sufficient to immobilize an adequate amount of binding agent.

Covalent attachment of binding agent to a solid support may generally be achieved by first reacting the support with a bifunctional reagent that will react with both the support and a functional group, such as a hydroxyl or amino group, on the binding agent. For example; the binding agent may be covalently attached to supports having an appropriate polymer coating using benzoquinone or by condensation of an aldehyde group on the support with an amine and an active hydrogen on the binding partner (see, e.g., Pierce Immunotechnology Catalog and Handbook, 1991, at A12–A13).

In certain embodiments, the assay is a two-antibody sandwich assay. This assay may be performed by first contacting an antibody that has been immobilized on a solid support, commonly the well of a microtiter plate, with the sample, such that polypeptides within the sample are allowed to bind to the immobilized antibody. Unbound sample is then removed from the immobilized polypeptide-antibody complexes and a second antibody (containing a reporter group) capable of binding to a different site on the polypeptide is added. The amount of second antibody that remains bound to the solid support is then determined using a method appropriate for the specific reporter group.

More specifically, once the antibody is immobilized on the support as described above, the remaining protein binding sites on the support are typically blocked. Any suitable blocking agent known to those of ordinary skill in the art, such as bovine serum albumin or Tween 20™ (Sigma Chemical Co., St. Louis, Mo.). The immobilized antibody is then incubated with the sample, and polypeptide is allowed to bind to the antibody. The sample may be diluted with a suitable diluent, such as phosphate-buffered saline (PBS) prior to incubation. In general, an appropriate contact time (i.e., incubation time) is that period of time that is sufficient to detect the presence of polypeptide within a sample obtained from an individual with prostate cancer. Preferably, the contact time is sufficient to achieve a level of binding that is at least about 95% of that achieved at equilibrium between bound and unbound polypeptide. Those of ordinary skill in the art will recognize that the time necessary to achieve equilibrium may be readily determined by assaying the level of binding that occurs over a period of time. At room temperature, an incubation time of about 30 minutes is generally sufficient.

Unbound sample may then be removed by washing the solid support with an appropriate buffer, such as PBS containing 0.1% Tween 20™. The second antibody, which contains a reporter group, may then be added to the solid support. Preferred reporter groups include enzymes (such as horseradish peroxidase), substrates, cofactors, inhibitors, dyes, radionuclides, luminescent groups, fluorescent groups and biotin. The conjugation of antibody to reporter group may be achieved using standard methods known to those of ordinary skill in the art.

The second antibody is then incubated with the immobilized antibody-polypeptide complex for an amount of time sufficient to detect the bound polypeptide. An appropriate amount of time may generally be determined by assaying the level of binding that occurs over a period of time. Unbound second antibody is then removed and bound second antibody is detected using the reporter group. The method employed for detecting the reporter group depends upon the nature of the reporter group. For radioactive groups, scintillation counting or autoradiographic methods are generally appropriate. Spectroscopic methods may be used to detect dyes, luminescent groups and fluorescent groups. Biotin may be detected using avidin, coupled to a different reporter group (commonly a radioactive or fluorescent group or an enzyme). Enzyme reporter groups may generally be detected by the addition of substrate (generally for a specific period of time), followed by spectroscopic or other analysis of the reaction products.

To determine the presence or absence of prostate cancer, the signal detected from the reporter group that remains bound to the solid support is generally compared to a signal that corresponds to a predetermined cut-off value. In one preferred embodiment, the cut-off value is the average mean signal obtained when the immobilized antibody is incubated with samples from patients without prostate cancer. In general, a sample generating a signal that is three standard deviations above the predetermined cut-off value is considered positive for prostate cancer. In an alternate preferred embodiment, the cut-off value is determined using a Receiver. Operator Curve, according to the method of Sackett et al., *Clinical Epidemiology: A Basic Science for Clinical Medicine*, Little Brown and Co., 1985, p. 106–7. Briefly, in this embodiment, the cut-off value may be determined from a plot of pairs of true positive rates (i.e., sensitivity) and false positive rates (100%-specificity) that correspond to each possible cut-off value for the diagnostic test result. The cut-off value on the plot that is the closest to the upper left-hand corner (i.e., the value that encloses the largest area) is the most accurate cut-off value, and a sample generating a signal that is higher than the cut-off value determined by this method may be considered positive. Alternatively, the cut-off value may be shifted to the left along the plot, to minimize the false positive rate, or to the right, to minimize the false negative rate. In general, a sample generating a signal that is higher than the cut-off value determined by this method is considered positive for prostate cancer.

In a related embodiment, the assay is performed in a flow-through or strip test format, wherein the antibody is immobilized on a membrane, such as nitrocellulose. In the flow-through test, polypeptides within the sample bind to the immobilized antibody as the sample passes through the membrane. A second, labeled antibody then binds to the antibody-polypeptide complex as a solution containing the second antibody flows through the membrane. The detection of bound second antibody may then be performed as described above. In the strip test format, one end of the membrane to which antibody is bound is immersed in a solution containing the sample. The sample migrates along the membrane through a region containing second antibody and to the area of immobilized antibody. Concentration of second antibody at the area of immobilized antibody indicates the presence of prostate cancer. Typically, the concentration of second antibody at that site generates a pattern, such as a line, that can be read visually. The absence of such a pattern indicates a negative result. In general, the amount of antibody immobilized on the membrane is selected to generate a visually discernible pattern when the biological sample contains a level of polypeptide that would be sufficient to generate a positive signal in the two-antibody sandwich assay, in the format discussed above. Preferably, the amount of antibody immobilized on the membrane ranges from about 25 ng to about 1 $\mu$g, and more preferably from about 50 ng to about 500 ng. Such tests can typically be performed with a very small amount of biological sample.

Of course, numerous other assay protocols exist that are suitable for use with the antigens or antibodies of the present invention. The above descriptions are intended to be exemplary only.

In another embodiment, the above polypeptides may be used as markers for the progression of prostate cancer. In this embodiment, assays as described above for the diagnosis of prostate cancer may be performed over time, and the change in the level of reactive polypeptide(s) evaluated. For example, the assays may be performed every 24–72 hours for a period of 6 months to 1 year, and thereafter performed as needed. In general, prostate cancer is progressing in those patients in whom the level of polypeptide detected by the binding agent increases over time. In contrast, prostate cancer is not progressing when the level of reactive polypeptide either remains constant or decreases with time.

Antibodies for use in the above methods may be prepared by any of a variety of techniques known to those of ordinary skill in the art. See, e.g., Harlow and Lane, *Antibodies. A Laboratory Manual*, Cold Spring Harbor Laboratory, 1988. In one such technique, an immunogen comprising the antigenic polypeptide is initially injected into any of a wide variety of mammals (e.g., mice, rats, rabbits, sheep and goats). In this step, the polypeptides of this invention may serve as the immunogen without modification. Alternatively, particularly for relatively short polypeptides, a superior immune response may be elicited if the polypeptide is joined to a carrier protein, such as bovine serum albumin or keyhole limpet hemocyanin. The immunogen is injected into the animal host, preferably according to a predetermined schedule incorporating one or more booster immunizations, and the animals are bled periodically. Polyclonal antibodies specific for the polypeptide may then be purified from such antisera by, for example, affinity chromatography using the polypeptide coupled to a suitable solid support.

Monoclonal antibodies specific for the antigenic polypeptide of interest may be prepared, for example, using the technique of Kohler and Milstein, *Eur. J. Immunol.* 6:511–519, 1976, and improvements thereto. Briefly, these methods involve the preparation of immortal cell lines capable of producing antibodies having the desired specificity (i.e., reactivity with the polypeptide of interest). Such cell lines may be produced, for example, from spleen cells obtained from an animal immunized as described above. The spleen cells are then immortalized by, for example, fusion with a myeloma cell fusion partner, preferably one that is syngeneic with the immunized animal. A variety of fusion techniques may be employed. For example, the spleen cells and myeloma cells may be combined with a nonionic detergent for a few minutes and then plated at low density on a selective medium that supports the growth of hybrid cells, but not myeloma cells. A preferred selection technique uses HAT (hypoxanthine, aminopterin, thymidine) selection. After a sufficient time, usually about 1 to 2 weeks, colonies of hybrids are observed. Single colonies are selected and tested for binding activity against the polypeptide. Hybridomas having high reactivity and specificity are preferred.

Monoclonal antibodies may be isolated from the supernatants of growing hybridoma colonies: In addition, various techniques may be employed to enhance the yield, such as injection of the hybridoma cell line into the peritoneal cavity of a suitable vertebrate host, such as a mouse. Monoclonal antibodies may then be harvested from the ascites fluid or the blood. Contaminants may be removed from the antibodies by conventional techniques, such as chromatography, gel filtration, precipitation, and extraction. The polypeptides of this invention may be used in the purification process in, for example, an affinity chromatography step.

Monoclonal antibodies of the present invention may also be used as therapeutic reagents, to diminish or eliminate prostate tumors. The antibodies may be used on their own (for instance, to inhibit metastases) or coupled to one or more therapeutic agents. Suitable agents in this regard include radionuclides, differentiation inducers, drugs, toxins, and derivatives thereof. Preferred radionuclides include $^{90}$Y, $^{123}$I, $^{125}$I, $^{131}$I, $^{186}$Re, $^{188}$Re, $^{211}$At, and $^{212}$Bi. Preferred drugs include methotrexate, and pyrimidine and purine analogs. Preferred differentiation inducers include phorbol esters and butyric acid. Preferred toxins include ricin, abrin, diptheria toxin, cholera toxin, gelonin, *Pseudomonas* exotoxin, *Shigella* toxin, and pokeweed antiviral protein.

A therapeutic agent may be coupled (e.g., covalently bonded) to a suitable monoclonal antibody either directly or indirectly (e.g., via a linker group). A direct reaction between an agent and an antibody is possible when each possesses a substituent capable of reacting with the other. For example, a nucleophilic group, such as an amino or sulfhydryl group, on one may be capable of reacting with a carbonyl-containing group, such as an anhydride or an acid halide, or with an alkyl group containing a good leaving group (e.g., a halide) on the other.

Alternatively, it may be desirable to couple a therapeutic agent and an antibody via a linker group. A linker group can function as a spacer to distance an antibody from an agent in order to avoid interference with binding capabilities. A linker group can also serve to increase the chemical reactivity of a substituent on an agent or an antibody, and thus increase the coupling efficiency. An increase in chemical reactivity may also facilitate the use of agents, or functional groups on agents, which otherwise would not be possible.

It will be evident to those skilled in the art that a variety of bifunctional or polyfunctional reagents, both homo- and hetero-functional (such as those described in the catalog of the Pierce Chemical Co., Rockford, Ill.), may be employed as the linker group. Coupling may be effected, for example, through amino groups, carboxyl groups, sulfhydryl groups or oxidized carbohydrate residues. There are numerous references describing such methodology, e.g., U.S. Pat. No. 4,671,958, to Rodwell et al.

Where a therapeutic agent is more potent when free from the antibody portion of the immunoconjugates of the present invention, it may be desirable to use a linker group which is cleavable during or upon internalization into a cell. A number of different cleavable linker groups have been described. The mechanisms for the intracellular release of an agent from these linker groups include cleavage by reduction of a disulfide bond (e.g., U.S. Pat. No. 4,489,710, to Spitler), by irradiation of a photolabile bond (e.g., U.S. Pat. No. 4,625,014, to Senter et al.), by hydrolysis of derivatized amino acid side chains (e.g., U.S. Pat. No. 4,638,045, to Kohn et al.), by serum complement-mediated hydrolysis (e.g., U.S. Pat. No. 4,671,958, to Rodwell et al.), and acid-catalyzed hydrolysis (e.g., U.S. Pat. No. 4,569,789, to Blattler et al.).

It may be desirable to couple more than one agent to an antibody. In one embodiment, multiple molecules of an agent are coupled to one antibody molecule. In another embodiment, more than one type of agent may be coupled to one antibody. Regardless of the particular embodiment, immunoconjugates with more than one agent may be prepared in a variety of ways. For example, more than one agent may be coupled directly to an antibody molecule, or linkers which provide multiple sites for attachment can be used. Alternatively, a carrier can be used.

A carrier may bear the agents in a variety of ways, including covalent bonding either directly or via a linker group. Suitable carriers include proteins such as albumins (e.g., U.S. Pat. No. 4,507,234, to Kato et al.), peptides and polysaccharides such as aminodextran (e.g., U.S. Pat. No. 4,699,784, to Shih et al.). A carrier may also bear an agent by noncovalent bonding or by encapsulation, such as within a liposome vesicle (e.g., U.S. Pat. Nos. 4,429,008 and 4,873,088). Carriers specific for radionuclide agents include radiohalogenated small molecules and chelating compounds. For example, U.S. Pat. No. 4,735,792 discloses representative radiohalogenated small molecules and their synthesis. A radionuclide chelate may be formed from chelating compounds that include those containing nitrogen and sulfur atoms as the donor atoms for binding the metal, or metal oxide, radionuclide. For example, U.S. Pat. No. 4,673,562, to Davison et al. discloses representative chelating compounds and their synthesis.

A variety of routes of administration for the antibodies and immunoconjugates may be used. Typically, administration will be intravenous, intramuscular, subcutaneous or in the bed of a resected tumor. It will be evident that the precise dose of the antibody/immunoconjugate will vary depending upon the antibody used, the antigen density on the tumor, and the rate of clearance of the antibody.

Diagnostic reagents of the present invention may also comprise DNA sequences encoding one or more of the above polypeptides, or one or more portions thereof. For example, at least two oligonucleotide primers may be employed in a polymerase chain reaction (PCR) based assay to amplify prostate tumor-specific cDNA derived from a biological sample, wherein at least one of the oligonucleotide primers is specific for a DNA molecule encoding a prostate tumor protein of the present invention. The presence of the amplified cDNA is then detected using techniques well known in the art, such as gel electrophoresis. Similarly, oligonucleotide probes specific for a DNA molecule encoding a prostate tumor protein of the present invention may be used in a hybridization assay to detect the presence of an inventive polypeptide in a biological sample.

As used herein, the term "oligonucleotide primer/probe specific for a DNA molecule" means an oligonucleotide sequence that has at least about 60%, preferably at least about 75% and more preferably at least about 90%, identity to the DNA molecule in question. Oligonucleotide primers and/or probes which may be usefully employed in the inventive diagnostic methods preferably have at least about 10–40 nucleotides. In a preferred embodiment, the oligonucleotide primers comprise at least about 10 contiguous nucleotides of a DNA molecule having a sequence selected from SEQ ID Nos: 1–107, 109–111, 115–171, 173–175, 177 and 179–228. Preferably, oligonucleotide probes for use in the inventive diagnostic methods comprise at least about 15 contiguous oligonucleotides of a DNA molecule having a sequence provided in SEQ ID Nos: 1–107, 109–111, 115–171, 173–175, 177 and 179–228. Techniques for both PCR based assays and hybridization assays are well known in the art (see, for example, Mullis et al. Ibid; Ehrlich, Ibid). Primers or probes may thus be used to detect prostate tumor-specific sequences in biological samples, including blood, semen, prostate tissue and/or prostate tumor tissue.

Polypeptides of the present invention that comprise an immunogenic portion of a prostate tumor protein may also be used for immunotherapy of prostate cancer, wherein the polypeptide stimulates the patient's own immune response to prostate tumor cells. In further aspects, the present invention provides methods for using one or more of the immunoreactive polypeptides encoded by a DNA molecule having a sequence provided in SEQ ID NO: 1–107, 109–111, 115–171, 173–175, 177 and 179–228 (or DNA encoding such polypeptides) for immunotherapy of prostate cancer in a patient. As used herein, a "patient" refers to any warm-blooded animal, preferably a human. A patient may be afflicted with a disease, or may be free of detectable disease. Accordingly, the above immunoreactive polypeptides may be used to treat prostate cancer or to inhibit the development of prostate cancer. The polypeptides may be administered either prior to or following surgical removal of primary tumors and/or treatment by administration of radiotherapy and conventional chemotherapeutic drugs.

In these aspects, the polypeptide is generally present within a pharmaceutical composition and/or a vaccine. Pharmaceutical compositions may comprise one or more polypeptides, each of which may contain one or more of the above sequences (or variants thereof), and a physiologically acceptable carrier. The vaccines may comprise one or more of such polypeptides and a non-specific immune response enhancer, such non-specific immune response enhancers being capable of eliciting or enhancing an immune response to an exogenous antigen. Examples of non-specific immune response enhancers include adjuvants, biodegradable microspheres (e.g., polylactic galactide) and liposomes (into which the polypeptide is incorporated). Pharmaceutical compositions and vaccines may also contain other epitopes of prostate tumor antigens, either incorporated into a combination polypeptide (i.e., a single polypeptide that contains multiple epitopes) or present within a separate polypeptide.

Alternatively, a pharmaceutical composition or vaccine may contain DNA encoding one or more of the above polypeptides, such that the polypeptide is generated in situ. In such pharmaceutical compositions and vaccines, the DNA may be present within any of a variety of delivery systems known to those of ordinary skill in the art, including nucleic acid expression systems, bacteria and viral expression systems. Appropriate nucleic acid expression systems contain the necessary DNA sequences for expression in the patient (such as a suitable promoter). Bacterial delivery systems involve the administration of a bacterium (such as *Bacillus-Calmette-Guerrin*) that expresses an epitope of a prostate cell antigen on its cell surface. In a preferred embodiment, the DNA may be introduced using a viral expression system (e.g., vaccinia or other pox virus, retrovirus, or adenovirus), which may involve the use of a non-pathogenic (defective), replication competent virus. Suitable systems are disclosed, for example, in Fisher-Hoch et al., *PNAS* 86:317–321, 1989; Flexner et al., *Ann. N.Y. Acad. Sci.* 569:86–103, 1989; Flexner et al., *Vaccine* 8:17–21, 1990; U.S. Pat. Nos. 4,603, 112, 4,769,330, and 5,017,487; WO 89/01973; U.S. Pat. No. 4,777,127; GB 2,200,651; EP 0,345,242; WO91/02805; Berkner, *Biotechniques* 6:616–627, 1988; Rosenfeld et al., *Science* 252:431–434, 1991; Kolls et al., *PNAS* 91:215–219, 1994; Kass-Eisler et al., *PNAS* 90:11498–11502, 1993; Guzman et al., *Circulation* 88:2838–2848, 1993; and Guzman et al., *Cir. Res.* 73:1202–1207, 1993. Techniques for incorporating DNA into such expression systems are well known to those of ordinary skill in the art. The DNA may also be "naked," as described, for example, in published PCT application WO 90/11092, and Ulmer et al., *Science* 259:1745–1749, 1993, reviewed by Cohen, *Science* 259: 1691–1692, 1993. The uptake of naked DNA may be increased by coating the DNA onto biodegradable beads, which are efficiently transported into the cells.

Routes and frequency of administration, as well as dosage, will vary from individual to individual and may parallel those currently being used in immunotherapy of other diseases. In general, the pharmaceutical compositions and vaccines may be administered by injection (e.g., intracutaneous, intramuscular, intravenous or subcutaneous), intranasally (e.g., by aspiration) or orally. Between 1 and 10 doses may be administered over a 3–24 week period. Preferably, 4 doses are administered, at an interval of 3 months, and booster administrations may be given periodically thereafter. Alternate protocols may be appropriate for individual patients. A suitable dose is an amount of polypeptide or DNA that is effective to raise an immune response (cellular and/or humoral) against prostate tumor cells in a treated patient. A suitable immune response is at least 10–50% above the basal (i.e., untreated) level. In general, the amount of polypeptide present in a dose (or produced in situ by the DNA in a dose) ranges from about 1 pg to about 100 mg per kg of host, typically from about 10 pg to about 1 mg, and preferably from about 100 μg to about 1 μg. Suitable dose sizes will vary with the size of the patient, but will typically range from about 0.01 mL to about 5 mL.

While any suitable carrier known to those of ordinary skill in the art may be employed in the pharmaceutical compositions of this invention, the type of carrier will vary depending on the mode of administration. For parenteral administration, such as subcutaneous injection, the carrier preferably comprises water, saline, alcohol, a lipid, a wax and/or a buffer. For oral administration, any of the above carriers or a solid carrier, such as mannitol, lactose, starch, magnesium stearate, sodium saccharine, talcum, cellulose, glucose, sucrose, and/or magnesium carbonate, may be employed. Biodegradable microspheres (e.g., polylactic glycolide) may also be employed as carriers for the pharmaceutical compositions of this invention. Suitable biodegradable microspheres are disclosed, for example, in U.S. Pat. Nos. 4,897,268 and 5,075,109.

Any of a variety of non-specific immune response enhancers may be employed in the vaccines of this invention. For example, an adjuvant may be included. Most adjuvants contain a substance designed to protect the antigen from rapid catabolism, such as aluminum hydroxide or mineral oil, and a nonspecific stimulator of immune response, such as lipid A, *Bordella pertussis* or *Mycobacterium tuberculosis*. Such adjuvants are commercially available as, for example, Freund's Incomplete Adjuvant and Complete Adjuvant (Difco Laboratories, Detroit, Mich.) and Merck Adjuvant 65 (Merck and Company, Inc., Rahway, N.J.).

Polypeptides disclosed herein may also be employed in ex vivo treatment of prostate cancer. For example, cells of the immune system, such as T cells, may be isolated from the peripheral blood of a patient, using a commercially available cell separation system, such as CellPro Incorporated's (Bothell, Wash.) CEPRATE™ system (see U.S. Pat. No. 5,240,856; U.S. Pat. No. 5,215,926; WO 89/06280; WO 91/16116 and WO 92/07243). The separated cells are stimulated with one or more of the immunoreactive polypeptides contained within a delivery vehicle, such as a microsphere, to provide antigen-specific T cells. The population of tumor antigen-specific T cells is then expanded using standard techniques and the cells are administered back to the patient.

The following Examples are offered by way of illustration and not by way of limitation.

EXAMPLES

Example 1

Isolation and Characterization of Prostate Tumor Polypeptides

This Example describes the isolation of prostate tumor polypeptides from a prostate tumor cDNA library.

A human prostate tumor cDNA expression library was constructed from prostate tumor poly $A^+$ RNA using a Superscript Plasmid System for cDNA Synthesis and Plasmid Cloning kit (BRL Life Technologies, Gaithersburg, Md. 20897), following the manufacturer's protocol. Specifically, prostate tumor tissues were homogenized with polytron (Kinematica, Switzerland) and total RNA was extracted using TRIZOL reagent (BRL Life Technologies) as directed by the manufacturer. The poly $A^+$ RNA was then purified using a Qiagen OLIGOTEX spin column mRNA purification kit (Qiagen, Santa Clarita, Calif. 91355) according to the manufacturer's protocol. First-strand cDNA was synthesized using the NotI/Oligo-dT18 primer. Double-stranded cDNA was synthesized, ligated with EcoRI/BAXI adaptors (Invitrogen, San Diego, Calif.) and digested with NotI. Following size fractionation with CHROMA SPIN-1000 columns (Clontech, Palo Alto, Calif. 94303), the cDNA was ligated into the EcoRI/NotI site of pcDNA3.1 (Invitrogen) and transformed into ElectroMax *E. coli* DH10B cells (BRL Life Technologies) by electroporation.

Using the same procedure, a normal human pancreas cDNA expression library was prepared from a pool of six tissue specimens (Clontech). The cDNA libraries were characterized by determining the number of independent colonies, the percentage of clones that carried insert, the average insert size and by sequence analysis. The prostate tumor library contained $1.64 \times 10^7$ independent colonies, with 70% of clones having an insert and the average insert size being 1745 base pairs. The normal pancreas cDNA library contained $3.3 \times 10^6$ independent colonies, with 69% of clones having inserts and the average insert size being 1120 base pairs. For both libraries, sequence analysis showed that the majority of clones had a full length cDNA sequence and were synthesized from mRNA, with minimal rRNA and mitochondrial DNA contamination.

cDNA library subtraction was performed using the above prostate tumor and normal pancreas cDNA libraries, as described by Hara et al. (*Blood*, 84:189–199, 1994) with some modifications. Specifically, a prostate tumor-specific subtracted cDNA library was generated as follows. Normal pancreas cDNA library (70 μg) was digested with EcoRI, NotI, and SfuI, followed by a filling-in reaction with DNA polymerase Klenow fragment. After phenol-chloroform extraction and ethanol precipitation, the DNA was dissolved in 100 μl of $H_2O$, heat-denatured and mixed with 100 μl (100 μg) of PHOTOPROBE BIOTIN (Vector Laboratories, Burlingame, Calif.). As recommended by the manufacturer, the resulting mixture was irradiated with a 270 W sunlamp on ice for 20 minutes. Additional PHOTOPROBE BIOTIN (50 μl) was added and the biotinylation reaction was repeated. After extraction with butanol five times, the DNA was ethanol-precipitated and dissolved in 23 μl $H_2O$ to form the driver DNA.

To form the tracer DNA, 10 μg prostate tumor cDNA library was digested with BamHI and XhoI, phenol chloroform extracted and passed through CHROMA SPIN-400 columns (Clontech). Following ethanol precipitation, the tracer DNA was dissolved in 5 μl $H_2O$. Tracer DNA was mixed with 15 μl driver DNA and 20 μl of 2× hybridization buffer (1.5 M NaCl/10 mM EDTA/50 mM HEPES pH 7.5/0.2% sodium dodecyl sulfate), overlaid with mineral oil, and heat-denatured completely. The sample was immediately transferred into a 68° C. water bath and incubated for 20 hours (long hybridization [LH]). The reaction mixture was then subjected to a streptavidin treatment followed by phenol/chloroform extraction. This process was repeated three more times. Subtracted DNA was precipitated, dissolved in 12 μl $H_2O$, mixed with 8 μl driver DNA and 20 μl of 2× hybridization buffer, and subjected to a hybridization at 68° C. for 2 hours (short hybridization [SH]). After removal of biotinylated double-stranded DNA, subtracted cDNA was ligated into BamHI/XhoI site of chloramphenicol resistant pBCSK$^+$ (Stratagene, La Jolla, Calif. 92037) and transformed into ElectroMax *E. coli* DH10B cells by electroporation to generate a prostate tumor specific subtracted cDNA library (prostate subtraction 1).

To analyze the subtracted cDNA library, plasmid DNA was prepared from 100 independent clones, randomly picked from the subtracted prostate tumor specific library and grouped based on insert size. Representative cDNA clones were further characterized by DNA sequencing with a Perkin Elmer/Applied Biosystems Division Automated Sequencer Model 373A (Foster City, Calif.). Six cDNA clones, hereinafter referred to as F1-13, F1-12, F1-16, H1-1, H1-9 and H1-4, were shown to be abundant in the subtracted prostate-specific cDNA library. The determined 3' and 5' cDNA sequences for F1-12 are provided in SEQ ID NO: 2 and 3, respectively, with determined 3' cDNA sequences for F1-13, F1-16, H1-1, H1-9 and H1-4 being provided in SEQ ID No: 1 and 4–7, respectively.

The cDNA sequences for the isolated clones were compared to known sequences in the gene bank using the EMBL and GenBank databases (release 96). Four of the prostate tumor cDNA clones, F1-13, F-16, H1-1, and H1-4, were determined to encode the following previously identified proteins: prostate specific antigen (PSA), human glandular kallikrein; human tumor expression enhanced gene, and mitochondria cytochrome C oxidase subunit II. H1-9 was found to be identical to a previously identified human autonomously replicating sequence. No significant homologies to the cDNA sequence for F1-12 were found.

Subsequent studies led to the isolation of a full-length cDNA sequence for F1-12. This sequence is provided in SEQ ID NO: 107, with the corresponding predicted amino acid sequence being provided in SEQ ID NO: 108.

To clone less abundant prostate tumor specific genes, cDNA library subtraction was performed by subtracting the prostate tumor cDNA library described above with the normal pancreas cDNA library and with the three most abundant genes in the previously subtracted prostate tumor specific cDNA library: human glandular kallikrein, prostate specific antigen (PSA), and mitochondria cytochrome C oxidase subunit II. Specifically, 1 µg each of human glandular kallikrein, PSA and mitochondria cytochrome C oxidase subunit II cDNAs in pCDNA3.1 were added to the driver DNA and subtraction was performed as described above to provide a second subtracted cDNA library hereinafter referred to as the "subtracted prostate tumor specific cDNA library with spike".

Twenty-two cDNA clones were isolated from the subtracted prostate tumor specific cDNA library with spike. The determined 3' and 5' cDNA sequences for the clones referred to as J1-17L1-12, N1-1862, J1-13, J1-19, J1-25, J1-24, K1-58, K1-63, L1-4 and L1-14 are provided in SEQ ID Nos: 8–9, 10–11, 12–13, 14–15, 16–17, 18–19, 20–21, 22–23, 24–25, 26–27 and 28–29, respectively. The determined 3' cDNA sequences for the clones referred to as J1-12, J1-16, J1-21, K1-48, K1-55, L1-2, L1-6, N1-1858, N1-1860, N1-1861, N1-1864 are provided in SEQ ID Nos: 30–40, respectively. Comparison of these sequences with those in the gene bank as described above, revealed no significant homologies to three of the five most abundant DNA species, (J1-17, L1-12 and N1-1862; SEQ ID Nos: 8–9, 10–11 and 12–13, respectively). Of the remaining two most abundant species, one (J1-12; SEQ ID NO:30) was found to be identical to the previously identified human pulmonary surfactant-associated protein, and the other (K1-48; SEQ ID NO:33) was determined to have some homology to *R. norvegicus* mRNA for 2-arylpropionyl-CoA epimerase. Of the 17 less abundant cDNA clones isolated from the subtracted prostate tumor specific cDNA library with spike, four (J1-16, K1-55, L1-6 and N1-1864; SEQ ID Nos:31, 34, 36 and 40, respectively) were found to be identical to previously identified sequences, two (J1-21 and N1-1860; SEQ ID Nos: 32 and 38, respectively) were found to show some homology to non-human sequences, and two (L1-2 and N1-1861; SEQ ID Nos: 35 and 39, respectively) were found to show some homology to known human sequences. No significant homologies were found to the polypeptides J1-13, J1-19, J1-24, J1-25, K1-58, K1-63, L1-4, L1-14 (SEQ ID Nos: 14–15, 16–17, 20–21, 18–19, 22–23, 24–25, 26–27, 28–29, respectively).

Subsequent studies led to the isolation of full length cDNA sequences for J1-17, L1-12 and N1-1862 (SEQ ID NOS: 109–111, respectively). The corresponding predicted amino acid sequences are provided in SEQ ID NOS: 112–114.

In a further experiment, four additional clones were identified by subtracting a prostate tumor cDNA library with normal prostate cDNA prepared from a pool of three normal prostate poly A+ RNA (prostate subtraction 2). The determined cDNA sequences for these clones, hereinafter referred to as U1-3064, U1-3065, V1-3692 and 1A-3905, are provided in SEQ ID NO: 69–72, respectively. Comparison of the determined sequences with those in the gene bank revealed no significant homologies to U1-3065.

A second subtraction with spike (prostate subtraction spike 2) was performed by subtracting a prostate tumor specific cDNA library with spike with normal pancreas cDNA library and further spiked with PSA, J1-17, pulmonary surfactant-associated protein, mitochondrial DNA, cytochrome c oxidase subunit II, N1-1862, autonomously replicating sequence, L1-12 and tumor expression enhanced gene. Four additional clones, hereinafter referred to as V1-3686, R1-2330, 1B-3976 and V1-3679, were isolated. The determined cDNA sequences for these clones are provided in SEQ ID NO:73–76, respectively. Comparison of these sequences with those in the gene bank revealed no significant homologies to V1-3686 and R1-2330.

Further analysis of the three prostate subtractions described above (prostate subtraction 2, subtracted prostate tumor specific cDNA library with spike, and prostate subtraction spike 2) resulted in the identification of sixteen additional clones, referred to as 1G-4736, 1G-4738, 1G-4741, 1G-4744, 1G-4734, 1H-4774, 1H-4781, 1H-4785, 1H-4787, 1H-4796, 1I-4810, 1-4811, 1J-4876, 1K-4884 and 1K-4896. The determined cDNA sequences for these clones are provided in SEQ ID NOS: 77–92, respectively. Comparison of these sequences with those in the gene bank as described above, revealed no significant homologies to 1G-4741, 1G-4734, 1I-4807, 1J-4876 and 1H-4896 (SEQ ID NOS: 79, 81, 87, 90 and 92, respectively). Further analysis of the isolated clones led to the determination of extended cDNA sequences for 1G-4736, 1G-4738, 1G-4741, 1G-4744, 1H-4774, 1H-4781, 1H-4785, 1H-4787, 1H-4796, 1I-4807, 1J-4876, 1K-4884 and 1K-4896, provided in SEQ ID NOS: 179–188 and 191–193, respectively, and to the determination of additional partial cDNA sequences for 1I-4810 and 1I-4811, provided in SEQ ID NOS: 189 and 190, respectively.

An additional subtraction was performed by subtracting a normal prostate cDNA library with normal pancreas cDNA (prostate subtraction 3). This led to the identification of six additional clones referred to as 1G-4761, 1G-4762, 1H-4766, 1H-4770, 1H-4771 and 1H-4772 (SEQ ID NOS: 93–98). Comparison of these sequences with those in the gene bank revealed no significant homologies to 1G-4761 and 1H-4771 (SEQ. ID NOS: 93 and 97, respectively). Further analysis of the isolated clones led to the determination of extended cDNA sequences for 1G-4761, 1G-4762, 1H-4766 and 1H-4772 provided in SEQ ID NOS: 194–196 and 199, respectively, and to the determination of additional partial cDNA sequences for 1H-4770 and 1H-4771, provided in SEQ ID NOS: 197 and 198, respectively.

Subtraction of a prostate tumor cDNA library, prepared from a pool of polyA+ RNA from three prostate cancer patients, with a normal pancreas cDNA library (prostate subtraction 4) led to the identification of eight clones, referred to as 1D-4297, 1D-4309, 1D.1-4278, 1D-4288, 1D-4283, 1D-4304, 1D-4296 and 1D-4280 (SEQ ID NOS: 99–107). These sequences were compared to those in the gene bank as described above. No significant homologies were found to 1D-4283 and 1D-4304 (SEQ ID NOS: 103 and 104, respectively). Further analysis of the isolated clones led to the determination of extended cDNA sequences for 1D-4309, 1D.1-4278, 1D-4288, 1D-4283, 1D-4304, 1D-4296 and 1D-4280, provided in SEQ ID NOS: 200–206, respectively.

cDNA clones isolated in prostate subtraction 1 and prostate subtraction 2, described above, were colony PCR amplified and their mRNA expression levels in prostate tumor, normal prostate and in various other normal tissues were determined using microarray technology (Synteni, Palo Alto, Calif.). Briefly, the PCR amplification products were dotted onto slides in an array format, with each product occupying a unique location in the array. mRNA was extracted from the tissue sample to be tested, reverse transcribed, and fluorescent-labeled cDNA probes were generated. The microarrays were probed with the labeled cDNA probes, the slides scanned and fluorescence intensity was measured. This intensity correlates with the hybridization intensity. Two novel clones (referred to as P509S and P510S) were found to be over-expressed in prostate tumor and normal prostate and expressed at low levels in all other normal tissues tested (liver, pancreas, skin, bone marrow, brain, breast, adrenal gland, bladder, testes, salivary gland, large intestine, kidney, ovary, lung, spinal cord, skeletal muscle and colon). The determined cDNA sequences for P509S and P510S are provided in SEQ ID NO: 223 and 224, respectively. Comparison of these sequences with those in the gene bank as described above, revealed some homology to previously identified ESTs.

Example 2

Determination of Tissue Specificity of Prostate Tumor Polypeptides

Using gene specific primers, mRNA expression levels for the representative prostate tumor polypeptides F1-16, H1, J1-17, L1-12, F1-12 and N1-1862 were examined in a variety of normal and tumor tissues using RT-P CR.

Briefly, total RNA was extracted from a variety of normal and tumor tissues using TRIZOL reagent as described above. First strand synthesis was carried out using 1–2 μg of total RNA with SuperScript II reverse transcriptase (BRL Life Technologies) at 42° C. for one hour. The cDNA was then amplified by PCR with gene-specific primers. To ensure the semi-quantitative nature of the RT-PCR, β-actin was used as an internal control for each of the tissues examined. First, serial dilutions of the first strand cDNAs were prepared and RT-PCR assays were performed using β-actin specific primers. A dilution was then chosen that enabled the linear range amplification of the β-actin template and which was sensitive enough to reflect the differences in the initial copy numbers. Using these conditions, the β-actin levels were determined for each reverse transcription reaction from each tissue. DNA contamination was minimized by DNase treatment and by assuring a negative PCR result when using first strand cDNA that was prepared without adding reverse transcriptase.

mRNA Expression levels were examined in four different types of tumor tissue (prostate tumor from 2 patients, breast tumor from 3 patients, colon tumor, lung tumor), and sixteen different normal tissues, including prostate, colon, kidney, liver, lung, ovary, pancreas, skeletal muscle, skin, stomach, testes, bone marrow and brain. F1-16 was found to be expressed at high levels in prostate tumor tissue, colon tumor and normal prostate, and at lower levels in normal liver, skin and testes, with expression being undetectable in the other tissues examined. H-1-1 was found to be expressed at high levels in prostate tumor, lung tumor, breast tumor, normal prostate, normal colon and normal brain, at much lower levels in normal lung, pancreas, skeletal muscle, skin, small intestine, bone marrow, and was not detected in the other tissues tested. J1-17 and L1-12 appear to be specifically over-expressed in prostate, with both genes being expressed at high levels in prostate tumor and normal prostate but at low to undetectable levels in all the other tissues examined. N1-1862 was found to be over-expressed in 60% of prostate tumors and detectable in normal colon and kidney. The RT-PCR results thus indicate that F1-16, H1-1, J1-17, N1-1862 and L1-12 are either prostate specific or are expressed at significantly elevated levels in prostate.

Further RT-PCR studies showed that F1-12 is over-expressed in 60% of prostate tumors, detectable in normal kidney but not detectable in all other tissues tested. Similarly, R1-2330 was shown to be over-expressed in 40% of prostate tumors, detectable in normal kidney and liver, but not detectable in all other tissues tested. U1-3064 was found to be over-expressed in 60% of prostate tumors, and also expressed in breast and colon tumors, but was not detectable in normal tissues.

RT-PCR characterization of R1-2330, U1-3064 and ID-4279 showed that these three antigens are over-expressed in prostate and/or prostate tumors.

Northern analysis with four prostate tumors, two normal prostate samples, two BPH prostates, and normal colon, kidney, liver, lung, pancrease, skeletal muscle, brain, stomach, testes, small intestine and bone marrow, showed that L1-12 is over-expressed in prostate tumors and normal prostate, while being undetectable in other normal tissues tested. J1-17 was detected in two prostate tumors and not in the other tissues tested. N1-1862 was found to be over-expressed in three prostate tumors and to be expressed in normal prostate, colon and kidney, but not in other tissues tested. F1-12 was found to be highly expressed in two prostate tumors and to be undetectable in all other tissues tested.

The micro-array technology described above was used to determine the expression levels of representative antigens described herein in prostate tumor, breast tumor and the following normal tissues: prostate, liver, pancreas, skin, bone marrow, brain, breast, adrenal gland, bladder, testes, salivary gland, large intestine, kidney, ovary, lung, spinal cord, skeletal muscle and colon. L1-12 was found to be over-expressed in normal prostate and prostate tumor, with some expression being detected in normal skeletal muscle. Both J1-12 and F1-12 were found to be over-expressed in prostate tumor, with expression being lower or undetectable in all other tissues tested. N1-1862 was found to be expressed at high levels in prostate tumor and normal prostate, and at low levels in normal large intestine and normal colon, with expression being undetectable in all other tissues tested. R1-2330 was found to be over-expressed in prostate tumor and normal prostate, and to be expressed at lower levels in all other tissues tested. 1D-4279 was found to be over-expressed in prostate tumor and normal prostate, expressed at lower levels in normal spinal cord, and to be undetectable in all other tissues tested.

Example 3

Isolation and Characterization of Prostate Tumor Polypeptides by PCR-Based Subtracton A cDNA subtraction library, containing cDNA from normal prostate subtracted with ten other normal tissue cDNAs (brain, heart, kidney, liver, lung, ovary, placenta, skeletal muscle, spleen and thymus) and then submitted to a first round of PCR amplification, was purchased from Clontech. This library was subjected to a second round of PCR amplification, following the manufacturer's protocol. The resulting cDNA fragments were subcloned into the vector pT7 Blue T-vector (Novagen, Madison, Wis.) and transformed into XL-1 Blue MRF' E. coli (Stratagene). DNA was isolated from independent clones and sequenced using a Perkin Elmer/Applied Biosystems Division Automated Sequencer Model 373A.

Fifty-nine positive clones were sequenced. Comparison of the DNA sequences of these clones with those in the gene bank, as described above, revealed no significant homologies to 25 of these clones, hereinafter referred to as P5, P8, P9, P18, P20, P30, P34, P36, P38, P39, P42, P49, P50, P53, P55, P60, P64, P65, P73, P75, P76, P79, and P84. The determined cDNA sequences for these clones are provided in SEQ ID NO:41–45, 47–52 and 54–65, respectively. P29, P47, P68, P80 and P82 (SEQ ID NO:46, 53 and 66–68, respectively) were found to show some degree of homology to previously identified DNA sequences. To the best of the inventors' knowledge, none of these sequences have been previously shown to be present in prostate.

Further studies using the PCR-based methodology described above resulted in the isolation of more than 180 additional clones, of which 23 clones were found to show no significant homologies to known sequences. The determined cDNA sequences for these clones are provided in SEQ ID NO: 115–123, 127, 131, 137, 145, 147–151, 153, 156–158 and 160. Twenty-three clones (SEQ ID NO: 124–126, 128–130, 132–136, 138–144, 146, 152, 154, 155 and 159) were found to show some homology to previously identified ESTs. An additional ten clones (SEQ ID NO: 161–170) were found to have some degree of homology to known genes. An additional clone, referred to as P703, was found to have five splice variants. The determined DNA sequence for the variants referred to as DE1, DE13 and DE14 are provided in SEQ ID NOS: 171, 175 and 177, respectively, with the corresponding predicted amino acid sequences being provided in SEQ ID NO: 172, 176 and 178, respectively. The determined cDNA sequence for an extended spliced form of P703 is provided in SEQ ID NO: 225. The DNA sequences for the splice variants referred to as DE2 and DE6 are provided in SEQ ID NOS: 173 and 174, respectively.

mRNA Expression levels for representative clones in tumor tissues (prostate (n=5), breast (n=2), colon and lung) normal tissues (prostate (n=5), colon, kidney, liver, lung (n=2), ovary (n=2), skeletal muscle, skin, stomach, small intestine and brain), and activated and non-activated PBMC was determined by RT-PCR as described above. Expression was examined in one sample of each tissue type unless otherwise indicated.

P9 was found to be highly expressed in normal prostate and prostate tumor compared to all normal tissues tested except for normal colon which showed comparable expression. P20 was found to be highly expressed in normal prostate and prostate tumor, compared to: all twelve normal tissues tested. A modest increase in expression of P20 in: breast tumor (n=2), colon tumor and lung tumor was seen compared to all normal tissues except lung (1 of 2). Increased expression of P18 was found in normal prostate, prostate tumor and breast tumor compared to other normal tissues except lung and stomach. A modest increase in expression of P5 was observed in normal prostate compared to most other normal tissues. However, some elevated expression was seen in normal lung and PBMC. Elevated expression of P5 was also observed in prostate tumors (2 of 5), breast tumor and one lung tumor sample. For P30, similar expression levels were seen in normal prostate and prostate tumor, compared to six of twelve other normal tissues tested. Increased expression was seen in breast tumors, one lung tumor sample and one colon tumor sample, and also in normal PBMC. P29 was found to be over-expressed in prostate tumor (5 of 5) and normal prostate (5 of 5) compared to the majority of normal tissues. However, substantial expression of P29 was observed in normal colon and normal lung (2 of 2). P80 was found to be over-expressed in prostate tumor (5 of 5) and normal prostate (5 of 5) compared to all other normal tissues tested, with increased expression also being seen in colon tumor.

Further studies resulted in the isolation of twelve additional clones, hereinafter referred to as 10-d8, 10-h10, 11-c8, 7-g6, 8-b5, 8-b6, 8-d4, 8-d9, 8-g3, 8-h11, 9-f12 and 9-f3. The determined DNA sequences for 10-d8, 10-h10, 11-c8, 8-d4, 8-d9, 8-h11, 9-f12 and 9-f3 are provided in SEQ ID NO: 207, 208, 209, 216, 217, 220, 221 and 222, respectively. The determined forward and reverse DNA sequences for 7-g6, 8-b5, 8-b6 and 8-g3 are provided in SEQ ID NO: 210 and 211; 212 and 213; 214 and 215; and 218 and 219, respectively. Comparison of these sequences with those in the gene bank revealed no significant homologies to the sequence of 9-f3. The clones 10-d8, 11-c8 and 8-h11 were found to show some homology to previously isolated ESTs, while 10-h10, 8-b5, 8-b6, 8-d4, 8-d9, 8-g3 and 9-f12 were found to show some homology to previously identified genes. Further characterization of 7-G6 and 8-G3 showed identity to the known genes PAP and PSA, respectively.

mRNA Expression levels for these clones were determined using the micro-array technology described above. The clones 7-G6, 8-G3, 8-B5, 8-B6, 8-D4, 8-D9, 9-F3, 9-F12, 9-H3, 10-A2, 10-A4 11-C9 and 11-F2 were found to be over-expressed in prostate tumor and normal prostate, with expression in other tissues tested being low or undetectable. Increased expression of 8-F11 was seen in prostate tumor and normal prostate, bladder, skeletal muscle and colon. Increased expression of 10-H 10 was seen in prostate tumor and normal prostate, bladder, lung, colon, brain and large intestine. Incrased expression of 9-B1 was seen in prostate tumor, breast tumor, and normal prostate and skin, with increased expression of 11-C8 being seen in prostate tumor, and normal prostate and large intestine.

An additional cDNA fragment derived from the PCR-based normal prostate subtraction, described above, was found to be prostate specific by both micro-array technology and RT-PCR. The determined cDNA sequence of this clone (referred to as 9-A11) is provided in SEQ ID NO: 226. Comparison of this sequence with those in the public databases revealed 99% identity to the known gene HOXB13.

Further studies led to the isolation of the clones 8-C6 and 8-H7. The determined cDNA sequences for these clones are provided in SEQ ID NO: 227 and 228, respectively. These sequences were found to show some homology to previously isolated ESTs.

Example 4

Synthesis of Polypeptides

Polypeptides may be synthesized on an Applied Biosystems 430A peptide synthesizer using FMOC chemistry with HPTU (O-Benzotriazole-N,N,N',N'-tetramethyluronium hexafluorophosphate) activation. A Gly-Cys-Gly sequence may be attached to the amino terminus of the peptide to provide a method of conjugation, binding to an immobilized surface, or labeling of the peptide. Cleavage of the peptides from the solid support may be carried out using the following cleavage mixture: trifluoroacetic acid:ethanedithiol:thioanisole:water:phenol (40:1:2:2:3). After cleaving for 2 hours, the peptides may be precipitated in cold methyl-t-butyl-ether. The peptide pellets may then be dissolved in water containing 0.1% trifluoroacetic acid (TFA) and lyophilized prior to purification by C18 reverse phase HPLC. A gradient of 0%–60% acetonitrile (containing 0.1% TFA) in water (containing 0.1% TFA) may be used to elute the peptides. Following lyophilization of the pure fractions, the peptides may be characterized using electrospray or other types of mass spectrometry and by amino acid analysis.

From the foregoing, it will be appreciated that, although specific embodiments of the invention have been described herein for the purposes of illustration, various modifications may be made without deviating from the spirit and scope of the invention.

What is claimed is:

1. A method for detecting prostate cancer in a patient, comprising:
   (a) contacting a biological sample selected from the group consisting of blood and sera obtained from the patient with a polyclonal or monoclonal antibody that is specific for the polypeptide sequence consisting of the amino acid sequence encoded by nucleotide residues 1341–2105 of SEQ ID NO:110;
   (b) detecting the level of the polypeptide encoded by SEQ ID NO: 110 in the sample bound by said antibody, and
   (c) comparing the level of the polypeptide detected in (b) with a predetermined cut-off value; thereby detecting prostate cancer in the patient, wherein an amount of polypeptide detected in (b) which is higher than that of the predetermined cut-off value is considered positive for prostate cancer.

2. The method of claim 1, wherein the antibody is a monoclonal antibody.

3. The method of claim 1, wherein the antibody is a polyclonal antibody.

* * * * *